(12) United States Patent
Jordan

(10) Patent No.: US 9,753,036 B2
(45) Date of Patent: Sep. 5, 2017

(54) METHODS AND COMPOSITIONS FOR SCREENING AND DETECTING BIOMARKERS

(71) Applicant: EDP Biotech Corporation, Knoxville, TN (US)

(72) Inventor: Nancy Tommye Ann Jordan, Knoxville, TN (US)

(73) Assignee: EDP BIOTECH CORPORATION, Knoxville, TN (US)

(*) Notice: Subject to any disclaimer, the term of this patent is extended or adjusted under 35 U.S.C. 154(b) by 289 days.

(21) Appl. No.: 14/264,801

(22) Filed: Apr. 29, 2014

(65) Prior Publication Data
US 2015/0309028 A1  Oct. 29, 2015

(51) Int. Cl.
*G01N 33/574* (2006.01)
*C07K 16/30* (2006.01)

(52) U.S. Cl.
CPC ... *G01N 33/57419* (2013.01); *C07K 16/3046* (2013.01); *C07K 2317/33* (2013.01); *C07K 2317/34* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,672,513 A | 9/1997 | Terskikh et al. | |
| 5,817,512 A | 10/1998 | Morrow et al. | |
| 5,750,373 A | 3/1999 | Griffiths et al. | |
| 5,885,793 A | 3/1999 | Griffiths et al. | |
| 5,965,710 A | 10/1999 | Bodmer et al. | |
| 5,969,108 A | 10/1999 | McCafferty et al. | |
| 6,172,197 B1 | 1/2001 | McCafferty et al. | |
| 6,521,404 B1 | 2/2003 | Griffiths et al. | |
| 6,680,053 B2 | 1/2004 | Lee et al. | |
| 6,812,339 B1 | 11/2004 | Venter et al. | |
| RE39,760 E | 8/2007 | Tsang et al. | |
| 7,521,195 B1 | 4/2009 | Joseloff et al. | |
| 7,553,948 B2 | 6/2009 | Cojocaru et al. | |
| 7,569,662 B2 | 8/2009 | Pollock et al. | |
| 7,892,760 B2 | 2/2011 | Birse et al. | |
| 7,998,701 B2 | 8/2011 | Chua et al. | |
| 8,129,114 B2 | 3/2012 | Ford et al. | |
| 8,168,586 B1 | 5/2012 | Fang et al. | |
| 8,188,244 B2 | 5/2012 | La Monica et al. | |
| 8,349,334 B2 | 1/2013 | Chua et al. | |
| 8,642,742 B2 | 2/2014 | Hofer et al. | |
| 2005/0063952 A1 | 3/2005 | Klysner et al. | |
| 2005/0244890 A1 | 11/2005 | Davies et al. | |
| 2011/0097747 A1 | 4/2011 | Jones | |
| 2012/0107347 A1 | 5/2012 | Hodge et al. | |
| 2013/0071417 A1 | 3/2013 | Abdul-Wahid et al. | |
| 2013/0330742 A1 | 12/2013 | Jordan | |

FOREIGN PATENT DOCUMENTS

| | | |
|---|---|---|
| EP | 0346710 B1 | 11/1993 |
| WO | 2011/056198 A1 | 5/2011 |
| WO | WO 2013/054331 A1 | 4/2013 |
| WO | WO 2014/079886 A1 | 5/2014 |

OTHER PUBLICATIONS

Mariuzza et al. (Annu. Rev. Biophys. Biophys. Chem., 16: 139-159, 1987).*
Albrethsen et al., "Upregulated expression of human neutrophil peptides 1, 2 and 3 (HNP 1-3) in colon cancer serum and tumours: a biomarker study"; BMC; 5:8-17 (Jan. 19, 2005).
Allum et al., "Monoclonal Antibodies in the Diagnosis and Treatment of Malignant Conditions"; Ann. Surg.; 18:41-64 (1986).
Anumula et al., "A comprehensive procedure for preparation of partially methylated alditol acetates from glycoprotein carbohydrates"; Anal Biochem; 203(1):101-108 (May 15, 1992).
Baldwin et al., "Monoclonal Antibodies for Cancer Detection and Therapy" (eds.); pp. 65-85, Academic Press 1985).
Bates et al., "A Predicted Three-dimensional Structure for the Carcinoembryonic Antigen (CEA)"; FEBS 10937; 301 (2):207-214 (Apr. 1992).
Blumenthal et al., "Expression Patterns of CEACAM5 and CEACAM6 in Primary and Metastatic Cancers"; BMC Cancer; 7:2 (Jan. 3, 2007).
Boehm et al., "Structural models for carcinoembryonic antigen and its complex with the single-chain Fv antibody molecule MFE23"; FEBS 23739; 475:11-16 (2000).
Boenisch et al., "Rapid Radioimmunoassay of Carcinoembryonic Antigen (CEA) in Ultrafiltered Perchloric Acid Extracts: Results of a Clinical Survey"; Clin Chem Acta; 58:195-206 (1975).
Borrebaeck et al., "Human Monoclonal Antibodies Produced by Primary in vitro Immunization of Peripheral Blood Lymphocytes"; Proc. Natl. Acad. Sci. (USA); 85(11):3995-3999 (Jun. 1, 1988).
Brown et al., "Structural Characterization of Human Melanoma-associated Antigen p97 with Monoclonal Antibodies"; J. Immunol.; 127(2):539-546 (Aug. 1, 1981).

(Continued)

*Primary Examiner* — Brad Duffy
*Assistant Examiner* — Nelson B Moseley, II
(74) *Attorney, Agent, or Firm* — Merchant & Gould P.C.

(57) ABSTRACT

The present invention is concerned with a novel antigens associated with human tumors, including carcinomas of the colon or lung, as well as novel monoclonal antibodies which specifically bind to said antigen. The antibodies bind to normal human cells to a much lesser degree than to tumor cells. The antigens include 100 kDa glycoprotein that has a colorectal cancer membrane bound and a soluble form, has a UV absorbance peak at about 228 nm, an isoelectric point of about 3.5 to 4, a sialic acid content of about 20%, and does not substantially bind to an antibody specific for ACT. The antibodies find use both in methods such as the detection of malignant cells associated with tumors and in monitoring therapeutic treatment of humans with tumors.

13 Claims, 28 Drawing Sheets

(56) References Cited

OTHER PUBLICATIONS

Buchegger et al., "Monoclonal Antibodies Identify a CEA Crossreacting Antigen of 95 kD (NCA-95) Distinct in Antigenicity and Tissue Distribution from the Previously Described NCA of 55 kD"; Int'l J. Cancer; 33(5):643-649 (May 15, 1984).
Ciocca et al., "Immunohistochemical Techniques Using Monoclonal Antibodies"; Meth. Enzymol. ; 121:562-579 (1986).
Colcher et al., Use of Monoclonal Antibodies as Radiopharmaceuticals for the Localization of Human Carcinoma Xenografts in Athymic Mice; Meth. Enzymol.; 121:802-816 (1986).
Crosti et al., "Identification of Novel Subdominant Epitopes on the Carcinoembryonic Antigen Recognized by CD4 + T Cells of Lung Cancer Patients"; J. Immunol.; 176:5093-5099 (2006).
Dell et al., "Mass Spectrometry of Carbohydrate-Containing Biopolymers"; Methods Enzymol.; 230:108-132 (1994).
Fink et al., "Monoclonal Antibodies as Diagnostic Reagents for the Identification and Characterization of Human Tumor Antigens"; Prog. Clin. Pathol. 9; 121-133 (1984) (Exhibit 19).
Genbank, carcinoembryonic antigen-related cell adhesion molecule 5 preproprotein [*Homo sapiens*]; NCBI Reference Sequence NP_0043542; (Sep. 2, 2013) http://www.ncbi.nlm.nih.gov/protein/NP_004354.2 (downloaded from the internet on Sep. 11, 2013).
Hammarstrom et al., "Antigenic Sites in Carcinoembryonic Antigen"; Cancer Res; 49:4852-4858 (1989).
Hanada et al., "Letters to the Editor: Early Detection of Colorectal Cancer Metastasis and Relapse by Recognizing Nonspecific Cross-Reacting Antigen 2 in Commerical Carcinoembryonic Antigen Assays"; Clinical Chemistry; 55 (9):1747-1751 (Sep. 2009).
Hass et al., "Preparation of Synthetic Polypeptide Domains of Carcinoembryonic Antigen and Their Use in Epitope Mapping"; Cancer Res.; 51:1876-1882 (1991).
Hellstrom et al., "Monoclonal Mouse Antibodies Raised Against Human Lung Carcinoma"; Cancer Res.; 46 (8):3917-3923 (1986).
Hoogenboom et al., "By-passing Immunisation—Human Antibodies from Synthetic Repertoires of Germline VH Gene Segments Rearranged in Vitro"; J. Mol. Biol.; 227:381-388 (1992).
Jones et al., "Replacing the complementarity-determining regions in a human antibody with those from a mouse"; Nature; 321:522-525 (May 29, 1986).
Keep et al., "Extraction of CEA from Tumour Tissue, Foetal Colon and Patients' Sera, and the Effect of Perchloric Acid"; Br J. Cancer; 37:171-182 (1978).
Kimball et al., "A Comparison of Methods for the Isolation of Carcinoembryonic Antigen"; Cancer Research; 38:619-623 (Mar. 1978).
Kohler et al., "Continuous cultures of fused cells secreting antibody of predefined specificity"; Nature; 256:495-497 (Aug. 7, 1975).
Kobata et al., "The sugar chain structures of carcinoembryonic antigens and related normal antigens"; Pure & Appl. Chem.; 67(10):1689-1698 (1995).
Kobayashi et al., "Identification of an Antigenic Epitope for Helper T Lymphocytes from Carcinoembryonic Antigen"; Clin. Cancer Res.; 8:3219-3225 (2002).
Kuespert et al., "CEACAMs: their role in physiology and pathophysiology"; Current Opinion in Cell Biology; 18:565-571 (2006).
Kuroki et al., "Biochemical Characterization of 25 Distinct Carcinoembryonic Antigen (CEA) Epitopes Recognized by 57 Monoclonal Antibodies and Categorized into Seven Groups in Terms of Domain Structure of the CEA Molecule"; Hybridoma; 11(4)391-407 (1992).
Kuster et al., "Sequencing of N-linked oligosaccharides directly from protein gels: in-gel deglycosylation followed by matrix-assisted laser desorption/ionization mass spectrometry and normal-phase high-performance liquid chromatography"; Anal. Biochem.; 250(1):82-101 (Jul. 15, 1997).
Lee et al., "Monoclonal Antiidiotypic Antibodies Related to a Murine Oncofetal Bladder Tumor Antigen Induce Specific Cell-mediated Tumor Immunity"; Proc. Nat'l Acad. Sci. (USA); 82(18):6286-6290 (Sep. 1, 1985).
McCafferty et al., "Phage antibodies: filamentous phage displaying antibody variable domains"; Nature; 348:552-554 (Dec. 6, 1990).
Marks et al., "By-passing Immunization—Human Antibodies from V-gene Libraries Displayed on Phage"; J. Mol. Biol.; 222:581-597 (1991).
Marks et al., "By-Passing Immunication: Building High Affinity Human Antibodies by Chain Shuffling"; Bio/Technology; 10:779-783 (Jul. 1992).
Nasu et al., "Epitope Mapping of Monoclonal Antibodies Against N-domain of Carcinoembryonic Antigen"; Immunology Letters; 67:57-62 (1999).
Nepom et al., "Anti-Idiotypic Antibodies and the Induction of Specific Tumor Immunity"; Cancer and Metastasis Reviews; 6(4):489-502 (1987).
Neuberger et al., "Recombinant antibodies possessing novel effector functions"; Nature; 312:604-608 (Dec. 13, 1984).
Oi et al., "Chimeric Antibodies"; Biotechniques; 4(3):214-221 (May 1986).
Peng et al., "The CEA/CD3-Bispecific Antibody MEDI-565 (MT111) Binds a Nonlinear Epitope in the Full-Length but Not a Short Splice Variant of CEA"; PLoS ONE; 7(5):1-14 (May 2012).
Riechmann et al., "Reshaping human antibodies for therapy"; Nature; 332:323-327 (Mar. 24, 1988).
Rousseaux et al., "[63] Optimal conditions for the preparation of proteolytic fragments from monoclonal IgG of different rat IgG subclasses"; Methods in Enzymology; 121:663-669, Academic Press (1986).
Spira et al., "The identification of monoclonal class switch variants by sibselection and an ELISA assay"; J. Immunol. Meth.; 74(2):307-315 (Nov. 1984).
Srivastava et al., "Biomarkers for Early Detection of Colon Cancer"; Clinical Cancer Research; 7:1118-1126 (May 2001).
Thammana et al., "Immunoglobulin Heavy Chain Class Switch from IgM to IgG in a Hybridoma"; Eur. J. Immunol.; 13(8):614-619 (1983).
Tiernan et al., "Carcinoembryonic antigen is the preferred biomarker for in vivo colorectal cancer targeting"; Br. J. cancer; 108(3):662-667 (Feb. 19, 2013).
Jotila et al., "Two-site sandwich enzyme immunoassay with monoclonal antibodies to human alpha-fetoprotein"; J. Immunol. Methods; 42(1):11-15 (Apr. 16, 1981).
Verhoeyen et al., "Reshaping Human Antibodies: Grafting and Antilysozyme Activity"; Science; 239 (4847)1534-1536 (Mar. 25, 1988).
Vaughan et al., "Human Antibodies with Sub-nanomolar Affinities Isolated from a Large Non-immunized Phage Display Library"; Nat. Biotech.; 14:309-314 (1996).
Yeh et al., "A Cell-surface Antigen Which is Present in the Ganglioside Fraction and Shared by Human Melanomas" Int. J. Cancer; 29(3):269-275 (Mar. 15, 1982).
Hatakeyama, K. et al., "Novel Protein Isoforms of Carcinoembryonic Antigen are Secreted from Pancreatic, Gastric and Colorectal Cancer Cells," *BMC Research Notes*, vol. 6, No. 381, pp. 1-10 (2013).
International Search Report and Written Opinion for Application No. PCT/US2015/028028 mailed Aug. 5, 2015.
Zheng, C. et al., "A Novel Anti-CEACAMS Monoclonal Antibody, CC4, Suppresses Colorectal Tumor Growth and Enhances NK Cells-Mediated Tumor Immunity," PLoS ONE, vol. 6, Issue 6, e21146, pp. 1-11 (Jun. 2011).
Wahl et al., "Improved radioimaging and tumor localization with monoclonal F(ab')2"; J. Nucl. Med.; 24:316-325 (Apr. 1983).
Ward et al., "Identification of serum biomarkers for colon cancer by proteomic analysis"; Br. J. Cancer; 94:1898-1905 (2006).
Wensel et al., "'Bifunctional' chelating agents for binding metal ions to proteins, in Radio—immunoimaging and Radioimmunotherapy"; Burchiel et al. (Eds.), Elsevier, N.Y. 185 (1983).
International Search Report dated May 12, 2011, from PCT/US2010/002830 (WO2011/056198 A1).

\* cited by examiner

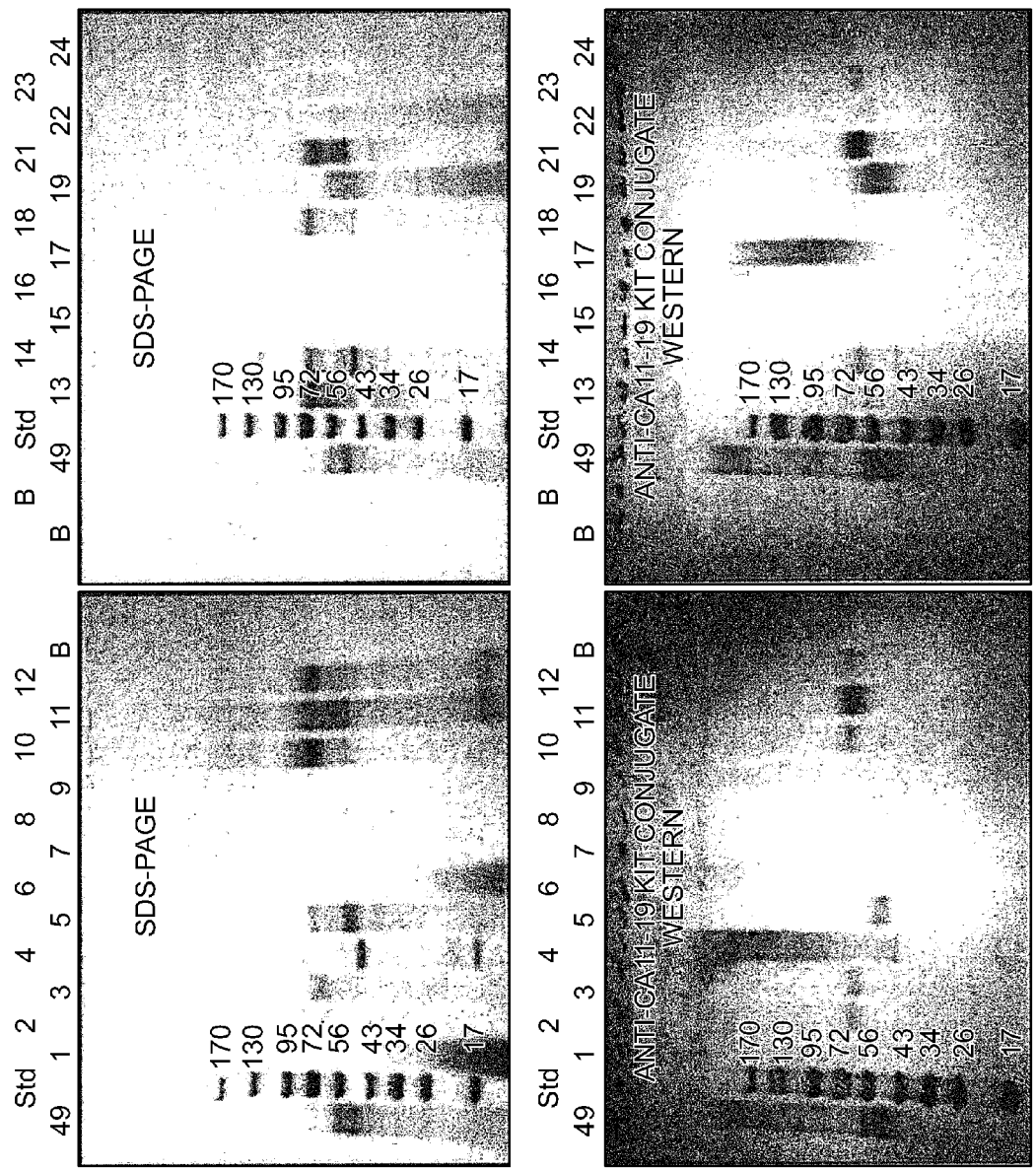

A

B

Figure 2. Separation of CA11-19 168B
STK and NC by SDS-PAGE.

A

B

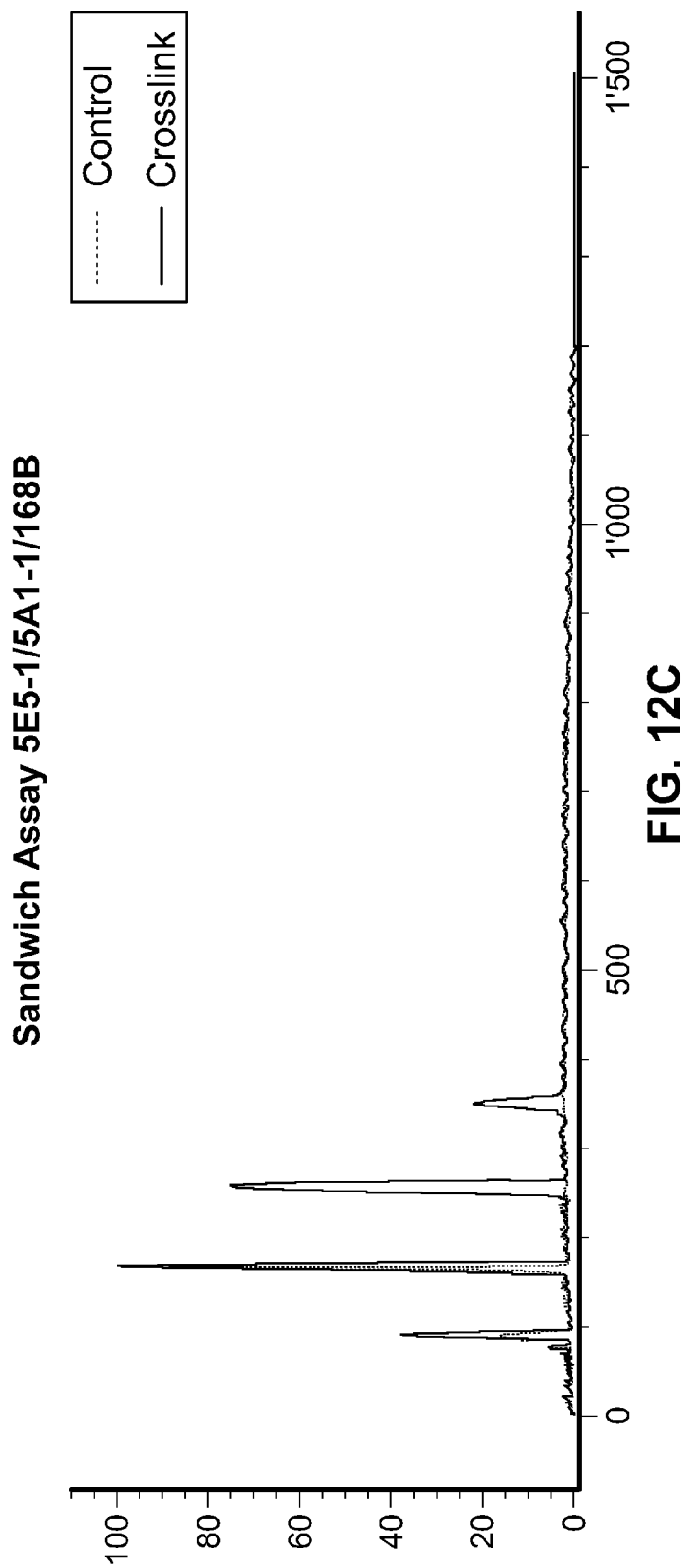

Figure 14: Trypsin, chymotrypsin and ASP-N peptides of 168B (100 kDa Band)(SEQ ID NO:1)

MESPSAPPHR WCIPWQRLLL TASLLTFWNP PTTAKLTIES TPFNVAEGKE VLLLVHNLPQ
HLFGYSWYKG ERVDGNRQII GYVIGTQQAT PGPAYSGREI IYPNASLLIQ NIIQNDTGFY
TLHVIKSDLV NEEATGQFRV YPELPKPSIS SNNSKPVEDK DAVAFTCEPE TQDATYLWWV
NNQSLPVSPR LQLSNGNRTL TLFNVTRNDT ASYKCETQNP VSARRSDSVI LNVLYGPDAP
TISPLNTSYR SGENLNLSCH AASNPPAQYS WFVNGTFQQS TQELFIPNIT VNNSGSYTCQ
AHNSDTGLNR TTVTTITVYE PPKPFITSNN SNPVEDEDAV ALTCEPEIQN TTYLWWVNNQ
SLPVSPRLQL SNDNRTLTLL SVTRNDVGPY ECGIQNELSV DHSDPVILNV LYGPDDPTIS
PSYTYYRPGV NLSLSCHAAS NPPAQYSWLI DENIQQHTQE LFISNITEKN SGLYTCQANN
SASGHSRTTV KTITVSAELP KPSISSNNSK PVEDKDAVAF TCEPEAQNTT YLWWVNGQSL
PVSPRLQLSN GNRTLTLFNV TRNDARAYVC GIQNSVSANR SDPVTLDVLY GPDTPIISPP
DSSYLSGANL NLSCHSASNP SPQYSWRING IPQQHTQVLF IAKITPNNNG TYACFVSNLA
TGRNNSIVKS ITVSASGTSP GLSAGATVGI MIGVLVGVAL I

Figure 15: Interaction 168B/5E5-1

**5E5-1
LC**

*D*IQMTQITSS

**5E5-1
HC**

LSGTAGVHS*QV*QLQQSGAD

HLFGYSWYK—QIIGYVIGTQQATPGPAYSGREIIYPNASL---SDLVNEEATGQFR

Antigen 168B (100 kDA band)

Figure 16 Interaction 168B/5A1-1

5A1-1
LC

5A1-1
HC

SLSASVGDRVTIT*CRASQSISSYLNW*

VKPGASVKLSCKAS*GYTFTNYWIN*WVKP

EVLLLVHNLPQ-HLFGYSWYK-GER<u>VDGNR</u>QIIGY-VIGTQQATPGPAY-SGREIIYPNASL-LIQN

168B (100 kDa material)

Figure 17

5E5-1:amino acid sequence

Heavy chain Amino Acid Sequence (SEQ ID NO:13)
MECSWVMLFILSGTAGVHS

QVQLQQSGADLARPGASVMLSCRASGNTFTDSYINWVKQRPGQGLEWIG**EIYPGNGDVYYNENF
KDKATLTADKSSNTAYMKLSSLTSGDSAVYLCAGSNMITTVFAY**WGQGTLVTVS (SEQ ID
NO:119)

AAKTTPPSVYPLAPGSAAQTNSMVTLGCLVKGYFPEPVTVTWNSGSLSSGVHTFPAVLQSDLYTLSSSVTVPSSTWP
SETVTCNVAHPASSTKVDKKIVPRDCGCKPCICTVPEVSSVFIFPPKPKDVLTITLTPKVTCVVVDISKDDPEVQFS
WFVDDVEVHTAQTQPREEQFNSTFRSVSELPIMHQDWLNGKEFKCRVNSAAFPAPIEKTISKTGRPKAPQVYTIPP
PKEQMAKDKVSLTCMITDFFPEDITVEWQWNGQPAENYKNTQPIMDTDGSYFVYSKLNVQKSNWEAGNTFTCSVLHE
GLHNHHTEKSLSHSPGK

Light chain Amino Acid Sequence (SEQ ID NO:29)
MRAPAQLLGLLLLCFQGTRC

DIQMTQITSSLSASLGDRVTISCRASQDIRNYLNWYQQKPDGTVKLLISYTSRLHSGVPSRFSGSGSGTDYSLIISN
LEQEDIATYFCQQGNTLPWTFGGGTKLEIKR (SEQ ID NO:120)

ADAAPTVSIFPPSSEQLTSGGASVVCFLNNFYPKDINVKWKIDGSGRQNGVLNSWTDQDSKDSTYSMSSTLTLTKDE
YERHNSYTCEATHKTSTSPIVKSFNRNEC

Figure 18 Nucleic acid sequence of Heavy and Light Chain of antibody 5E5-1

Antibody Heavy Chain (SEQ ID NO:12)
DNA Sequence
▮▮▮GAATGCAGCTGGGTAATGCTCTTCATCCTCTCAGGAACTGCAGGTGTCCACTCCCAGGTTCAGCTGCAGCAGTC
TGGAGCTGATCTGGCGAGGCCCGGGGCTTCAGTGATGCTGTCCTGCAGGGCTTCTGGCAACACCTTCACTGACTCCT
ATATAAACTGGGTGAAGCAGAGGCCTGGACAGGGCCTTGAGTGGATTGGAGAGATTTATCCTGGAAATGGTGACGTT
TACTACAATGAAAACTTTAAGGACAAGGCCACACTGACTGCAGACAAATCCTCCAACACAGCCTACATGAAGCTCAG
CAGCCTGACATCTGGGGACTCTGCAGTCTATCTCTGTGCAGGATCTAATATGATTACGACGGTCTTTGCGTACTGGG
GCCAAGGGACTCTGGTCACTGTCTCTGCAGCTAAAACGACACCCCATCTGTCTATCCACTGGCCCTGGATCTGCT
GCCCAAACTAACTCCATGGTGACCCTGGGATGCCTGGTCAAGGGCTATTTCCCTGAGCCAGTGACAGTGACCTGGAA
CTCTGGATCCCTGTCCAGCGGTGTGCACACCTTCCCAGCTGTCCTGCAGTCTGACCTCTACACTCTGAGCAGCTCAG
TGACTGTCCCCTCCAGCACCTGGCCCAGCGAGACCGTCACCTGCAACGTTGCCCACCCGGCCAGCAGCACCAAGGTG
GACAAGAAAATTGTGCCCAGGGATTGTGGTTGTAAGCCTTGCATATGTACAGTCCCAGAAGTATCATCTGTCTTCAT
CTTCCCCCCAAAGCCCAAGGATGTGCTCACCATTACTCTGACTCCTAAGGTCACGTGTGTTGTGGTAGACATCAGCA
AGGATGATCCCGAGGTCCAGTTCAGCTGGTTTGTAGATGATGTGGAGGTGCACACAGCTCAGACGCAACCCCGGGAG
GAGCAGTTCAACAGCACTTTCCGCTCAGTCAGTGAACTTCCCATCATGCACCAGGACTGGCTCAATGGCAAGGAGTT
CAAATGCAGGGTCAACAGTGCAGCTTTCCCTGCCCCATCGAGAAAACCATCTCCAAAACCAAAGGCAGACCGAAGG
CTCCACAGGTGTACACCATTCCACCTCCCAAGGAGCAGATGGCCAAGGATAAAGTCAGTCTGACCTGCATGATAACA
GACTTCTTCCCTGAAGACATTACTGTGGAGTGGCAGTGGAATGGGCAGCCAGCGGAGAACTACAAGAACACTCAGCC
CATCATGGACACAGATGGCTCTTACTTCGTCTACAGCAAGCTCAATGTGCAGAAGAGCAACTGGGAGGCAGGAAATA
CTTTCACCTGCTCTGTGTTACATGAGGGCCTGCACAACCACCATACTGAGAAGAGCCTCTCCCACTCTCCTGGTAAA
▮▮▮

Light Chain nucleic acid sequence (SEQ ID NO:25)

ATGATGAGTCCTGCCCAGTTCCTTGGTCTCCTGTTGCTCTGTTTTCAAGGTACCAGAT
GTGATATCCAGATGACACAGATTACTTCTTCCCTGTCTGCCTCTCTGGGAGACAGAG
TCACCATCAGTTGTAGGGCAAGTCAGGACATTAGGAATTATTTAAACTGGTATCAGC
AGAAACCAGATGGAACTGTTAAACTCCTGATCTCCTACACATCAAGATTACATTCAG
GAGTCCCATCAAGGTTCAGTGGCAGTGGGTCTGGAACAGATTATTCTCTCATTATTA
GTAACCTGGAGCAAGAAGATATTGCCACTTACTTTTGCCAACAGGGTAATACGCTTC
CGTGGACGTTCGGTGGAGGCACCAAACTGGAAATCAAACGGGCTGATGCTGCACCA
ACTGTATCCATCTTCCCACCATCCAGTGAGCAGTTAACATCTGGAGGTGCCTCAGTC
GTGTGCTTCTTGAACAACTTCTACCCCAAAGACATCAATGTCAAGTGGAAGATTGAT
GGCAGTGAACGACAAAATGGCGTCCTGAACAGTTGGACTGATCAGGACAGCAAAGA
CAGCACCTACAGCATGAGCAGCACCCTCACGTTGACCAAGGACGAGTATGAACGAC
ATAACAGCTATACCTGTGAGGCCACTCACAAGACATCAACTTCACCCATTGTCAAGA
GCTTCAACAGGAATGAGTGTTAG

Figure 19 Amino acid sequence of Heavy and Light Chain of antibody 5A1-1

Heavy Chain amino acid sequence (SEQ ID NO:23)

LP
*QVQLE*ESGAE LVKPGASVKL SCKASGYTFT NYWINWVKQR PGQGLEWIGN
IYPGSTRANY NEKFKSKATL TVDTSSSTAY MQVSSLTSDD SAVYY**CTRTH
SI**WGQGTQVT VS (SEQ ID NO:121)

AAKTTPPSVYS

Light Chain amino acid sequence (SEQ ID NO:34)

*DIVLT*QTPSS LSASVGDRVT ITCRASQSIS SYLNWYQQKP GKAPKLLIYA
ASSLQSGVPS RFSGSGSGTD FTLTISSLQP EDFATYYCQQ TVVAPPLFGQ
GTKVEIKRAD (SEQ ID NO:122)

AAPTVST

Figure 20 Heavy and Light chain variable region Nucleic acid sequences of antibody 5A1-1

Heavy chain variable region nucleic acid sequence (SEQ ID NO:24)

CTTCCGCAAGTGCAGCTGGAGGAGTCTGGTGCTGAGCTTGTGAAGCCTGGGGCCTCA
GTGAAGCTGTCCTGCAAGGCTTCTGGCTACACTTTCACCAACTACTGGATAAACTGG
GTGAAGCAGAGGCCTGGACAAGGCCTTGAGTGGATTGGAAATATTTATCCTGGTAG
TACTAGGGCTAATTATAATGAGAAATTCAAGAGCAAGGCCACACTGACTGTAGACA
CATCCTCCAGCACAGCCTACATGCAGGTCAGCAGCCTGACATCTGACGACTCTGCGG
TCTATTATTGTACAAGAACCCACAGTATCTGGGGCCAAGGGACTCAGGTCACTGTCT
CTGCAGCCAAAACGACACCCCCATCTGTCTATTCC

Light chain variable region nucleic acid sequence (SEQ ID NO:30)

GGGACATTGTGCTCACACAGACTCCATCCTCCCTGTCTGCATCTGTAGGAGACAGAG
TCACCATCACTTGCCGGGCAAGTCAGAGCATTAGCAGCTATTTAAATTGGTATCAGC
AGAAACCAGGGAAAGCCCCTAAGCTCCTGATCTATGCGGCATCCAGTTTGCAAAGT
GGGGTCCCATCAAGGTTCAGTGGCAGTGGATCTGGGACAGATTTCACTCTCACCATC
AGCAGTCTGCAACCTGAAGATTTTGCAACTTACTACTGTCAACAGACGGTTGTGGCG
CCTCCGTTATTCGGCCAAGGGACCAAGGTGGAAATCAAACGTGCAGATGCTGCACC
AACTGTATCCACC

METHODS AND COMPOSITIONS FOR SCREENING AND DETECTING BIOMARKERS

BACKGROUND

Carcinomas cause millions of deaths annually. Of all cancers, colorectal cancer is the second leading cause of cancer-related deaths in the U.S. Most cases of carcinomas are incurable by chemotherapy and radiation therapy unless detected and treated in the early stages of the disease. The more advanced a cancer is when it is diagnosed; the less likely it is that therapy will be effective. Therefore, despite the advances in cancer research, there remains a need for novel antibodies useful for the early diagnosis and treatment of carcinomas of the colon, and lung.

Generally, antibodies are used as invaluable reagents in diagnostics. In fact, they have played a major role in deciphering the functions of various bio-molecules in biosynthetic pathways. They have also become the reagents of choice for identification and characterization of tumor specific antigens and have become a valuable tool in the classification of cancer. Once tumor-associated antigens have been purified from tissue extracts, such antigens can be used to elicit production of antibodies to the antigen by injection into animals. Monoclonal antibodies can then be produced. Such antibodies are useful both therapeutically and diagnostically.

In vitro diagnostic methods are known in the art and include immunohistiological detection of tumor cells (e.g., on human tissue, cells or excised tumor specimens) or serologic detection of tumor-associated antigens (e.g., in blood samples or other biological fluids). Immunohistiological techniques involve contacting a biological specimen such as a tumor tissue specimen with the antibody of the invention and then detecting the presence on the specimen of the antibody complexed to its antigen. The formation of such antibody-antigen complexes with the specimen indicates the presence of tumor cells in the tissue. Detection of the antibody on the specimen can be accomplished using techniques known in the art, such as the immunoperoxidase staining technique, the avidin-biotin (ABC) technique or immunofluorescence techniques (see Ciocca et al., Meth. Enzymol., 121:562-79 (1986); Kimball (ed.), Introduction To Immunology (2nd Ed.), pp. 113-117, Macmillan Publ. Co. (1986)).

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample (see, e.g., Uotila et al., J. Immunol. Methods, 42:11 (1981); Allum et al., "Monoclonal Antibodies in the Diagnosis and Treatment of Malignant Conditions" Surg. Ann., 18:41-64, 48-51 (1986); Sikora et al. (eds.), Monoclonal Antibodies, pp. 32-52, Blackwell Scientific Publications, (1984)).

However, in some cases, serological techniques have not produced results robust enough to be useful for cancer screening. Serum markers such as CEA, CA19-9 and CA242 have all been shown to have poor sensitivity and specificity for colon cancer. CEA was discovered in 1969 and was believed to be a sensitive and specific marker for colon cancer. However, further studies were unable to produce the original results. It was shown that at a cutoff concentration of 2.5 ug/L, CEA screening would yield a sensitivity of 30%-40% and a specificity of 87%. Utilizing these numbers, for every 1 colon cancer patient identified with a CEA-based assay there would be 250 false-positives and 60% of cancers would be missed. Due to these overall poor results these markers are not used for colon cancer screening.

For this reason Fecal Occult Blood (FOB) tests have long been the mainstay of colon cancer screening. Large randomized studies have shown that screening with serial FOB tests reduces mortality from colon cancer. Typical examples of FOB tests come in two types, the guaiac-based tests available under the trade names SKB-Hemoccult II® & Hemoccult II SENSA®, and the immune-chemical tests available under the trade names SKB-HemeSelect® and Entrerix-InSure Fit®. Disadvantages of guaiac-based FOB tests include burdensome dietary restrictions, the inconvenient collection process, the limited single application sensitivity, and the costs associated with poor specificity (5-10% rate of false positives). FOB tests have sensitivity of 25%-40% and specificity of 80%-90%. While the immune-chemical based FOB tests have the advantages of improved compliance due to ease of use and no diet restrictions, sensitivity issues remain.

It is thus apparent that antibodies reactive with an antigen expressed at high levels by a variety of tumors may become useful towards an earlier diagnosis of cancers, the immunological monitoring of cancer patients, as well as for development of improved methods for therapy of cancers. It is also apparent that purified antigens associated with carcinomas derived from specific organs and tissues of the body can be of value for creating such monoclonal antibodies, as well as for creating cancer vaccines. It is also apparent that improved materials and methods for serological assays to identify the presence of cancer in humans would be valuable.

SUMMARY OF THE INVENTION

The disclosure provides immunogenic compositions, antibodies, kits, and methods useful in the early detection of cancers or monitoring the treatment of cancer. In embodiments, the cancers are colon-rectal and lung. Immunogenic compositions include an immunogenic composition comprising an isolated fraction from colorectal and/or liver cancer cell samples having a component of about a 100 kDa glycoprotein that has a membrane bound and a soluble form (e.g. cancer cell membrane bound form), has a UV absorbance peak at about 228 nm, an isoelectric point of about 3.5 to 4, a sialic acid content of about 20%, and does not substantially bind to antibodies specific for anti-chymotrypsin (ACT). In embodiments, the 100 kDa protein has an amino acid sequence of CEACAM 5 isoform 2 (SEQ ID NO:1; FIG. 14). In embodiments, the 100 kDa glycoprotein has a deletion of an alanine at position 320 and an altered glycosylation pattern as compared to 180 kDa CEA.

In some cases, the immunogenic composition is obtained by a method comprising contacting colorectal and/or liver tumor cells with an acid to form an extract; separating components of the extract by molecular weight to form a first fraction comprising components with a molecular weight of about 60 kDa or greater; isolating components of the first fraction that have a molecular weight of about 75 kDa or greater and less than about 200 kDa, and further isolating a fraction that has a molecular weight of about 100 kDa.

In embodiments, the composition further comprises an adjuvant. In specific embodiments, the adjuvant is selected from the group consisting of alum, muramyl dipeptide, and Freund's complete adjuvant. Immunogenic compositions are useful for obtaining antibodies. Antigens described herein may also be detectably labeled or attached to a solid substrate for use in a screening assay.

The disclosure includes antibodies that specifically bind a 100 kDa glycoprotein that has a membrane bound and a soluble form, has a UV absorbance peak at about 228 nm, an isoelectric point of about 3.5 to 4, a sialic acid content of about 20%, and do not substantially bind to ACT are described herein.

In embodiments, an antibody or antigen binding fragment specifically binds to 100 kDa glycoprotein comprising an amino acid sequence of SEQ ID NO:1 and does not bind to one or more linear peptides consisting of a linear peptide of 15 amino acids from amino acids 1-60 of SEQ ID NO:1 as shown in SEQ ID NO:2, a linear peptide of amino acids 111 to 125 of SEQ ID NO:1 as shown in SEQ ID NO:3 and/or a linear peptide of 15 amino acids from amino acids 150-701 of SEQ ID NO:1 as shown in SEQ ID NO:4. In embodiments, the antibodies do not substantially bind to epitopes in domains of CEACAM5 selected from the group consisting of amino acids 146-237 (A1 Ig-2), amino acids 238-323 (B1 Ig-3), amino acids 324-415 (A2 Ig-4), amino acids 416-498 (B2 Ig-5), amino acids 502-593 (A3 Ig-6) and amino acids 594-677 (B3 Ig-7) and combinations thereof. Amino acid numbering of CEACAM5 corresponds to that of in NP_004354; gI 98986445; Uniprot P06731-1.

In embodiments, an antibody or antigen binding fragment does not substantially cross react with CEA of a molecular weight of 180 kDa, CEACAM 6(NCA), CEACAM5 lacking all glycosylation, and/or 100 kDa glycoprotein having a sequence of SEQ ID NO:1 lacking all glycosylation.

In embodiments, an antibody or antigen binding fragment specifically binds to an epitope on a 100 kDa glycoprotein comprising an amino acid sequence of SEQ ID NO:1, the epitope comprising, consisting essentially of, or consisting of amino acids 61-69 HLFGYSWYK (SEQ ID NO:6), 73-77 VDGNR (SEQ ID NO:7) or 69-82 KGERVDGNRQI-IGY (SEQ ID NO:8), and 96-107 SGREIIYPNASL (SEQ ID NO:9) of SEQ ID NO:1. In embodiments, an antibody specifically binds to an epitope on a 100 kDa glycoprotein comprising an amino acid sequence of SEQ ID NO:1, the epitope comprising, consisting essentially of, or consisting of amino acids 61-69(SEQ ID NO:6), 78-98 QII-GYVIGTQQAT PGPAYSGR (SEQ ID NO:10), 96-107 (SEQ ID NO:9), and 127-139 SDLVNEEATGQFR (SEQ ID NO:11). Amino acid numbering corresponding to that of SEQ ID NO:1. In embodiments, the epitope is a conformational epitope in the N terminal amino acids (amino acids 1-150; SEQ ID NO:5) of the 100 kDa glycoprotein. In embodiments, the antibodies do not substantially bind to epitopes in other domains of CEACAM5.

In embodiments, an antibody or antigen binding fragment thereof comprises heavy chain CDRs comprising: CDRH1: (TDSYIN SEQ ID NO:14) or GNTFTDSYIN(SEQ ID NO:15); CDRH2: EIYPGNGDVYYNENFK (SEQ ID NO:16); CDRH3: TTVFAY (SEQ ID NO:17) or LCAGSN-MITTVFAY(SEQ ID NO:18). In embodiments, an antibody or antigen binding fragment thereof comprises heavy chain CDRs comprising: CDRH1: GYTFTNYWIN(SEQ ID NO:19) or NYWIN(SEQ ID NO:20); CDRH2: NIYPG-STRANYNEKFK(SEQ ID NO:21); CDRH3: YCTRTHSI (SEQ ID NO:22).

In embodiments, an antibody or antigen binding fragment thereof comprises light chain CDRs comprising: CDRL1: RASQDIRNYLN(SEQ ID NO:26); CDRL2: YTSRLHS (SEQ ID NO:27); CDRL3: QQGNTLPW (SEQ ID NO:28). In embodiments, an antibody or antigen binding fragment thereof comprises light chain CDRs comprising: CDRL1: RASQSISSYLN(SEQ ID NO:31); CDRL2: AASSLQS (SEQ ID NO:32); CDRL3: QQTVVAPP (SEQ ID NO:33).

In embodiments, an antibody or antigen binding fragment thereof comprises HCDR1/HCDR2/HCDR3 of SEQ ID NOs:14/16/17, SEQ ID NOs:15/16/17, SEQ ID NOs:14/16/18, or SEQ ID NOs:15/16/18; and LCDR1/LCDR2/LCDR3 of SEQ ID NOs:26/27/28. In embodiments, an antibody or antigen binding fragment thereof comprises HCDR1/HCDR2/HCDR3 of SEQ ID NOs:20/21/22 or SEQ ID NOs:19/21/22, and LCDR1/LCDR2/LCDR3 of SEQ ID NOs:31/32/33.

In embodiments, an antibody or antigen binding fragment thereof comprises a heavy chain variable region having an amino acid sequence of SEQ ID NO:119 and light chain variable region having a sequence of SEQ ID NO:120. In other embodiments, an antibody or antigen binding fragment comprises a heavy chain variable region having an amino acid sequence of SEQ ID NO:121 and light chain variable region having an amino acid sequence of SEQ ID NO:122.

Antibodies can be polyclonal, monoclonal, or recombinant. Antibodies can be an antigen binding fragment such as of Fab, single chain antibodies, scFv, F(ab)$_2$ and Fv fragments. Antibodies can be human, synthetic, (eg. phage display), chimeric, or humanized antibodies. In embodiments, antibodies are labeled with a signal generating element. In other embodiments, the label is selected from the group consisting of biotin, fluorescent dyes, chemiluminescent tags, radioactive tags, enzymes, and combinations thereof. In yet other embodiments, the antibody is immobilized on a solid surface.

The disclosure provides immunoassays. In embodiments, the method further comprises testing the subject for a cancer selected from the group consisting of colon-rectal and lung. In embodiments, the testing involves detecting a biomarker of the cancer, imaging of the body of the subject such as a CAT, Pet or MRI scan, and/or conducting a colonoscopy.

In embodiments, the immunoassay is a sandwich assay. An immunoassay comprises a first antibody that specifically binds that specifically binds to a 100 kDa glycoprotein having an amino acid sequence of SEQ ID NO:1, and does not substantially bind to ACT attached to a solid substrate (e.g. a capture antibody), and a second antibody that specifically binds to a 100 kDa glycoprotein that has an amino acid sequence of SEQ ID NO:1, that is labeled with a signal generating element. In embodiments, the first antibody is a monoclonal antibody or a polyclonal antibody. In embodiments, the second antibody is a monoclonal antibody or polyclonal antibody.

The disclosure also provides kits. In embodiments, a kit comprises: a) a first antibody that specifically binds to a 100 kDa glycoprotein that has an amino acid sequence of SEQ ID NO:1 and that does not substantially bind ACT; b) a second antibody that specifically binds to a 100 kDa glycoprotein that has an amino acid sequence of SEQ ID NO:1 and is labeled with a signal generating element; and c) a calibrator. In embodiments, the first antibody is a monoclonal antibody or a polyclonal antibody. In embodiments, the second antibody is a monoclonal antibody or polyclonal antibody. In embodiments, the first antibody has different epitope specificity than the second antibody. In embodiments, the kit also provides instructions for identifying a subject as "at risk" for colorectal cancer if the amount of antigen detected is about 6.5 units/ml or greater.

BRIEF DESCRIPTION OF THE FIGURES

FIG. 9A) is the profile for antigen sample NC. FIG. 9B) is the profile for antigen sample STK.

FIG. 10B shows The MSMS profile of the molecular ion at m/z 953 (Hex-DHex-HexNAc2) (10B) and FIG. 10C shows the MSMS profile of the molecular ion at m/z 1157 (Hex2-DHex-HexNAc2) (10C).

FIG. 11 Analysis of binding of monoclonal antibodies specific for the 100 kDa antigen isolated from colon or liver cancer cells designated antibody 5E5-1 and Antibody 5A1-1 to the 100 kDa antigen designated as 168B.

FIG. 14 shows the sequence of the 168B antigen. Overlap mapping of the trypsin, chymotrypsin and ASP-N peptides covered, 85.6% of the sequence.

FIG. 15 shows the map of the epitope bound by antibody 5E5-1. Amino acids in bold indicate potential points of contact between antibody 5E5-1 and antigen 168B.

FIG. 16 shows the map of the epitope bound by antibody 5A1-1. Amino acids in bold indicate potential points of contact between antibody 5A1-1 and antigen 168B.

FIG. 17 shows the amino acid sequence of the heavy and light chain of antibody 5E5-1. CDR regions are highlighted in bold. N terminal sequence of the heavy and light variable domains are identified by italics.

FIG. 18 shows the nucleic acid sequence of the heavy and light chain of antibody 5E5-1.

FIG. 19 shows the amino acid sequence of the heavy and light chain of antibody 5A1-1. CDR regions are highlighted in bold. N terminal sequence of the heavy and light variable domains are identified by italics.

FIG. 20 shows the nucleic acid sequence of the heavy and light chain of antibody 5A1-1.

DETAILED DESCRIPTION OF INVENTION

Figure 1A:
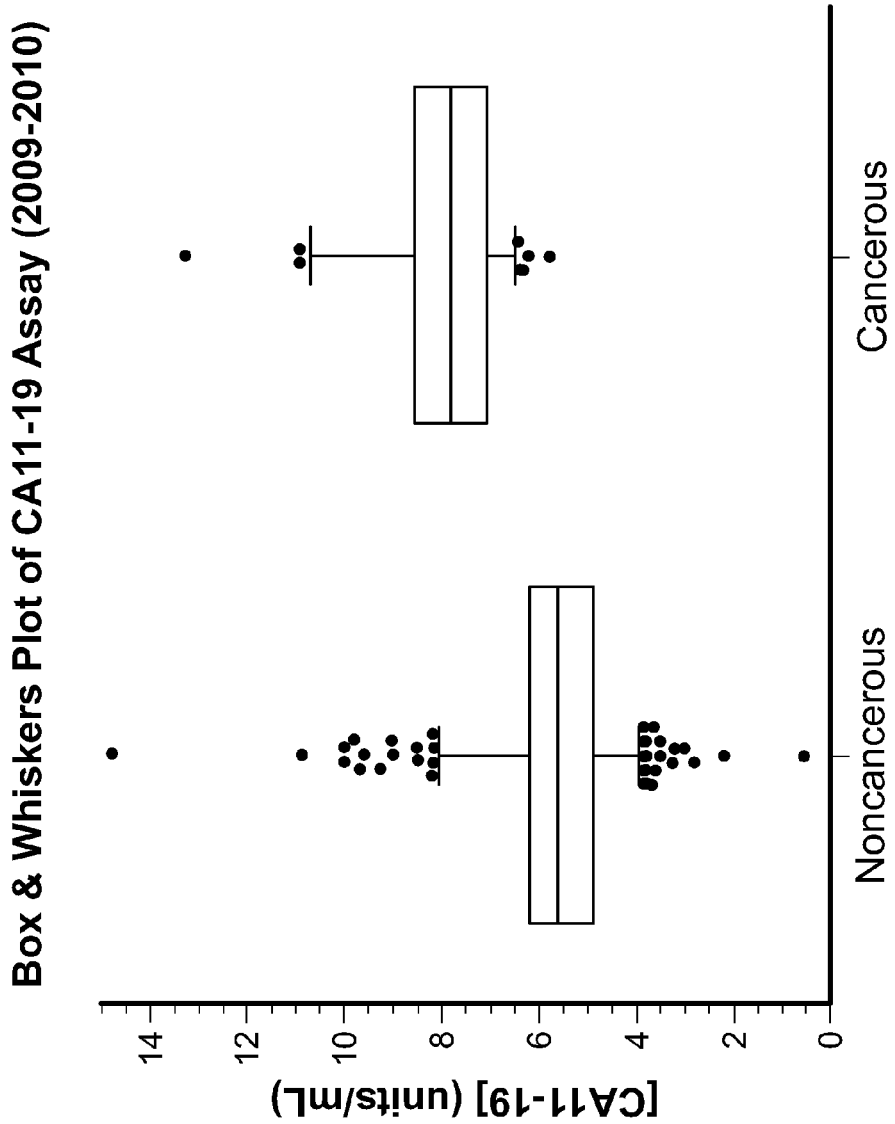
FIG. 1 shows a summary of all data from the 422 patient clinical study. Panel A shows the combined data for all non-cancerous and cancerous patients. The box covers the middle 50% of the data while the line is the median. The whiskers cover the middle 90% of the data (from 5% to 95%). Panel B is a receiver operator characteristic (ROC) curve comparing the cancerous vs. non-cancerous samples.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an", and "the" include the plural reference unless the context clearly indicates otherwise. Thus, for example, the reference to an antibody is a reference to one or more such antibodies, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with numerical values means±20% and with percentages means±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains.

For the purposes of this application the following terms shall have the following meanings:

An "epitope" refers to that portion of any molecule capable of being recognized by, and bound by, an antibody (the corresponding antibody binding region may be referred to as a paratope). In general, epitopes comprise chemically active surface groupings of molecules, for example, amino acids or sugar side chains, and have specific three-dimensional structural characteristics as well as specific charge characteristics.

An "antigen" is a molecule or a portion of a molecule capable of being bound by an antibody. An antigen may have one or more than one epitope. An antigen will bind in a highly selective manner with its corresponding antibody and not with the multitude of other antibodies which may be evoked by other antigens.

An "antibody" includes both intact immunoglobulin molecules as well as portions, fragments, peptides and derivatives thereof, such as, for example, Fab, Fab', F(ab')2, Fv, scFv, CDR regions, or any portion or peptide sequence of the antibody that is capable of binding antigen or epitope. An antibody is said to be "capable of binding" a molecule if it is capable of specifically reacting with the molecule to thereby bind the molecule to the antibody.

Antibody also includes chimeric antibodies, anti-idiotypic (anti-Id) antibodies to antibodies that can be labeled in soluble or bound form, as well as fragments, portions, regions, peptides or derivatives thereof, provided by any known technique, such as, but not limited to, enzymatic cleavage, peptide synthesis, phage display, or recombinant techniques. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce F(ab')2 fragments). See e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

As used herein, "alpha-1-antichymotrypsin", or "ACT" refers to a polypeptide having an amino acid sequence the same as that derived from a naturally occurring noncomplexed polypeptide and that has serine protease inhibitory activity. ACT is also known as SERPINA3, AACT, growth inhibiting protein 24 (GIG24), growth inhibiting protein 25 (GIG25), cell growth inhibiting gene 24/25 protein, and serine proteinase inhibitor clade A, member 3. A representative sequence of ACT is NP_001076/gI 50659080.

As used herein, "carcinoembryonic antigen" or "CEA" refers to a family of polypeptides having an amino acid sequence the same as a naturally occurring polypeptide, and is glycosyl phosphotidyl inositol cell surface anchored glycoprotein. CEA is generally understood to refer to a glycoprotein of a molecular weight of 180 kDa.

As used herein "CEACAM5" refers to a carcinoembryonic antigen that is a member of a family of carcinoembryonic antigens. CEACAM5, without any glycosylation, has an exemplary amino acid sequence found in NP_004354; gI 98986445; Uniprot P06731-1. An isoform of CEACAM5 has an amino acid deletion at amino acid position 320 and has an amino acid sequence of SEQ ID NO:1. (Exemplary sequence found in Uniprot P06731-2). Unglycosylated CEACAM5 contains a signal peptide of 1-34, a protein of 35-685, and amino acids 686-702 that are removed in the mature form. Within the protein several domains are found at amino acids 35-145 (N terminal Ig-1), amino acids 146-237 (A1 Ig-2), amino acids 238-323 (B1 Ig-3), amino acids 324-415 (A2 Ig-4), amino acids 416-498 (B2 Ig-5), amino acids 502-593 (A3 Ig-6) and amino acids 594-677 (B3 Ig-7). Amino acid numbers refer to those of found in NP_004354; gI 98986445; Uniprot P06731-1. The amino acid numbers will be shifted one number from that of amino acid reference sequence of SEQ ID NO:1 because of the deletion of amino acid 320. Antibodies to the domains of CEACAM5 have been characterized as Gold epitope designations: Gold 1: A3B3; Gold 2-A2B2; Gold 3-A3B3; Gold 4-A1B1; and Gold 5-N terminal. CEACAM5 can be produced as a heavily glycosylated form having a molecular weight of 180 kDa and has 28 potential N glycosylation sites.

As used herein, the term "not substantially bind" means that the detectable signal from the binding of the antibody to a component in a sample is within one or two standard deviations of the signal generated due to the presence of an unrelated polypeptide control such as bovine serum albumin.

As used herein "specific binding" refers to an antibody that reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 μM. In certain embodiments, "specifically binds" means that an antibody binds to a protein at times with a $K_D$ of at least about 0.1 μM. or less, and at other times at least about 0.01 μM. or less. It is understood that an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically binds to more than one target. In certain alternative embodiments, an antibody may be bispecific and comprise at least two antigen-binding sites with differing specificities.

The term "comprising" refers to a composition, compound, formulation, or method that is inclusive and does not exclude additional elements or method steps.

The term "consisting of" refers to a compound, composition, formulation, or method that excludes the presence of any additional component or method steps.

The term "consisting essentially of" refers to a composition, compound, formulation or method that is inclusive of additional elements or method steps that do not materially affect the characteristic(s) of the composition, compound, formulation or method.

The term "isolated" refers to the separation of a material from at least one other material in a mixture or from materials that are naturally associated with the material.

The terms "patient" or "subject" are used interchangeably and refer to any member of Kingdom Animalia. Preferably a subject is a mammal, such as a human, domesticated mammal or a livestock mammal.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ration.

The phrase "pharmaceutically-acceptable carrier" refers to a pharmaceutically-acceptable material, composition or vehicle, such as a liquid or solid filler, diluent, excipient, solvent or encapsulating material, involved in carrying or transporting the compound or analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "purified" or "to purify" or "substantially purified" refers to the removal of inactive or inhibitory components (e.g., contaminants) from a composition to the extent that 10% or less (e.g., 10%, 9%, 8%, 7%, 6%, 5%, 4%, 3%, 2%, 1% or less) of the composition is not active compounds or pharmaceutically acceptable carrier.

As used herein, the term "at risk for disease" (e.g., at risk for, cancer, etc.) refers to a subject (e.g., a human) that is predisposed to experiencing a particular disease (e.g., cancer, etc.). This predisposition may be genetic (e.g., a particular genetic tendency to experience the disease, such as heritable disorders), or due to other factors (e.g., hypertension, age, weight, environmental conditions, exposures to detrimental compounds present in the environment, etc.).

Immunogenic Compositions

The disclosure provides immunogenic compositions comprising an isolated fraction from colorectal and/or liver cancer cell samples having components with a molecular weight that comprises a 100 kDa glycoprotein that has a membrane bound and a soluble thin' (e.g. cancer cell membrane bound form), has a UV absorbance peak at about 228 nm, an isoelectric point of about 3.5 to 4, a sialic acid content of about 20%, and does not substantially bind to antibodies specific for ACT.

In embodiments, the immunogenic compositions and/or the isolated fraction are obtained by a method comprising contacting colorectal and/or liver cancer cells with an acid to form an extract; separating components of the extract by molecular weight to form a first fraction having components with a molecular weight of about 60 kDa or greater; isolating components of the first fraction that have a molecular weight of about 75 kDa or greater and less than about 200 kDa, and further isolating a 100 kDa protein. In embodiments, the acid is selected from the group consisting of trichloroacetic acid, dichloroacetic acid, tribromic acid, trifluoric acid, sodium trichloroacetate, hydrochloric acid, and perchloric acid. In embodiments, the acid concentration ranges from about 1 to about 50%. In embodiments, the components are separated by gel filtration. In embodiments, the gel filtration medium is selected from the group consisting of Sepharose, and Superdex gel filtration medium.

In embodiments, the immunogenic composition comprises a 100 kDa glycoprotein isolated from a colorectal or liver cancer cell sample having an amino acid sequence of SEQ ID NO:1. In embodiments, the 100 kDa has a sequence that does not include the leader sequence of amino acids 1-34 of SEQ ID NO:1. While not meant to limit the scope of the disclosure it is thought that the 100 kDa is a form of CEACAM5 with a deletion of an amino acid at position 320 and altered glycosylation as compared to the 180 kDa CEA.

Immunogenic compositions are optionally combined with an adjuvant. An immunogenic effective amount of the antigen is that amount that stimulates an immune response. Immunogenic effective amounts can be determined based on the animal used for immunization. Adjuvants include alum, muramyl peptides, monophosphoryl lipid a, liposomes, incomplete Freunds' adjuvant, and complete Freund's adjuvant.

A typical immunization protocol involves injecting an animal such as mice, goats, sheep, or primates with the immunogenic composition. At least one booster is administered about two weeks after the initial immunization.

Alternatively, the immunogenic composition can be attached to a solid substrate and used to bind antibodies produced in animal models or by phage display. Solid surfaces include membranes, multiwell plates, chromatography media, glass slides, latex beads, magnetic beads, microarray chips, capillary tubes and chips. Similarly, the immunogenic composition may be detectably labeled with a signal generating element. Such labels include fluorescent markers, biotin, enzymes, radioactive labels and the like.

Antibodies

The present disclosure includes novel antibodies, methods for producing the antibodies, and diagnostic and therapeutic methods employing the antibodies.

In embodiments, an antibody specifically binds to a 100 kDa glycoprotein that has a colorectal cancer membrane bound and a soluble form, has a UV absorbance peak at about 228 nm, an isoelectric point of about 3.5 to 4, a sialic acid content of about 20%, and does not substantially bind to 180 kDa glycosylated CEA and/or ACT. In embodiments, antibodies are further screened for binding to human cancer cells, particularly from the lung and/or colon. The antibodies are selected to react with a range of cancers while showing essentially no reactivity with normal human tissues or other types of tumors such as lymphomas.

In embodiments, an isolated antibody or antigen-binding fragment thereof specifically binds to a 100 kDa glycoprotein comprising SEQ ID NO:1, but does not bind to glycosylated 180 kDa CEA and one or more linear peptides consisting of a linear peptide of 15 amino acids from amino acids 1-60 of SEQ ID NO:2, a linear peptide of amino acids 110 to 125 of SEQ ID NO:3, and/or a linear peptide of 15 amino acids from amino acids 150-701 of SEQ ID NO:4. In embodiments, the antibodies are further selected to react with colorectal cancer cells.

In embodiments, the antibody or antigen binding fragment binds to a conformational epitope. In some embodiments, the antibody or antigen binding fragment specifically binds to and/or competes for binding to an epitope comprising, consisting essentially of, consisting of amino acids 61-69 (HLFGYSWYK; SEQ ID NO:6), 73-77 (VDGNR; SEQ ID NO:7) or 69-82 KGERVDGNRQIIGY (SEQ ID NO:8), and 96-107(SGREIIYPNASL; SEQ ID NO:9) of SEQ ID NO:1. In other embodiments, the antibody or antigen binding fragment binds to an epitope comprising, consisting essentially of, consisting of amino acids 61-69 (SEQ ID NO:6), 78-98(QII GYVIGTQQAT PGPAYSGR; SEQ ID NO:10), 96-107(SEQ ID NO:9), and 127-139 (SDLVNEEATGQFR; SEQ ID NO:11) of SEQ ID NO:1. In embodiments, the conformational epitope retains glycosylation.

The antibody or antigen binding fragments thereof does not substantially bind to one or more of the linear peptides of an amino acid sequence selected from the group consisting of SEQ ID NOs:40-101.

In embodiments, the antibody or antigen binding fragment does not substantially bind to epitopes in one or all other domains of CEACAM5 selected from the group consisting of amino acids 146-237 (A1 Ig-2), amino acids 238-322 (B1 Ig-3), amino acids 324-415 (A2 Ig-4), amino acids 416-498 (B2 Ig-5), amino acids 502-593 (A3 Ig-6) and amino acids 594-677 (B3 Ig-7).

In embodiments, an isolated antibody or antigen-binding fragment thereof specifically binds to a 100 kDa glycoprotein comprising SEQ ID NO:1, but does not bind to glycosylated 180 kDa CEA, CEACAM6 (NCA) or unglycosylated CEACAM5 and/or one or more linear peptides consisting of a linear peptide of 15 amino acids from amino acids 1-60 of SEQ ID NO:2, a linear peptide of amino acids 111 to 125 of SEQ ID NO:3, a linear peptide of 15 amino acids from amino acids 150-701 of SEQ ID NO:4, a peptide of amino acids 1-32 including the leader sequence (SEQ ID NO:35), a peptide of amino acids 1-32 without the leader sequence (SEQ ID NO:36), a peptide of amino acids 42-60 (SEQ ID NO:37), a peptide of amino acids 117-127 with the leader (SEQ ID NO:38), a peptide of amino acids 117-127 with the leader (SEQ ID NO:39), and combinations thereof.

In embodiments, an isolated antibody or antigen-binding fragment thereof that specifically binds to a 100 kDa glycoprotein comprising SEQ ID NO:1, but does not bind to glycosylated 180 kDa CEA and comprises: (a) heavy chain CDRs (HCDR1, HCDR2 and HCDR3) from a heavy chain variable region having an amino acid sequence selected from the group consisting of SEQ ID NO:119 and SEQ ID NO:121, and (b) light chain CDRs (LCDR1, LCDR2 and LCDR3) from a light chain variable region having an amino acid sequence selected from the group consisting of SEQ ID NO:120 and SEQ ID NO:122.

In other embodiments, an isolated antibody or antigen-binding fragment thereof comprises: a) HCDR1, HCDR2, and HCDR3 selected from the group consisting of SEQ ID NOs:15/16/17, 14/16/17, 18/20/21 and SEQ ID NO:19/20/21; and b) LCDR1, LCDR2, and LCDR3 selected from the group consisting of SEQ ID NOs:26/27/28 and SEQ ID NOs:31/32/33.

In yet other embodiments, an isolated antibody or antigen binding fragment thereof comprises: a) a heavy chain variable region having an amino acid sequence SEQ ID NO: 119 and a light chain variable region having an amino acid sequence of SEQ ID NO:120; or (b) a heavy chain variable region having an amino acid sequence SEQ ID NO:121 and a light chain variable region having an amino acid sequence of SEQ ID NO:122.

Antibodies include monoclonal, polyclonal, human, humanized, chimeric antibodies, anti-idiotypic (anti-Id) antibodies to antibodies that can be labeled in soluble or bound form, as well as fragments, portions, regions, peptides or derivatives thereof, provided by any known technique, such as, but not limited to, enzymatic cleavage, peptide synthesis, phage display, or recombinant techniques.

Antibody fragments or portions may lack the Fc fragment of intact antibody, clear more rapidly from the circulation, and may have less non-specific tissue binding than an intact antibody such as, for example, Fab, Fab', F(ab')2, Fv, scFv, CDR regions, or any portion or peptide sequence of the antibody that is capable of binding antigen or epitope. Antibody fragments may be produced from intact antibodies using methods well known in the art, for example by proteolytic cleavage with enzymes such as papain (to produce Fab fragments) or pepsin (to produce F(ab')2 fragments). See e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g. U.S. Pat. No. 6,680,053.

Polyclonal antibodies can be prepared by any known method. Polyclonal antibodies are raised by immunizing an animal (e.g. a rabbit, goat, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

The monoclonal antibodies of the present disclosure can be prepared by hybridoma fusion techniques. (see, Kohler and Milstein, Nature, 256:495-97 (1975); Brown et al., J. Immunol., 127 (2):539-46 (1981); and Yeh et al., Int. J. Cancer, 29:269-75 (1982)). These techniques involve the injection of an immunogen (e.g., purified antigen or cells or cellular extracts carrying the antigen) into an animal (e.g., a mouse) so as to elicit a desired immune response (i.e., production of antibodies) in that animal. The immunogenic composition is injected, for example, into a mouse, and after a sufficient time the mouse is sacrificed and somatic antibody-producing lymphocytes are obtained. Antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit and frog somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

Figure 1B:
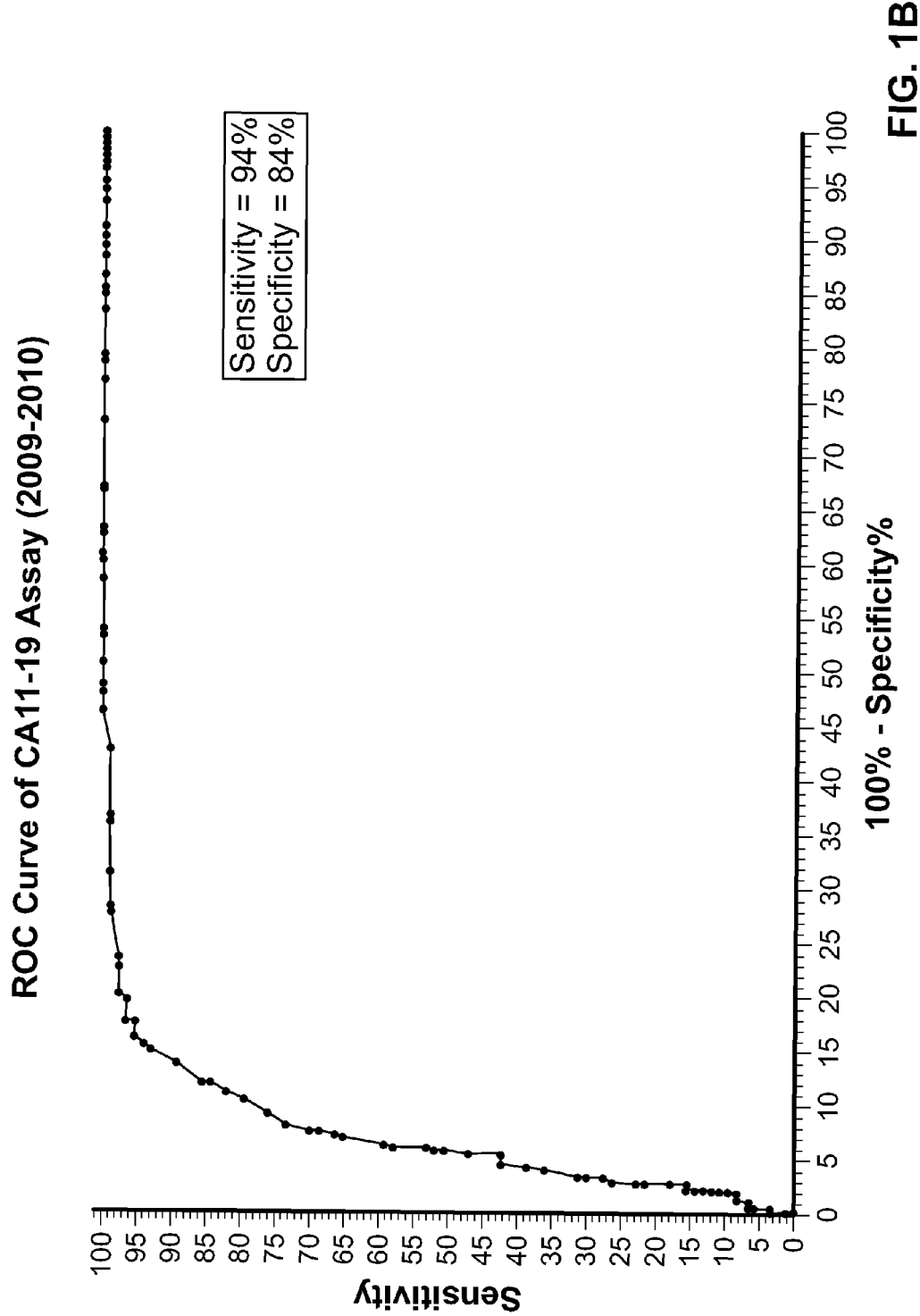
Figure 6:
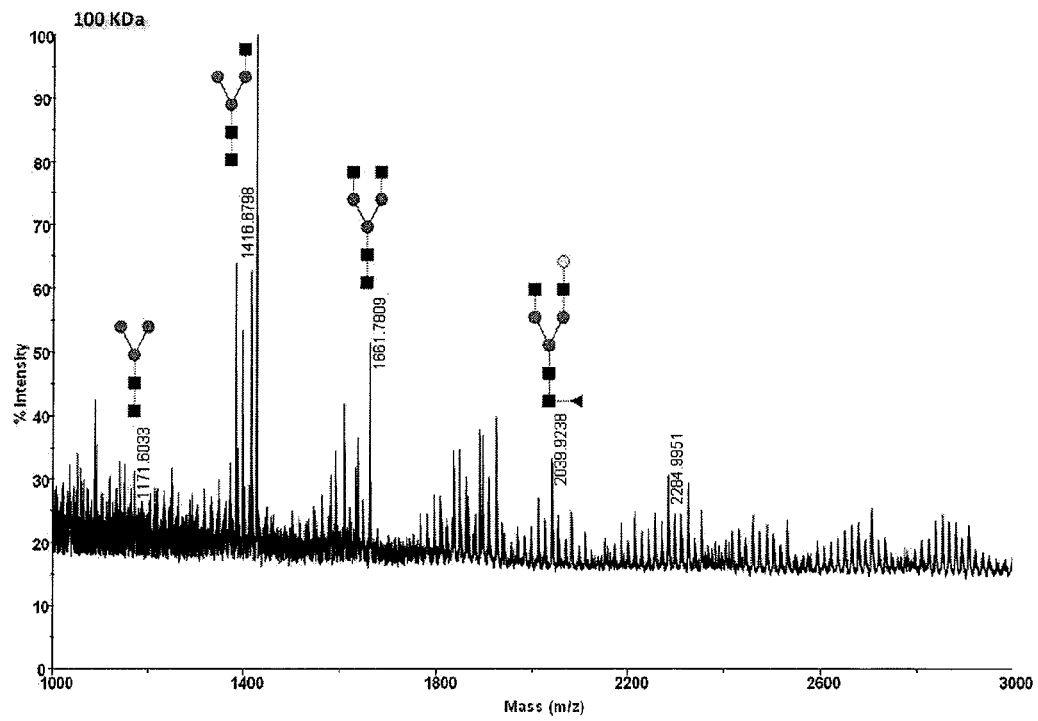
FIG. 6A shows the MALDI-full mass spectra of the 100 kDa band.
FIG. 6B shows the MALDI-full mass spectra of the 45 kDa band.
Figure 6:
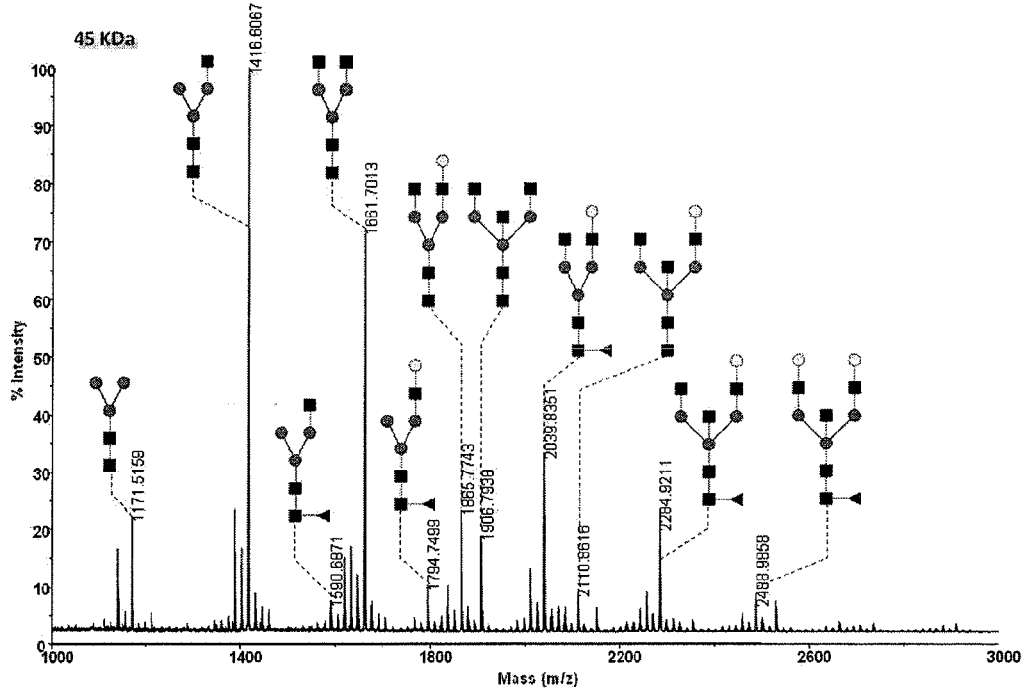

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions, and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al., in Monoclonal Hybridoma Antibodies: Techniques and Applications, Hurell (ed.) pp. 51-52 (CRC Press 1982)). Hybridomas produced according to these methods can be propagated in vitro or in vivo (in ascites fluid) using techniques known in the art (See, generally, Fink et al., supra, at page 123, FIG. 6-1).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion.

Alternatively, monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

Human or humanized antibodies can be directly prepared using various techniques known in the art. Immortalized human B lymphocytes immunized in vitro or isolated from an immunized individual that produce an antibody directed against a target antigen can be generated (See, e.g., U.S. Pat. No. 5,750,373). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016. Examples of methods used to generate humanized antibodies are described in U.S. Pat. No. 5,225,539.

Antibodies can be prepared and selected from a phage library, as described, for example, in Vaughan et al., 1996, Nat. Biotech., 14:309-314, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969, 108, 6,172,197, 5,885,793, 6,521,404 (each of which is incorporated by reference in its entirety). Affinity maturation strategies and chain shuffling strategies (Marks et al., 1992, Bio/Technology 10:779-783, incorporated by reference in its entirety) are known in the art and may be employed to generate high affinity human antibodies.

In embodiments, nucleic acids coding for a heavy chain and light chain variable domains of an antibody of the specificity as described herein are shown in FIGS. 19 and 20. A nucleic acid coding for a heavy chain variable domain of an antibody as described herein comprises a nucleic acid sequence of SEQ ID NO:12 or SEQ ID NO:24. A nucleic acid coding for a light chain of an antibody as described herein comprises a nucleic acid sequence of SEQ ID NO:25 or SEQ ID NO:30.

Screening of antibodies for desired binding specificity is conducted according to standard methods. In embodiments, an antibody specifically binds to a 100 kDa glycoprotein that has a colorectal cancer membrane bound and a soluble form, has a UV absorbance peak at about 228 nm, an isoelectric point of about 3.5 to 4, a sialic acid content of about 20%. In embodiments, the antibodies are also screened for binding to the 100 kDa glycoprotein, and for not substantially binding to 180 kDa CEA and/or ACT. In embodiments, antibodies are isolated that bind to a cancer cell extract obtained by a method comprising a) contacting colorectal and/or liver cancer cells with an acid to form an extract; b) separating components of the extract by molecular weight to form a first fraction having components with a molecular weight of about 60 kDa or greater; c) isolating components of the first fraction that have a molecular weight of about 75 kDa or greater and less than about 200 kDa, and d) isolating a 100 kDa fraction.

In some embodiments, the antibodies are further screened for the ability to bind to tissue samples of cancers as compared to normal tissue of the same tissue type. In embodiments, the antibodies are further screened for binding to colon or lung tumor cells and for lack of binding to a non diseased tissue such as colon, or lung tissue. In yet other embodiments, the antibodies are optionally screened for binding to a 100 kDa glycoprotein that has an amino acid sequence of SEQ ID NO:1.

It should be understood that the present invention encompasses the antibodies described herein and any fragments thereof containing the active binding region of the antibody, such as Fab, F(ab)$_2$ and Fv fragments. Such fragments can be produced from the antibodies using techniques well established in the art (see, e.g., Rousseaux et al., in Methods Enzymol., 121:663-69, Academic Press (1986)).

In addition, embodiments of the present disclosure encompass antibodies that are capable of binding to the same epitope as the antibodies and/or competing with the antibody for binding at that site. These include antibodies having the same epitope specificity as the antibodies that specifically bind to a 100 kDa glycoprotein that has a sequence of SEQ ID NO:1 as described herein, and does not substantially bind to other linear epitopes of CEACAM5 as described herein. For example, class, isotype and other variants of the antibody of the invention may be constructed using recombinant class-switching and fusion techniques known in the art (see, e.g., Thammana et al., Eur. J. Immunol., 13:614 (1983); Spira et al., J. Immunol. Meth., 74:307-15 (1984); Neuberger et al., Nature, 312:604-08 (1984); and Oi et al., supra)). Thus, chimeric antibodies or other recombinant antibodies (e.g., antibody fused to a second protein such as a lymphokine) having the same binding specificity as the antibodies fall within the scope of this invention.

Also included within the scope of the invention are anti-idiotypic antibodies of the antibodies that specifically bind to a 100 kDa glycoprotein that has a colorectal cancer membrane bound and a soluble form, has a UV absorbance peak at about 228 nm, an isoelectric point of about 3.5 to 4, a sialic acid content of about 20%, and does not substantially bind to 180 kDa CEA and/or ACT. These anti-idiotypic antibodies can be produced using the antibodies as immunogen and are useful for diagnostic purposes in detecting humoral response to tumors and in therapeutic applications, e.g., in a vaccine, to induce an anti-tumor response in patients (See, e.g., Nepom et al., Cancer And Metastasis Reviews, 6:487-501 (1987); and Lee et al., Proc. Nat'l. Acad. Sci. (USA), 82:6286-90 (1985)).

Human monoclonal antibodies may be made by using the 100 kDa antigen of the disclosure, to sensitize human lymphocytes to the antigen in vitro followed by EBV-transformation or hybridization of the antigen-sensitized lymphocytes with mouse or human lymphocytes as described by Borrebaeck et al. (Proc. Nat'l. Acad. Sci. (USA), 85:3995-99 (1988)). Therefore, human monoclonal antibodies or chimeric antibodies that bind the 100 kDa antigen are also included within the scope of the present invention.

Methods

The disclosure provides methods of screening, diagnosis, and treatment monitoring of patients having a cancer such as colon cancer or lung cancer.

In embodiments, a method involves combining one or more antibodies that specifically bind to a 100 kDa glycoprotein that has a colorectal cancer membrane bound and a soluble form, has a UV absorbance peak at about 228 nm, an isoelectric point of about 3.5 to 4, a sialic acid content of about 20%, and does not substantially bind to 180 kDa CEA and/or ACT in a human tissue or fluid sample; and detecting the binding of the antibody to the 100 kDa glycoprotein antigen in the sample. In embodiments, the presence or amount of the 100 kDa glycoprotein detected is indicative of the presence of or risk of cancer as compared to control sample without cancer. In embodiments, the 100 kDa glycoprotein is increased in the sample as compared to a control sample from a subject not having cancer. In embodiments, subjects having about 6.5 units/ml or greater of the 100 kDa glycoprotein are at increased risk for colorectal cancer or tubular adenomas.

In embodiments, the sample from the subject is a blood or serum sample and the immunoassay is able to detect the risk of or presence of stage 1 colon carcinoma and/or tubular adenomas. In embodiments, the assay detects these conditions with a sensitivity and/or a specificity of at least 70%, 80%, 90%, 95%, and any number in between 70-100%.

In one aspect, an immunoassay comprises one or more of any of the antibodies as described herein. In embodiments, an immunoassay for determining whether a subject is at risk of colorectal cancer comprises: a) combining an antibody or antigen binding fragment thereof with a human tissue or fluid sample from the subject; wherein the antibody or antigen binding fragment specifically binds to a 100 kDa glycoprotein comprising SEQ ID NO:1, but does not bind to glycosylated 180 kDa CEA and one or more linear peptides consisting of a linear peptide of 15 amino acids from amino acids 1-60 of SEQ ID NO:2, a linear peptide of amino acids 111 to 125 of SEQ ID NO:3, and/or a linear peptide of 15 amino acids from amino acids 150-701 of SEQ ID NO:4; and b) determining the amount of the antigen in the human tissue or fluid by determining the amount of the antibody antigen complex. In am embodiments, the antibody is a monoclonal antibody. In other embodiments, the antibody is a capture antibody attached to a solid substrate. In embodiments, the antibody is detectably labelled. In embodiments, one or more capture antibodies can be utilized.

In other embodiments, an immunoassay further comprises a second antibody that specifically binds to a 100 kDa glycoprotein comprising SEQ ID NO:1, but does not bind to glycosylated 180 kDa CEA and one or more linear peptides consisting of a linear peptide of 15 amino acids from amino acids 1-60 of SEQ ID NO:2, a linear peptide of amino acids 110 to 125 of SEQ ID NO:3, and/or a linear peptide of 15 amino acids from amino acids 150-701 of SEQ ID NO:4; and b) determining the amount of the antigen in the human tissue or fluid by determining the amount of the antibody antigen complex. In am embodiments, the second antibody is a monoclonal antibody. In other embodiments, the second antibody is a capture antibody attached to a solid substrate. In embodiments, the antibody is detectably labelled.

In embodiments, the pair of antibodies in an immunoassay bind to an epitope in the N terminal domain of CEACAM5 (SEQ ID NO:5) and do not bind to epitopes in the other domains of CEACAM5 as described herein.

In embodiments, an immunoassay further comprises an additional antibody that specifically binds to a 100 kDa glycoprotein comprising SEQ ID NO:1. In embodiments the additional antibody is detectably labelled. In embodiments, the additional antibody is a polyclonal antibody.

In embodiments, detectable labels include, without limitation, a radionuclide, an enzyme, a fluorescent agent and a chromophore.

In embodiments, a method of the disclosure involves a screening method for subjects. A subject may visit a health care facility, for example, as a part of routine checkup, and a sample is obtained from the subject. The sample is then screened for the presence of a 100 kDa glycoprotein in accord with methods as described herein. If an increase of the 100 kDa glycoprotein as compared to control is seen in the sample or if the presence or amount of the antigen exceeds a predetermined cutoff value, the health care worker directs the subject to further cancer screening.

In a specific example, a subject comes in for an annual physical and a blood sample is taken. The blood sample is tested in accord with the kits and methods as described herein for the presence or amount of the 100 kDa glycoprotein. If an amount of the 100 kDa antigen detected is about 6.5 units/ml or greater as compared to control in the sample, the health care worker directs the subject to further cancer screening, such as a colonoscopy rather than waiting for the recommended time for conducting such routine screening. In addition, the health care worker may direct the subject to more specific diagnostic methods such as a biopsy, CT scan, MRI, PET scan, alone or in conjunction with other biomarker tests.

In embodiments, the immunoassay methods as described herein identifies with 95% sensitivity the Stage I (Earliest stage histologically confirmed) of Colorectal Cancer. In other embodiments, the immunoassay also identifies over 60% of the Tubular Adenoma polyps which if not removed will most likely become cancer. In embodiments, the antibodies in the immunoassay are selected or modified in order to provide an immunoassay for detecting tubular adenoma or stage I colorectal cancer with a sensitivity of at least 70% to 100% including every number in between and a specificity of at least 70%400%, including every number in between.

In embodiments, a method comprises monitoring treatment of a patient with cancer for efficacy by a) combining an antibody or antigen binding fragment thereof with a human tissue or fluid sample from the subject; wherein the antibody or antigen binding fragment specifically binds to a 100 kDa glycoprotein comprising SEQ ID NO:1, but does not bind to glycosylated 180 kDa CEA and one or more linear peptides consisting of a linear peptide of 15 amino acids from amino acids 1-60 of SEQ ID NO:2, a linear peptide of amino acids 111 to 125 of SEQ ID NO:3, and/or a linear peptide of 15 amino acids from amino acids 150-701 of SEQ ID NO:4; and b) determining the amount of the antigen in the human tissue or fluid by determining the amount of the antibody antigen complex. In embodiments, a decrease in the presence or amount of the antigen detected as compared to a value at the beginning of treatment is indicative of the efficacy of treatment of cancer. In embodiments, the cancer is selected from the group consisting of colon cancer and lung cancer. In embodiments, a treatment is identified as efficacious if it results in a decrease in the amount of the 100 kDa antigen of at least 20% or more. In embodiments, the value at the beginning of treatment is about 6.5 units/ml or greater.

In embodiments, an immunoassay kit is provided for use in the methods described herein. In some embodiments, an immunoassay kit comprises: a) a first and/or second antibody that specifically binds to a 100 kDa glycoprotein comprising SEQ ID NO:1, but does not bind to glycosylated 180 kDa CEA and one or more linear peptides consisting of a linear peptide of 15 amino acids from amino acids 1-60 of SEQ ID NO:2, a linear peptide of amino acids 110 to 125 of SEQ ID NO:3, and/or a linear peptide of 15 amino acids from amino acids 150-701 of SEQ ID NO:4; b) an additional antibody that specifically binds to a 100 kDa glycoprotein comprising SEQ ID NO:1, labeled with a signal generating element; and c) a calibrator.

In embodiments, the antibody or antigen binding fragment binds to a conformational epitope. In some embodiments, the antibody or antigen binding fragment specifically binds to and/or competes for binding to an epitope comprising amino acids 61-69 (SEQ ID NO:6), 73-77 (SEQ ID NO:7), or 69-82 KGERVDGNRQIIGY (SEQ ID NO:8), and 96-107(SEQ ID NO:9) of SEQ ID NO:1. In other embodiments, the antibody or antigen binding fragment specifically binds to an epitope comprising amino acids 61-69(SEQ ID NO:6), 78-98(SEQ ID NO:10), 96-107(SEQ ID NO:9), and 127-139(SEQ ID NO:11) of SEQ ID NO:1.

In embodiments, the antibody or antigen binding fragment does not substantially bind to epitopes in one or all other domains of CEACAM5 selected from the group consisting of amino acids 146-237 (A1 Ig-2), amino acids 238-322 (B1Ig-3), amino acids 324-415 (A2 Ig-4), amino acids 416-498 (B2 Ig-5), amino acids 502-593 (A3 Ig-6) amino acids 594-677 (B3 Ig-7). The amino acid numbers will be shifted one number from SEQ ID NO:1 because of the deletion of amino acid 320. In embodiments, the first and/or second antibody are monoclonal antibodies having an epitope specificity as described herein and the additional antibody is a polyclonal antibody that bind to a number of different epitopes. In embodiments, one or more monoclonal antibodies having different epitope specificity are used as capture antibodies.

In embodiments, the first and second antibody can comprise the CDRs and/or the heavy chain or light chain variable domain sequences as described herein.

In yet other embodiments, a method further comprises displaying the presence or amount of the 100 kDa glycoprotein in the sample on a detectable reader. In yet other embodiments, a method further comprises communicating the presence or amount of the 100 kDa glycoprotein in the sample and/or the presence or absence of cancer to a health care worker. In embodiments, the cancer is selected from the group consisting of as colon cancer and lung cancer. In embodiments, the sample is from a biopsy, a serum, or a blood sample. In embodiments, a detectably labeled antibody is administered in vivo to identify the cancer. In embodiments, the antibody is a human or humanized antibody comprising the heavy and/or light chain CDRS as described herein In embodiments, a detectable reader is able to convert the signal from the detectably labeled antibody into a numerical value. The detectable reader employed depends on the label employed in the immunoassay. For example, for fluorescent labels or antibody labeled with an enzyme that converts a substrate labeled with fluorescent label, a detectable reader is a spectrofluorometer. In other embodiments, the detectable reader detects a radioactive label. In embodiments the detectable reader comprises a display and/or a printer. The reader may include software that automatically takes into account background and uses a standard curve based on an appropriate calibrator to provide a numerical value. In embodiments, the numerical value is communicated to a health care worker via a network including a wireless network.

The methods and kits of the disclosure are useful as point of care assays. The methods and assays as described herein can be used in conjunction with other cancer screening methods such as colonoscopy, lung imaging, biopsy, PET scans, magnetic resonance imaging, ct scans, and assay for other biomarkers associated with cancer.

In embodiments, one or more antibodies are selected to provide an immunoassay that can detect the presence or absence of a 100 kDa glycoprotein as described herein in a tissue or serum sample from a patient having cancer with a specificity and/or sensitivity of at least 70%400%, including every number in between. In embodiments, the first antibody and/or second antibody is a monoclonal antibody. In embodiments, the additional antibody is a polyclonal antibody.

In embodiments, at least two antibodies are selected in order to form an antibody pair that specifically binds to a 100 kDa glycoprotein in a human tissue or bodily fluid sample in an immunoassay. In embodiments, antibodies that bind to the 100 kDa glycoprotein may bind to the same epitope or different epitopes on the protein.

Immunohistiological techniques involve contacting a biological specimen such as a tumor tissue specimen with the antibodies of the invention and then detecting the presence on the specimen of the antibodies complexed to their antigen. The formation of such antibody-antigen complexes with the specimen indicates the presence of tumor cells in the tissue. Detection of the antibodies on the specimen can be accomplished using techniques known in the art, such as the immunoperoxidase staining technique, the avidin-biotin (ABC) technique or immunofluorescence techniques (see, e.g., Ciocca et al., Meth. Enzymol., 121:562-79 (1986); Hellstrom et al., Cancer Research, 46:3917-23 (1986); and Kimball (ed.), Introduction To Immunology (2nd Ed.), pp. 113-117, Macmillan Publ. Co. (1986)).

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample (see, e.g., Uotila et al., J. Immunol. Methods, 42:11 (1981) and Allum et al., "Monoclonal Antibodies in the Diagnosis and Treatment of Malignant Conditions" Surg. Ann., 18:41-64, 48-51 (1986)). These assays, using the antibodies disclosed herein, therefore can be used for the detection in biological fluids of the antigens with which the antibodies react and thus provide for the detection of various carcinomas in human patients. Thus, it is apparent from the foregoing that the antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays (see, e.g., Sikora et al. (eds.), Monoclonal Antibodies, pp. 32-52, Blackwell Scientific Publications, (1984)).

The antibodies of the disclosure are also useful for in vivo diagnostic applications for the detection of human tumors. One such approach involves the detection of tumors in vivo by tumor imaging techniques using the antibodies labeled with an appropriate imaging reagent that produces detectable signal. Imaging reagents and procedures for labeling antibodies with such reagents are well known (see, e.g., Wensel and Meares, Radio Immunoimaging and Radioimmunotherapy, Esevier, N.Y. (1983); Colcher et al., Meth. Enzymol., 121:802-16 (1986)). The labeled antibodies may be detected by a technique such as radionuclear scanning (see, e.g., Bradwell et al. in Monoclonal Antibodies for Cancer Detection and Therapy, Baldwin et al. (eds.), pp. 65-85, Academic Press (1985)).

In some embodiments, the antibodies are useful as a therapeutic agent, especially if linked to a toxic molecule. Antibodies that have been screened for binding to cancer cell tissue as described herein are useful in a method for treating a cancer comprising administering an antibody that specifically binds to a 100 kDa glycoprotein that has a colorectal cancer membrane bound and a soluble form, has a UV absorbance peak at about 228 nm, an isoelectric point of about 3.5 to 4, a sialic acid content of about 20%, has a sequence of SEQ ID NO:1, and does not substantially bind to 180 kDA CEA and/or ACT in a subject suspected of having cancer. In embodiments, the antibodies are human or humanized antibodies comprising the heavy chain CDRs and/or light chain CDRS described herein. In embodiments, the cancer is selected from colon cancer and lung cancer. In embodiments, the cancer is colon cancer.

For diagnostic purposes, antibodies can be attached to a solid surface. Solid surfaces, include without limitation, membranes, multiwell plates, chromatography media, glass slides, latex beads, magnetic beads, microarray chips, capillary tubes and chips. Antibodies can also be labeled with a signal generating element. Signal generating elements include dyes, enzymes, radioactive labels, and chemiluminescent reagents.

In some embodiments, a cutoff value for classifying unknown samples as having the disease or not having the disease is identified. In embodiments, a cutoff value is determined by diluting each of plurality of samples from subjects known to have cancer and detecting the amount of the 100 kDa glycoprotein as compared to a similar set of dilutions from samples subject known not to have cancer. In embodiments, a cutoff is selected that discriminates between bodily fluid samples such as serum samples that are indicative of the presence of cancer as compared to samples known not to have cancer. In embodiments, a cutoff value for the presence of colorectal cancer or tubular adenomas in a serum sample is at least about 6.5 units/ml.

Kits

The disclosure also provides kits for diagnosis of cancer, such as colon or lung cancer. The kit comprises at least one antibody that specifically binds to a 100 kDa glycoprotein that has a colorectal cancer membrane bound and a soluble form, has a UV absorbance peak at about 228 nm, an isoelectric point of about 3.5 to 4, a sialic acid content of about 20%, and does not substantially bind to 180 kDa CEA and/or ACT. In embodiments, the antibody is labeled with a signal generating element.

In yet other embodiments, the kit comprises a) a first and/or second antibody that specifically binds to a 100 kDa glycoprotein comprising SEQ ID NO:1, but does not bind to glycosylated 180 kDa CEACAM5 and one or more linear peptides consisting of a linear peptide of 15 amino acids from amino acids 1-60 of SEQ ID NO:2, a linear peptide of amino acids 111 to 125 of SEQ ID NO:3, and/or a linear peptide of 15 amino acids from amino acids 150-701 of SEQ ID NO:4; b) an additional antibody that specifically binds to a 100 kDa glycoprotein comprising SEQ ID NO:1, labeled with a signal generating element; and c) a calibrator. The antibodies may bind to the same epitope or different epitopes. One of the antibodies is optionally attached to a solid surface. Solid surfaces include membranes, beads, magnetic beads, microwell plates, slides, and micoarrays. The other antibody is optionally labeled with a detectable label or signal generating element. Detectable labels or signal generating elements include biotin, fluorescent dyes, chemiluminescent tags, radioactive tags, and enzymes.

The kit may also optionally comprise a calibrator or standard as a positive or negative control. The standard may comprise a cancer cell extract obtained by a method comprising a) contacting colorectal and/or liver tumor cells with an acid to form an extract; b) separating components of the extract by molecular weight to form a first fraction having components of about 60 kDa or greater; c) isolating components of the first fraction that have a molecular weight of about 75 kDa or greater and less than about 200 kDa; and d) isolating a protein of 100 kDa molecular weight. In embodiments, a calibrator is a 100 kDa glycoprotein having an amino acid sequence of SEQ ID NO:1. In embodiments, the tumor cell is from colorectal cancer. In other embodiments, the kit comprises a negative control such as bovine serum albumin, ACT, and/or 180 kDA CEA.

In embodiments, a kit comprises instructions for conducting an immunoassay to detect the presence of a 100 kDa glycoprotein. The instructions provide a standard curve and instructions for diluting the positive and negative control. The instructions provide a cutoff value of 6.5 units/ml. If the antigen is detected at a level of 6.5 units/ml. or greater the sample is identified as positive for an increased risk of colorectal or lung cancer.

Also included with the disclosure are point of care kits and assay formats. In such assays, the biological sample is blood, urine, saliva, and/or tears and testing is conducted in a doctor's office, emergency room, hospital room, outpatient center, and the like. In embodiments, an antibody as described herein is attached to a solid substrate such as a multiwell plate, dipstick, or membrane based test strip. When the antibody is contacted with the patient sample, if the antigen is detected in the patient sample, the solid substrate changes color in at least one location which can be read visually. In an alternative embodiment, the antibody may be incorporated in a meter that draws a blood sample and then if the antigen is detected gives a detectable signal that is read by the meter.

In order that the invention described herein may be more fully understood, the following examples are set forth. It should be understood that these examples are for illustrative purposes only and are not to be construed as limiting the scope of this invention in any manner.

Example 1

A perchloric acid tumor extract prepared from liver and colon cancer tissues was used to prepare polyclonal and monoclonal antibodies. The HAI test referred to as the Tennagen assay was developed solely using a polyclonal antibody and was used to diagnose colon cancer. An ELISA test using two specific monoclonal antibodies as capture antibodies and the polyclonal antibody as a signal generating antibody was developed later. A cocktail of the two specific monoclonal antibodies in the ELISA Assay repeatedly have a sensitivity of 95+% to Early Stage Colorectal carcinoma and a specificity of 94+% when serum samples from patients not known to have this condition are analyzed.

Immunohistochemical studies have shown the two monoclonal antibodies attach to the cell membranes of adenocarcinoma of colorectal cancer but do not attach to normal tissue. No attachment to cells in bladder or breast tissue is seen.

Materials and Methods

Immunization

Lots of several Tennessee Antigen (CA11-19), used in the immunization of goats for the production of polyclonal antibodies, were used to immunize the Balb/C mice for the production of the mouse hybridomas. The Tennessee Antigen (CA11-19) lots were perchloric acid extracts from adenocarcinoma tissue with purification steps including Sepharose 4B and Sephadex G200 chromatography as used for all antigen approved for immunization of goats and mice after the initial characterization of the antigen.

A large number of monoclonal antibodies were cloned from the hybridomas generated from three of the immunized mice. The hybridomas and monoclonals were initially screened using the approved Tennessee Antigen coated RBCs, a component of the TennaGen™ Assay. The hybridoma and monoclonal supernates were mixed with the Tennessee Antigen coated RBCs and hemagglutation titer was determined. Hybridoma and monoclonal cell culture supernates containing antibodies to Tennessee Antigen (CA11-19) resulted in the smooth mat agglutination. The HA assay was used as the screening test for screening large numbers of hybridomas and later monoclonal antibody production in cell culture supernates.

Using the Limiting Dilution technique, 23 monoclonal antibodies were produced from the best hybridomas. With extensive evaluation of the 23 clones, 7 clones were selected for further evaluation in the ELISA assay. Immunohistochemical studies confirmed the monoclonals would bind to adenocarcinoma of colon and lung. Two monoclonals also had positive staining with squamous cell and adenocarcinoma of the Lung. The negative controls were bladder and breast tissue. The final selection for the capture antibodies was a monoclonal cocktail utilizing 5E5-1 and 5A1-1 following the second blind serum panel from the National Cancer Institute. Summary of NCI evaluation using a Double Blinded Serum Panel supplied by the NCI through Mayo Clinic for the CA11-19 Mono-Poly ELISA Sandwich Assay is shown.

ELISA Assay

The ELISA uses a high binding microtiter plate coated with a cocktail of two mouse monoclonal antibodies, 5E5-1 & 5A1-1, the anti-Tennessee Antigen polyclonal antibody conjugated to alkaline phosphatase for use as the detection antibody and Tennessee Antigen lots approved for use as calibrators are calibrators in the CA11-19 ELISA Kit. The ELISA uses neat serum and not perchloric acid extracts.

The protocol for an ELISA is as follows:

Coating: each well of a high binding 96 well Easy Wash EIA/RIA plate was coated two hours at room temperature (~21° C.) followed by overnight at refrigeration (4-8° C.) with 125 uL of optimized by titration the solution of monoclonal cocktail (Capture Antibodies) in ELISA Coating Buffer. This equates to approximately 1 µg of antibody-per-well.

Blocking: after 3×300 µL washes with PBS T 20 Wash Buffer, the plates were blocked with 300 µL-per-well of 1.2% SEA Block in ELISA Coating Buffer for 2 hrs. At room temperature. Microtiter plate is further blocked with 2% Sucrose, and 4% Polyvinylpyrrolidone Buffer for 45 minutes.

Storage: Plates were dried by inverting on plastic drying racks for 24 hours at room temperature, then placed in foil pouches along with a dessicant packet and humidity indicator, and then stored at 40° C.

Sample: Plates, Calibrators and Sample Buffer were moved to room temperature and allowed to equilibrate. 25 µL of calibrators, and controls were added to the 2 microtiter wells of plates along with 25 µl of unknown samples followed by 75 uL of Sample Diluting Buffer. Plates were sealed, placed in ziplock bag and incubated at 37 degree C. overnight for 2 hrs.

CA11-19 plates were washed 6×300 µL with distilled water and then 100 uL of CA11-19 Polyclonal alkaline phosphatase conjugate was added to each well, Plates were sealed, placed in ziplock bag and left at 37 degree C. for 2 hrs.

CA11-19 plates were washed 6×300 µL with Distilled water and 100 uL CA11-19 Substrate was added to each well. Plates were placed at 37 degree C. for 30 min.

Measurement: The absorbance of each well at 405 nm was measured immediately using a standard plate reader.

Quantification: The absorbance of the standards was plotted using a point to point curve and the absorbance of the controls and unknowns are read against the curve.

The calibrators for the ELISA test are manufactured following SOP/Procedure using Tennessee Antigen (CA11-19) lots approved for use as a calibrator. The unitage is based on the original unitage of a vault reference standard and manufacturing allows for the dilution of antigen lot to obtain the standard required unitage. The Scientific advisory board at the FDA meeting made the statement that Tumor Markers were not pure enough to have a purified uniform standard. The World Health Organization made a similar statement concluding that the Tumor Marker Tests should be reported at "units/ml" and not in a weight such as ng or pc until the protein was completely 100% pure for a reference standard. Many tumor markers such as AFP, B-HCG, CA15-3, CA19-9, CA125, CA27-29, and PAP are reported as U/ml while CEA and PSA are reported in ng/ml.

Immunohistochemistry

The various monoclonal (cloned hybridomas) antibodies and goat antibody created for the TennaGen Assay were further characterized using Immunohistochemisty studies at two different independent facilities, Summa Medical, TX and U of Hawaii, HI. The monoclonal 5E5-1 and 5A1-1 stained adenocarcinoma of the colon and lung as well as squamous cell carcinoma of the lung just as the goat antisera; however, the signal from the 5E5-1 antibody was stronger.

Results

This test configuration was used to measure the CA11-19 levels in 422 patients. 222 samples were collected from GI Associates, TN) and 200 samples were purchased commercially from Equitech Bio, TX. The serum from these patients was assayed in the CA11-19 ELISA Assay. Results are summarized below in FIG. 1 and Tables 1, 2 and 3. With the use of the monoclonal cocktail of 5E5-1 and 5A1-1 along with improvements in other ELISA reagents, the sensitivity has been greater than 90% with specificity between 84 to 92% depending on the clinical status of the patient.

TABLE 1

All cancerous patients histologically confirmed categorized by cancer stage using a 6.5 units/mL cut-off to determine true positive, true negative, false positive, and false negative rates. Serum levels

| Colon Cancer/Histological confirmed | Number Samples | True Positive | True Negative | False Positive | False Negative |
|---|---|---|---|---|---|
| Stage I | 21 | 21(100%) | 0 | 0 | 0 |
| Stage II | 23 | 23(100%) | 0 | 0 | 0 |
| Stage III | 17 | 17(100%) | 0 | 0 | 0 |
| Stage IV | 11 | 7(64%) | 0 | 0 | 4(36%) |
| Unknown Stage (pathology report not-provided) | 9 | 9(100%) | 0 | 0 | 0 |

TABLE 2

Polyps considered to be precancerous-Tubular Adenoma, Adenoma malignancy and Villous Adenoma. Serum levels

| DIAGNOSIS POLYPS | Number Samples | True Positive | True Negative | False Positive | False Negative |
|---|---|---|---|---|---|
| Tubular Adenoma | 53 | 17(32%) | 0 | 0 | 36(68%) |
| Adenoma Malignancy | 1 | 1(100%) | 0 | 0 | 0 |
| Villous Adenoma | 1 | 1(100%) | 0 | 0 | 0 |
| Hyperplastic | 26 | 0 | 21(81%) | 5(19%) | 0 |
| Polyp-not classified | 13 | 0 | 12(92%) | 1(8%) | 0 |
| No Pathology | | | | | |

TABLE 3

All non-cancerous patients categorized by condition using a 6.5 units/mL cut-off to determine true positive, true negative, false positive, and false negative rates. Serum levels

| Condition | NumberSamples | TruePositive | TrueNegative | FalsePositive | FalseNegative |
|---|---|---|---|---|---|
| GI Bleeding | 36 | 0 | 27(75%) | 9(25%) | 0 |
| Crohns Disease | 10 | 0 | 8(80%) | 2(20%) | 0 |
| Diverticulitis | 70 | 0 | 62(89%) | 8(11%) | 0 |
| Ulcerative Colitis | 5 | 0 | 5(100%) | 0 | 0 |
| Hemorrhoids | 24 | 0 | 22(92%) | 2(8%) | 0 |
| Change in Bowel Habits | 20 | 0 | 13(65%) | 7(35%) | 0 |
| Normal GI | 73 | 0 | 66(90%) | 7(10%) | 0 |
| Misc GI Disease | 6 | 0 | 5(83%) | 1(17%) | 0 |
| Undiagnosed | 2 | 0 | 0 | 0 | 0 |

FIG. 1 shows a summary of all data from the 422 patient clinical study. Panel A shows the combined data for all non-cancerous and cancerous patients. The box covers the middle 50% of the data while the line is the median. The whiskers cover the middle 90% of the data (from 5% to 95%). Panel B is a receiver operator characteristic (ROC) curve comparing the cancerous vs. non-cancerous samples.

The box & whiskers plot (FIG. 1A) shows that the CA11-19 levels in non-cancerous tissues are lower overall than in cancerous patients. The box and whiskers plot comparing the levels of antigen detected in samples from patients known to have cancer as compared to control samples, establishes a cutoff value for 6.5 units/ml as indicative of the presence of colorectal cancer based on the lower limit of the whisker for the middle 90% of the data. When this data is plotted as a ROC curve (FIG. 1B), there is an apparent shift to the upper left quadrant consistent with a positive correlation between CA11-19 and cancer. The sensitivity and specificity of this test was 95% and 84% respectively when a cut-off of 6.5 units/mL is used. When the non-cancerous patients (Table 3) and cancerous patients (Table 1) are separated out by condition and the 6.5 units/mL cut-off is applied, the conditions giving the highest true positive, false positive, true negative, and false negative rate are seen. The highest false negative rate was seen in tubular adenomas (Table 2). Colon cancer from stages I-III gave 100% detection while stage IV was 64%.

Harvested monoclonal antibody supernates from 5E5-1 and 5A1-1 were purified and used in a cocktail as the capture antibody on high binding microtiter plates for further clinical evaluations. Two different Blind Serum Panels were assayed using two different lots of coated microtiter plates. The new lot used the 2012 cocktail as the capture antibody while the second lot used microtiter plates manufactured in 2009-2010 previously used in the evaluation conducted in 2009-2010. The serum panels were assembled at EDP Biotech and delivered to Dr. B. F. Overholt's office at Gastrointestinal Associates (GIA) where they were blind coded for assay. The CA11-19 (shown as CA1-18) assays were performed and results were taken to GIA where the codes were identified. The results are shown in Table 4 and 5.

TABLE 4

(Serum Panel A)

| | Disease Present | Disease Absent | Total Number |
|---|---|---|---|
| CA1-18 Elevated | 27 | 6 | 33 |
| CA1-18 Normal | 5 | 33 | 38 |
| TOTAL | 32 | 39 | 71 |

TABLE 5

(Serum Panel B)

| | Disease Present | Disease Absent | Total Number |
|---|---|---|---|
| CA1-18 Elevated | 21 | 11 | 32 |
| CA1-18 Normal | 1 | 29 | 30 |
| TOTAL | 22 | 40 | 62 |

Table 4 above compares Colorectal cancer and Normals confirmed by colonoscopy. Serum Panel A (Jul. 23, 2012) shows a Sensitivity of 84.4% and Specificity of 78.9%. Polyps and Lung Cancer not included in calculation. The CA11-19 Lot 2012 showed a sensitivity of 95.5% with specificity of 80.0 percent seen in Serum Panel B using the colorectal and benign GI data. Polyps and Lung Cancer not included in calculation. When data from Serum Panel A and B are combined, a sensitivity of 92.3% and specificity of 85% is seen in Stage I Colorectal cancer as compared to Benign GI Disease.

Discussion

These results show that an ELISA assay with two capture monoclonal antibodies and a detectably labeled polyclonal antibody prepared against the Tennessee antigen repeatedly have a sensitivity of 95+% to Early Stage Colorectal carcinoma and a specificity of 94+% as measured in serum.

Immunohistochemical studies have shown the two monoclonal antibodies attach to the cell membrane of adenocarcinoma of colorectal cancer but do not attach to normal tissue. No attachment to cells in bladder or breast tissue is seen.

Example 2

The identity of the antigen that is being detected by the antibody assays described above has been difficult to determine. The perchloric acid carcinoma cell extract CA11-19 contains a number of different proteins. Further purification of the perchloric acid extract has identified a fraction of about 60-65 kDa and a fraction of about 100 kDa. However, the 60-65 kDa fraction, when used to immunize animals, has not provided any antibodies that specifically detect early stage colorectal carcinoma.

Isolation and Characterization of Antigens Present in the CA11-19 Preparation.

Human adenocarcinoma tumor tissue from colon and liver were extracted. The purification procedure involved a perchloric acid extraction with further purification steps including Sepharose 4B® and Sephadex G200® chromatography. Following SOP guidelines, SDS gel, Western Blot, immunoelectrophoresis and antigen content/protein determinations were used for all antigen lots. Over 100 different tumor tissues were extracted into individual Tennessee Antigen (CA11-19) extract lots.

Amino Acid analysis, UV absorbance at 228 and Molecular Weight determinations have been repeatedly made of different antigen lots and compared to CEA. The results are shown in Table 6.

Similar characterizations were done comparing the 100 kDa antigen to the characteristics of alpha 1 anti-chymotrypsin (ACT), The results are shown in Table 7.

COMPARISON OF TENNESSEE ANTIGEN, ACT, and CEA

|  | CA1-18 | ACT | CEA |
| --- | --- | --- | --- |
| Molecular Weight | 100 kDa | 65 kDa | 180 kDa |
| UV Peak | 228 | 395 | 280 |
| Isoelectric Point | 3.5-4 | 5-5.3 | 3.5-4 |
| Globulin Region | Beta | Alpha | Beta |
| Cancer Site | GI-Lung | Prostate, Gastric | All Solid Tumors |
| Cancer Stage | EARLY | Advanced | Advanced |

SDS PAGE and Western Blot

Figure 2B:
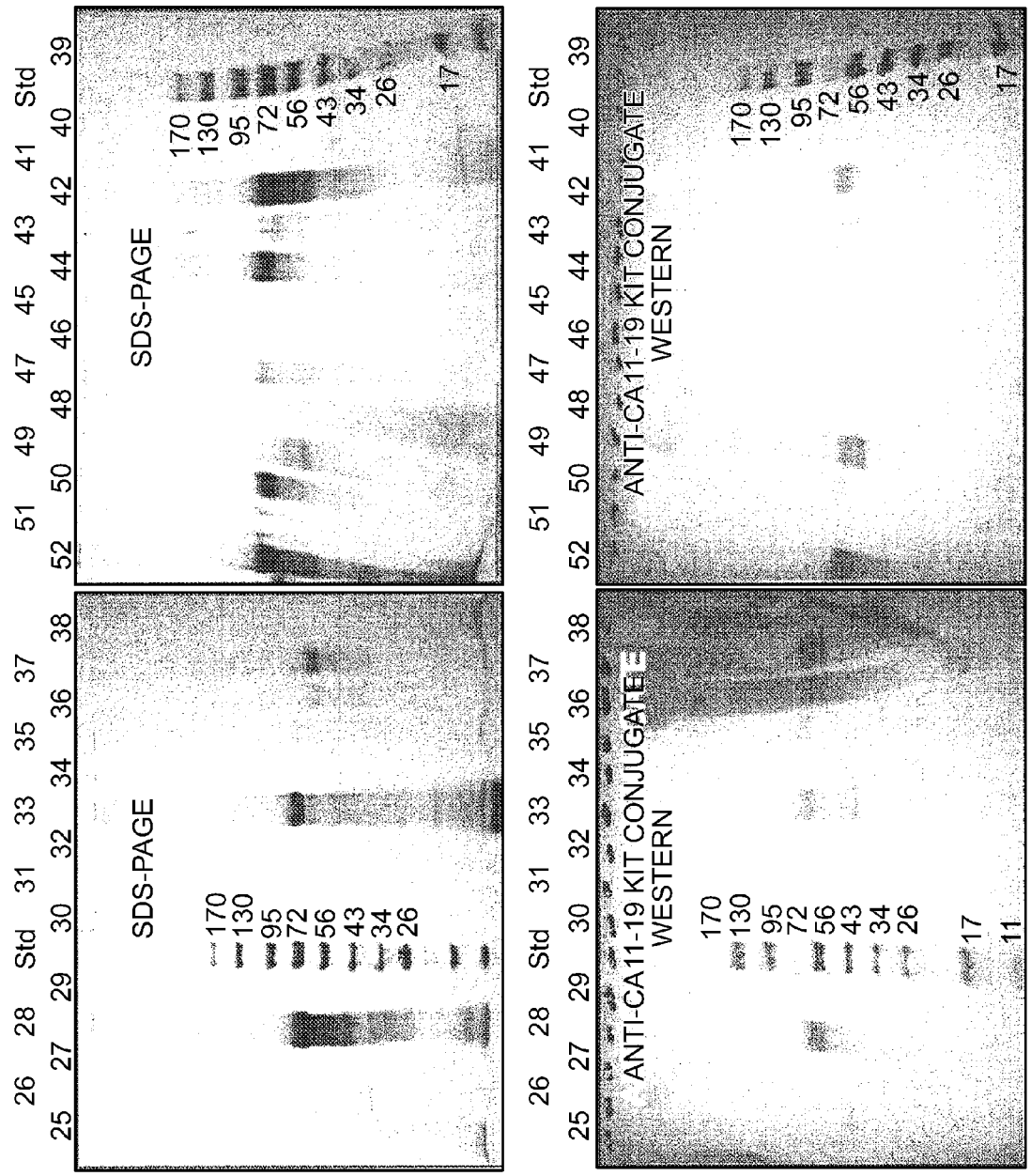
FIG. 2 shows SDS-PAGE and goat anti-CA11-19 polyclonal antibodies Conjugate Western of tumor and normal tissue perchloric acid extracts. CODES 1, 2, 7, 8, 15, 23, 25, 27, 32, 38, 39, 41, 42, 45, 50 are Normal Tissue Perchloric acid extracts. Panels A & B show the results of ~50 tumor extracts.

A large number of perchloric acid extracts of tumor and normal tissue were removed from −20° C. storage and sterile filtered. All the Tennessee Antigen and Normal tissue extracts were perchloric acid extract with no further purification. The Tennessee Antigen perchloric acid extract was more stable than the Tennessee Antigen Lots that had been further purified for use as immunogen and characterization work. These samples were screened for the presence of CA11-19 by SDS-PAGE separation (FIG. 2A) and then goat anti-CA11-19 polyclonal Conjugate Western in two different batches (FIG. 2B).

A subset of samples showed clean single band reactivity in the 55-76 kDa region while others showed a generic reactivity where the entire protein pool showed a streak in the Western. The only immunizing antigen (#19) available showed good Western reactivity as did another sample (#28) which was deemed reactive enough to be used for amino acid analysis. Selected samples showing a clean single band reactivity were rerun on SDS-PAGE with the goal of excising the Western reactive region for protein identification. 11 gel slices were removed and given to Protein Discovery. They digested the samples, sequenced the released peptides via mass spectrometry, and then probed available databases to determine the protein make-up of the gel slice. Interestingly, ACT was detected 3× more often than any other protein with albumin coming in second.

Discussion

The isolated fraction from colorectal and/or liver tumors has components with a molecular weight of 55 to 75 kDa

| TEST | TENNESSEE ANTIGEN(CA11-19) | 180 kDa CEA |
| --- | --- | --- |
| Molecular Weight | 100,000 Daltons | 200,000 Daltons |
| UV Absorbance | Peak @ 228 nm | Peak @ 280 nm |
| AMINO ACID STUDIES | | |
| Lysine content | GREATER (7.6 moles %) | Less (2.9 moles %) |
| Glutamic acid, Glycine, Alanine | More than CEA | Less Than TNAG |
| Aspartic acid, Serine, Valine, isoleucine | Less than CEA | Less than TN AG |
| Leucine | Less than CEA | More than TN AG |
| CARBOHYDRATE ANALYSIS | More than CEA's | Less than TN AG |
| Sialic Acid | 19.88 moles % (average) | 3.6 moles % (CEA WHO) |
| SDS Polyacrylamide | Band at 100,000 Daltons | No single band at 100,000 Daltons |
| Isoelectric Focusing | 3.5-4.0 range | 2.4, 3.0, 4.5-6.4 crude CEA prep 2.0-3.0 in purified prep |
| Immunoelectrophoresis/ Hemagglutination-inhibition | No cross reactivity with Gold's original CEA, Go's CEA, WHO-CEA, Egan CEA, or Roche CEA | | and a component with a 100 kDa. (FIG. 2A) The western blot shows reactivity with a 60 kDa and larger molecular weight proteins. (FIG. 2B). The identity of these bands was studied.

Very early data from two independent institutions showed that the Tennessee Antigen used as the immunogen for antibody production had a molecular weight close to 100 kDa. Two points important to the characterization studies: 1) the immunologically active portion of Tennessee Antigen has 100,000 molecular weight. Only the purified 100,000 MW material used as the immunogen has produced antibodies (monoclonal and polyclonal) that can measure a difference between Early Stage adenocarcinoma of colorectal and lung cancer serum with greater than 90% accuracy. The 60 kDa fraction used as the immunogen in rabbit, goat and mouse was not successful in producing a usable antibody. Further use of the 60 kDa material as the immunogen for antibody production in chicken and mouse also did not produce a useable antibody for the detection of colorectal and lung cancer when used as the capture antibody in a ELISA. The second significant point in the Tennessee Antigen Characterization is the documentation that Tennessee Antigen has a major UV peak at 228 and a small minor peak at 280 which is very different from Alpha 1 antichymotrypsin (ACT)-UV peak 395, and Alpha 1 antitrypsin-UV peak 296. Previous physical characterizations distinguish this band of material from 180 kDa CEA as well.

A total of 23 different monoclonal antibodies to Tennessee Antigen were produced, initially studied to be potentially useful and are stored in cryotanks for further evaluation for their diagnostic and therapeutic utility. Further immunohistochemical studies would identify the potential value of the additional 21 monoclonals to Tennessee Antigen. Experiments to further characterize the 100 kDa antigen involve amino acid sequencing of purified material and epitope mapping of the monoclonal antibodies.

Example 3

Separation of the 100 kDa material and the 60-65 kDa material Separation of high molecular weight material from low molecular weight material in adenocarcinoma tumor cell extracts in preparation for amino acid sequencing of large molecular weight fraction
Materials and Methods
Tumor Cell Material Two different tumor cell specimens were obtained from adenocarcinoma from colorectal tissue. One tumor cell specimen is a stage II adenocarcinoma identified as 167B-80. A second tumor cell specimen is also an adenocarcinoma stage II identified as 173-81. Control colorectal and tubular adenoma serum specimens are identified as HF numbers.
Tumor Cell Extraction Tumor cell extracts from each tumor cell specimen were prepared by mincing into very small pieces and extracting the material with 1.4% perchloric acid.
Column Chromatography Aqueous Perchloric acid extracts of each tumor cell extract were separated by column chromatography on Sepharose 4B. Fractions were collected and each fraction was tested for absorbance at 280 and in the ELISA assay. Fractions containing peak absorbance at 280 and ELISA activity were pooled and were further separated using Superdex 200 chromatography. Fractions were collected from Superdex 200 column and tested for absorbance at 280 and in the ELISA. Fractions were run on SDS polyacrylamide gel.
ELISA The ELISA uses a high binding microtiter plate coated with a cocktail of two mouse monoclonal antibodies, 5E5-1 and 5A1-1, the anti-Tennessee Antigen polyclonal antibody conjugated to alkaline phosphatase for use as the detection antibody. Large molecular weight and low molecular weight fractions from the column chromatography were tested in the ELISA assay for reactivity with the antibodies that can detect serum samples from patients having cancer.

The protocol for an ELISA is as follows:

Coating: each well of a high binding 96 well Easy Wash EIA/RIA plate was coated two hours at room temperature (~21° C.) followed by overnight at refrigeration (4-8° C.) with 125 uL of optimized by titration the solution of monoclonal cocktail (Capture Antibodies) in ELISA Coating Buffer. This equates to approximately 1 µg of antibody-per-well.

Blocking: after 3×300 µL washes with PBS T 20 Wash Buffer, the plates were blocked with 300 µL-per-well of 1.2% SEA Block in ELISA Coating Buffer for 2 hrs. at room temperature. Microtiter plate is further blocked with 2% Sucrose, and 4% Polyvinylpyrrolidone Buffer for 45 minutes.

Storage: Plates were dried by inverting on plastic drying racks for 24 hours at room temperature, then placed in foil pouches along with a dessicant packet and humidity indicator, and then stored at 40° C.

Sample: Plates, Calibrators and Sample Buffer were moved to room temperature and allowed to equilibrate. 25 µL of calibrators, and controls were added to the 2 microtiter wells of plates along with 25 µl of unknown samples followed by 75 uL of Sample Diluting Buffer. Plates were sealed, placed in ziplock bag and incubated at 37 degree C. overnight for 2 hrs.

CA11-19 plates were washed 6×300 µL with distilled water and then 100 uL of CA11-19 Polyclonal alkaline phosphatase conjugate was added to each well, Plates were sealed, placed in ziplock bag and left at 37 degree C. for 2 hrs.

CA11-19 plates were washed 6×300 µL with Distilled water and 100 uL CA11-19 Substrate was added to each well. Plates were placed at 37 degree C. for 30 min.

Measurement: The absorbance of each well at 405 nm was measured immediately using a standard plate reader.

Quantification: The absorbance of the standards was plotted using a point to point curve and the absorbance of the controls and unknowns are read against the curve.

The calibrators for the ELISA test were manufactured following SOP/Procedure using Tennessee Antigen (CA11-19) lots approved for use as a calibrator. The unitage was based on the original unitage of a vault reference standard and manufacturing allows for the dilution of antigen lot to obtain the standard required unitage.

Figure 3:
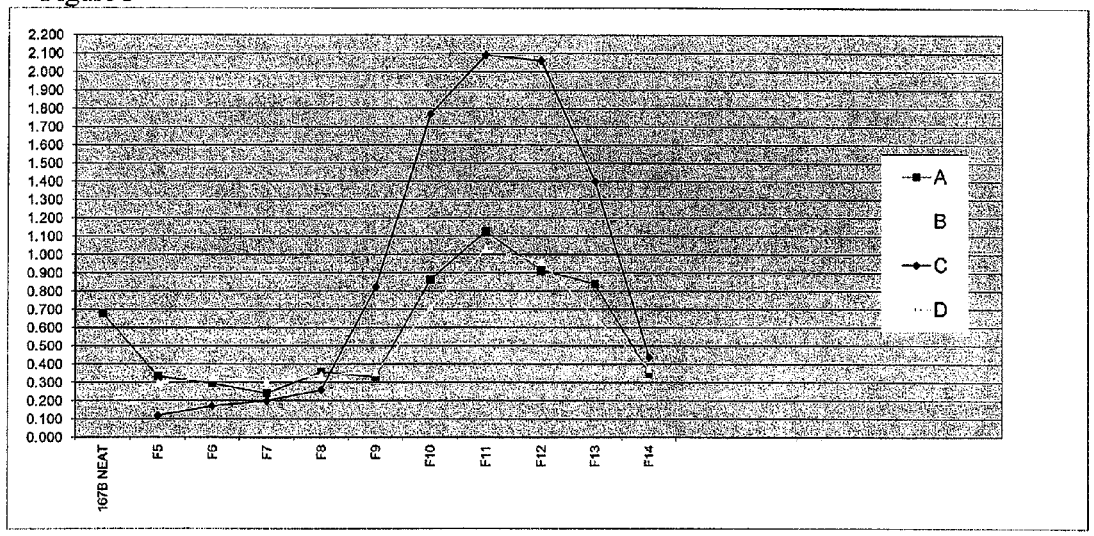
FIG. 3 shows fractionation of a perchloric acid extract of two separate colorectal tumor cell samples on Sepharose B. Absorbance at 280 for each sample is shown by (▲; ■) The fraction of one of the samples were also evaluated in the ELISA assay (♦).

The polyclonal antibody does not substantially bind to pools of human serum, 180 kDa CEA preparations or CEACAM 6 (NCA).
Results The results in FIG. 3 show that for each tumor cell extract bands of protein as determined by absorbance at 280 are found in fractions F9 to F13. The peak of the ELISA activity of the fractions indicate antigenic activity is predominantly found in fractions F10 to F12. Fractions F9 to F12 were pooled. The pooled fractions from each of the tumor specimens were then run on Superdex 200 column. (data not shown) A broad band of protein is found in fraction F7 to F13. Each fraction was tested in the ELISA and fractions showing peak activity were pooled and run on an SDS gel. A band was found at around 100 kDa (data not shown).

The band at 100 kDa will be analyzed further. The band will be cut out and analyzed for amino acid sequence.

Discussion

Previous studies have identified an antigen derived from tumor cell extracts detectable in a CA11-19 ELISA assay that is predictive of the presence of colorectal cancer in blood samples from patients. Characterization of the tumor cell extract revealed inactive protein fractions at 50-60 kDa and an active fraction at 100 kDa. In order to further characterize the 100 kDa fraction, separation and removal of the material having a molecular weight of 50-60 kDa was conducted. Separation of the lower molecular weight material from the higher molecular weight material was accomplished using column chromatography. Fractions that contained predominantly the 100 kDa material and that were active in the ELISA assay are being analyzed for amino acid sequence. This analysis should provide the identity of the antigen.

Example 4

N Glycan Profiling of CA11-19 Antigen

Figure 4:
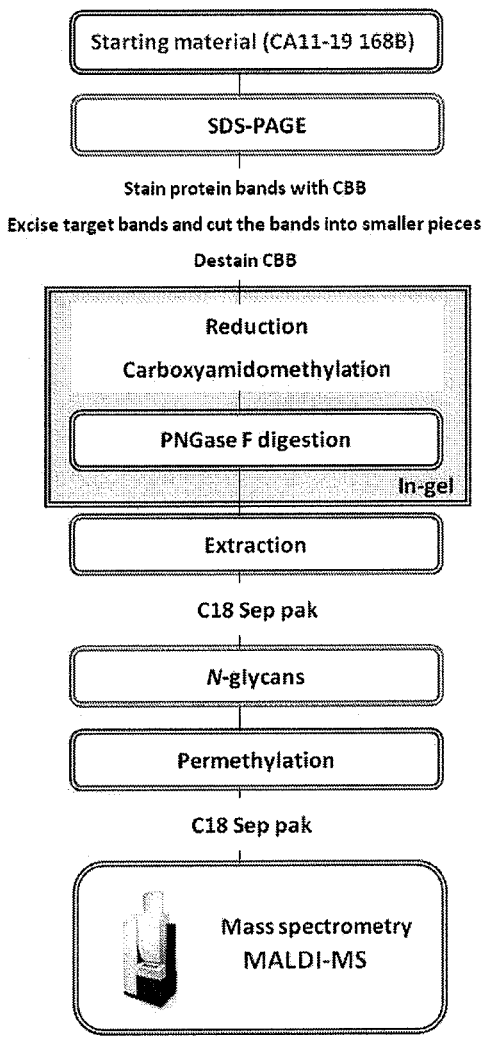
FIG. 4 shows methods for N-glycan profiling by MALDI-MS of glycoprotein 100 kDa obtained from an acid extract of a colon cancer cell.

The sample preparation methods for N-glycan profiling by MALDI-MS are summarized in FIG. 4.

SDS-PAGE

Figure 5:
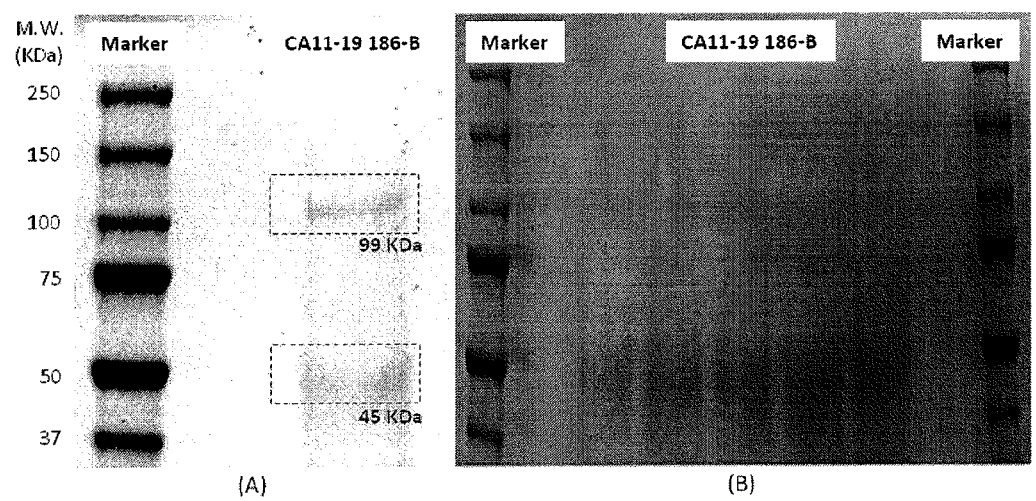
FIG. 5A shows localization of target glycoprotein 100 kDa band and an additional band at 45 kDa observed in the CA11-19 168B.
FIG. 5B shows pictures of actual gels used for sample analysis.

The 100 kDa CA11-19 material is referred to as 168B antigen and was prepared as described in Example 3. The sample was denatured by adding equal amounts of 2×SDS sample buffer and incubated at 100° C. for 5 min. The mixture then divided into small portions and loaded on each lane. The samples were separated in 7.5% SDS-PAGE gel. After electrophoresis, the resolved proteins were stained with Coomassie Brilliant Blue (CBB). (FIG. 5)

In-Gel PNGase F Digestion and Extraction of Released N-Glycans

In gel PNGase F digestion was performed according to the method of (Kuster et al Sequencing of N-linked oligosaccharides directly from protein gels: in-gel deglycosylation followed by matrix-assisted laser desorption/ionization mass spectrometry and normal-phase high performance liquid chromatography. *Anal. Biochem.*, (1997) 250, 82-101). Briefly, target glycoprotein bands were excised from CBB-stained gel sheet and the gel bands were further cut into smaller pieces. The gel pieces were then destained alternately with 50 mM ammonium bicarbonate (AmBic) and 100% acetonitrile until the color turned clear. Then proteins in gel were reduced with dithiothreitol (DTT), followed by carboxyamidomethylation with iodoacetamide (IAM). DTT and IAM in gel were washed out alternately with 50 mM AmBic and 100% acetonitrile. Dehydrated gel pieces were reswelled with PNGase F solution (PNGase F in 50 mM AmBic) on ice for 45 min initially, and then the digestion was carried out at 37° C. overnight. Released N-glycans were extracted from the gels by stepwise extraction increasing the proportion of acetonitrile in 5% formic acid. The extracts were dried.

N-Glycan Preparation

Released N-glycans were purified from peptides by passage through a Sep-Pak C18 cartridge. The glycan fraction was eluted with 5% acetic acid and dried by lyophilization. The fractions were dried by lyophilization then permethylated based on the method of Anumula and Taylor, (Anumula et al., A comprehensive procedure for preparation of partially methylated alditol acetates from glycoprotein carbohydrates. *Anal Biochem,* 1992. 203(1): p. 101-108.), prior to purification again with a C18 cartridge. The permethylated N-glycans were then analyzed with matrix-assisted laser desorption ionization-time of flight mass spectrometry (MALDI-TOF MS).

MALDI-TOF Analysis

MALDI/TOF-MS of the permethylated N-linked glycans was performed in the reflector positive ion mode using α-dihyroxybenzoic acid (DHBA, 20 mg/mL solution in 50% methanol) as a matrix. The spectrum was obtained by using AB Sciex TOF/TOF 5800 MADLI mass spectrometry system.

Results:

Separation of CA11-19 168B by SDS-PAGE

CA11-19 168B was separated by SDS-PAGE for in-gel digestion. After electrophoresis, the resolved proteins were stained with CBB and images of gels are shown in FIG. 5. FIG. 5A shows localization of target glycoprotein 100 KD band and an additional band at 45 KD observed in the CA11-19 168B. FIG. 5B shows pictures of actual gels used for your sample analysis. Since the 100 KD bands were not clearly visible to observe in FIG. 5B, we cut the region that corresponds to the molecular weight of 100 KD and were excised for N-glycan profiling. We also performed the N-glycan analysis on the 45 KD band with the same procedures as a reference.

N-Glycan Profiling by MALDI/TOF-MS

The permethylated N-glycans from samples provided were profiled by MALDI/TOF MS analysis. The MALDI-full mass spectra of each sample bands are shown in FIG. 6A-B.

In-gel digestion and N-glycan analysis from 100 KD bands reveals peaks that may correspond to several glycan structures (m/z 1416.6, m/z 1661.7, and m/z 2039.9). However, the intensity of peaks is almost same as the noise level because the trace amount of sample concentration (FIG. 6A). Although we can clearly detect glycan associated with the sample and they are biantennary structures with and without galactose, it is possible that we are not detecting all the glycans present due to lack of sufficient sensitivity from small amount of sample obtained for 100 kD band.

The primary structures that were detected in 45 kDa bands using MALDI/TOF-MS were complex type N-glycans such as GlcNAc1Man3GlcNAc2 (m/z 1416.6) and GlcNAc2Man3GlcNAc2 (m/z 1661.7). The complex type N-glycans with fucose were also observed in 45 kDa band (FIG. 6B). It should be noted that the relative peak intensities for these glycans were much higher than that of the 100 KD band.

A summary of all results following N-glycan profiling is shown in Table 8.

TABLE 8
Summary of N-glycans from the CA 11-19 168B detected by MALDI-MS. Gal(○), Galactose; Man(●), Mannose; Fuc(▼), Fucose; GlcNAc (■), N-acetylglucosamine;
| Suggested structure | Observed m/z : | 45 Kda | 100 Kda |
|---|---|---|---|
|  Man3GlcNAc2 | 1171.5 | ✓ | ✓ |
|  GlcNAc$_1$Man$_3$GlcNAc$_2$ | 1416.6 | ✓ | ✓ |
|  GlcNAc1Man3GlcNAc2Fuc1 | 1590.7 | | ✓ |
|  GlcNAc2Man3GlcNAc2 | 1661.7 | ✓ | ✓ |
| 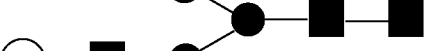 Gal1GlcNAc1Man3GlcNAc2Fuc1 | 1794.7 | | ✓ |
|  Gal1GlcNAc2Man3GlcNAc2 | 1865.8 | | ✓ |
|  GlcNAc3Man3GlcNAc2 | 1906.8 | | ✓ |

TABLE 8-continued

Summary of N-glycans from the CA 11-19 168B detected by MALDI-MS. Gal(○), Galactose; Man(●), Mannose; Fuc(▼), Fucose; GlcNAc (■), N-acetylglucosamine;

| Suggested structure | Observed m/z : | 45 Kda | 100 Kda |
|---|---|---|---|
| Gal1GlcNAc2Man3GlcNAc2Fuc1 | 2039.8 | ✓ | ✓ |
| Gal1GlcNAc2Man3GlcNAc2Fuc1 | 2069.8 |  | ✓ |
| Gal1GlcNAc3Man3GlcNAc2 | 2110.9 |  | ✓ |
| Gal1GlcNAc3Man3GlcNAc2Fuc1 | 2284.9 | ✓ | ✓ |
| Gal2GlcNAc3Man3GlcNAc2Fuc1 | 2489.0 |  | ✓ |

Discussion

N-glycan analysis from 100 KD bands indicates that peaks correspond to several glycan structures as shown in Table 8. In the SDS-PAGE (FIG. 5), we could definitely see the difference between the concentration of 45 KDa bands and 100 KDa. Consequently, we were able to observe much stronger signals from the 45 KD band as compared to the 100 KD band.

Example 5

O Glycan Profiling of CA11-19

Figure 7:
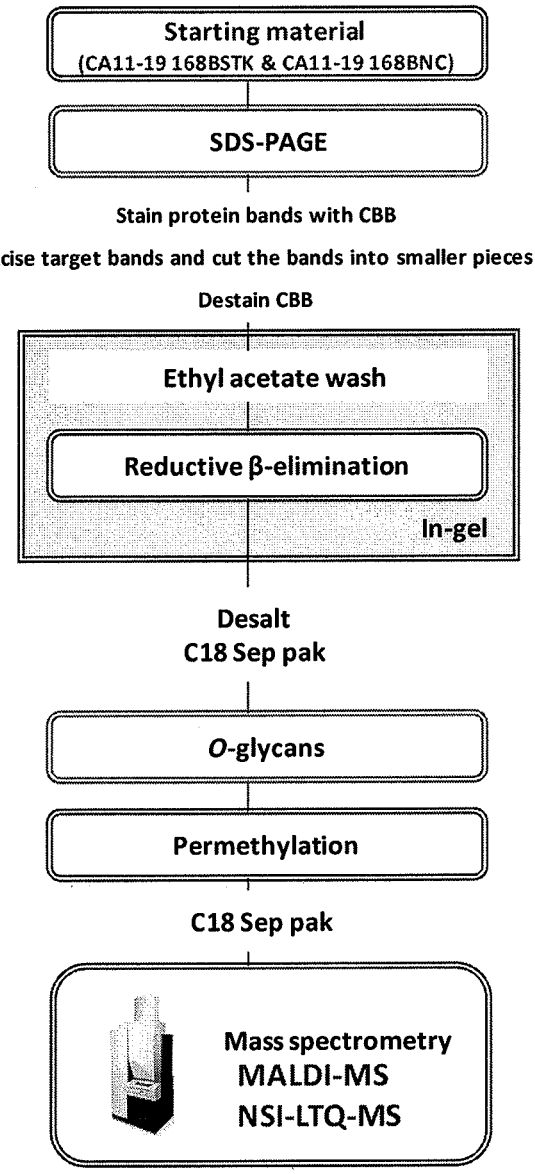
FIG. 7 shows the sample preparation methods for O-glycan profiling by MALDI-MS.

The sample preparation methods for O-glycan profiling by MALDI-MS are summarized in FIG. 7.

SDS-PAGE

Sample material CA11-19BSTK and CA11-19 168BNC were prepared as described in Example 3. Sample STK differed from NC by being concentrated 5 fold. The samples were denatured by adding equal amounts of 2×SDS sample buffer and incubated at 100° C. for 5 min. Then the mixture was divided into small portions and loaded on each lane. The samples were separated in 7.5% SDS-PAGE gel. After electrophoresis, the resolved proteins were stained with Coomassie Brilliant Blue (CBB).

In-Gel O-Glycan Release by Reductive β-Elimination

In gel reductive β-elimination was performed according to the method of Dell, A et al (Dell, A. et al. Mass spectrometry of Carbohydrate-Containing Biopolymers. *Methods Enzymol.*, (1994) 230, 108-132.) Briefly, target glycoprotein bands were excised from CBB-stained gel sheet and the gel bands were further cut into smaller pieces. The gel pieces were then destained alternately with 50 mM ammonium bicarbonate (AmBic) and 100% acetonitrile until the color turned clear. And then, gel pieces were washed with ethyl acetate and were washed with acetonitrile. O-glycans were released from gels by β-elimination. The gels were rehydrated by adding 100 mM sodium hydroxide and 1M sodium borohydrate. The samples were incubated for 18 h at 45° C. The sample was placed on ice and neutralized with 10% acetic acid. The neutralized samples were loaded onto AG-50WX8 cation exchange column to desalt. Ten percent acetic acid in methanol was added to samples to remove the borate.

O-Glycan Preparation

Released O-glycans were purified from peptides by passage through a Sep-Pak C18 cartridge. The glycan fraction was eluted with 5% acetic acid and dried by lyophilization. The fractions were dried by lyophilization then permethylated based on the method of Anumula and Taylor (cited supra), prior to purification again with a C18 cartridge. The permethylated O-glycan were then analyzed with matrix-assisted laser desorption ionization-time of flight mass spectrometry (MALDI-TOF MS).

MALDI-TOF Analysis

MALDI/TOF-MS of the permethylated N-linked glycans was performed in the reflector positive ion mode using α-dihyroxybenzoic acid (DHBA, 20 mg/mL solution in 50% methanol) as a matrix. The spectrum was obtained by using AB Sciex TOF/TOF 5800 MADLI mass spectrometry system.

Nanospray Ionization FTMS

NSI-MSMS analysis was determined using a LTQ Orbitrap XL mass spectrometer (ThermoFisher) equipped with a nanospray ion source. Permethylated O-linked glycans were dissolved in 1 mM NaOH in 50% methanol then infused directly into the instrument at a constant flow rate of 0.5 μL/min. A full FTMS spectrum was collected at 30 000 resolution with 3 microscans. The capillary temperature was set at 210° C. and MS analysis was performed in the positive ion mode. For total ion mapping (automated MS/MS analysis), m/z range, 500 to 2000 was scanned with ITMS mode in successive 2 mass unit windows.

Results:

Separation of CA11-19 168BSTK and CA11-19 168BNC by SDS-PAGE

Figure 8:
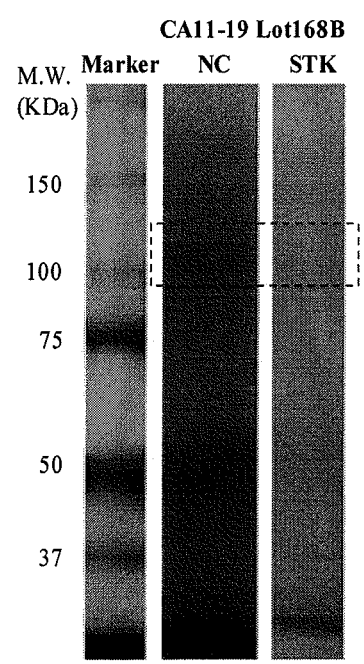
FIG. 8 shows CA11-19 168BNC and CA11-19 168BSTK separated by SDS-PAGE for in-gel digestion.

CA11-19 168BNC and CA11-19 168BSTK were separated by SDS-PAGE for in-gel digestion. See FIG. 8. After electrophoresis, the gels were stained with CBB. FIG. 8 shows the localization of target glycoprotein 100 KDa of CA11-19 168BNC and CA11-19 168BSTK. Since the 100 kDa band of CA 11-19 168BSTK was not clearly visible to observe in FIG. 8, the gel was cut the region that corresponds to the molecular weight of 100 KDa and gel slices excised for O-glycan profiling.

O-Glycan Profiling by MALDI/TOF-MS

Permethylated O-glycans from the sample were analyzed by MALDI/TOF MS as well as NSI-MS and total ion mapping.

Figure 9:
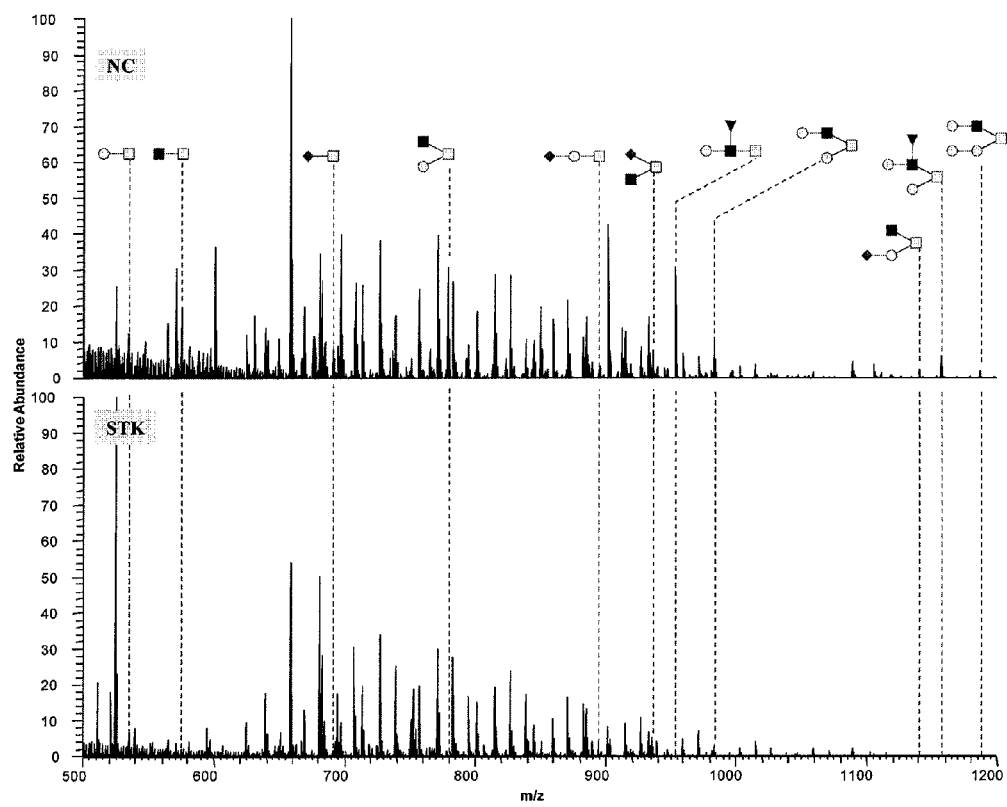
FIG. 9 shows NSI-FTMS spectra of O-glycan from the 100 kDa band from the both samples.

The MALDI-TOF-full mass spectra of 100 KDa sample bands in both samples are not shown in this report because MALDI-TOF analysis did not reveal major glycan signals but instead presented mostly non-glycan signals. The samples were further analyzed with a LTQ Orbitrap XL mass spectrometer. The full FTMS scan of the sample show similar results as MALDI-TOF analysis with some O-glycan signals. NSI-FTMS spectra of O-glycan from the 100 KDa band from the both samples are shown in FIG. 9. The upper spectrum presents O-glycans of CA11-19 168BNC(A) and the lower spectrum shows O-glycans of CA11-19 168BSTK (B). The major O-glycan structures are the core 2 structure (m/z 779) and the core3 with fucose (m/z 953). In the SDS-PAGE (FIG. 8), we could definitely see the difference of sample concentration between CA11-19 168BNC and CA11-19 168BSTK. Consequentially, we did not observe the strong O-glycan signals from sample CA11-19 168BNC in sample CA11-19 168BSTK.

To confirm the O-glycan structures, total ion mapping (TIM) was carried out by NSI LTQ Orbitrap XL MS. Using TIM scan method, we were able to confirm several O-glycans which is summarized in Table 9. Both analyses showed a similar trend. CA11-19 168BNC sample shows clearer MSMS spectra than CA 11-19 168BSTK sample because of the sample concentration.

Figure 10:
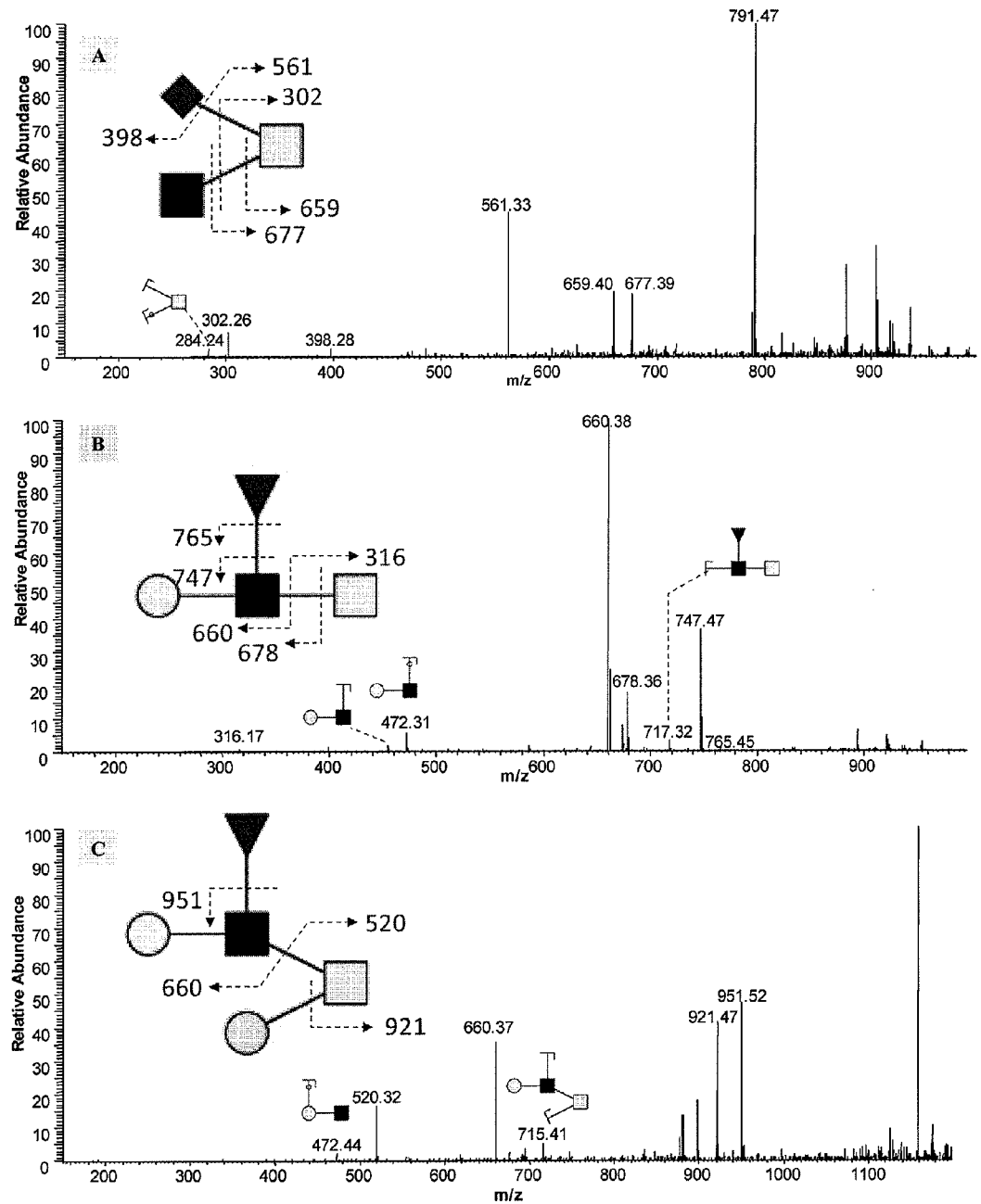
FIG. 10 A) The MSMS spectra of the permethylated O-glycan at m/z 936, m/z 953, and m/z 1157 derived from the O-glycan spectrum of CA 11-19 168BNC (FIG. 10 upper spectrum). The MSMS profile of the molecular ion at m/z 936 (NeuAc-HexNAc-HexNAc), the diagnostic b ion is shown at m/z 398, together with the complementary y ions at m/z 561, m/z 659, and m/z 677.

The MSMS spectra of the permethylated O-glycan at m/z 936, m/z 953, and m/z 1157 derived from the O-glycan spectrum of CA 11-19 168BNC (FIG. 9 upper spectrum) are shown in FIG. 10 as examples. As explained in FIG. 10A, MSMS profile of the molecular ion at m/z 936 (NeuAc-HexNAc-HexNAc), the diagnostic b ion is shown at m/z 398, together with the complementary y ions at m/z 561, m/z 659, and m/z 677. The MSMS profile of the molecular ion at m/z 953 (Hex-DHex-HexNAc2) and m/z 1157 (Hex2-DHex-HexNAc2) are interpreted in FIGS. 10B and 10C.

The MSMS profile of CA 11-19 168BNC and CA 11-19 168BSTK showed the same patterns and we present spectra from CA 11-19 168BNC in this report.

TABLE 9

Summary of O-glycans from the CA11-19 168B glycoproteins

| Structural assignment | Theoretical m/z | Observed m/z | NC | STK |
|---|---|---|---|---|
| 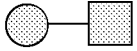<br>Hex-HexNAc | 534.29 | 534.29 | ✓ | — |
| <br>HexNAc2 | 575.32 | 575.32 | ✓ | ✓ |
| <br>NeuAc-HexNAc | 691.36 | 691.37 | ✓ | — |
| <br>Hex-HexNAc2 | 779.41 | 779.42 | ✓ | ✓ |
| <br>NeuAc-Hex-HexNAc | 895.46 | 895.47 | ✓ | ✓ |
| 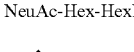<br>Neu-Ac-HexNAc2 | 936.49 | 936.50 | ✓ | ✓ |

TABLE 9-continued

Summary of O-glycans from the CA11-19 168B glycoproteins

| Structural assignment | Theoretical m/z | Observed m/z | NC | STK |
|---|---|---|---|---|
| Hex-DHex-HexNAc2 | 953.51 | 953.50 | ✓ | ✓ |
| Hex2-HexNAc2 | 983.51 | 983.52 | ✓ | ✓ |
| NeuAc-Hex-HexNAc2 | 1140.59 | 1140.60 | ✓ | — |
| Hex2-DHex-HexNAc2 | 1157.60 | 1157.61 | ✓ | ✓ |
| Hex3-HexNAc2 | 1187.61 | 1187.63 | ✓ | — |

Discussion

Our results indicate that the major O-linked glycans from CA11-19 168BNC and CA11-19 168BSTK are the core 2 structure (m/z 779) and the core3 with fucose (m/z 953). Since the amount of CA11-19 168BSTK glycoprotein was smaller than CA11-19 168BNC, the full ms of CA11-19 168BNC showed more O-glycan signals. It is being noted that the assigned glycan structures in the current report are based on common biosynthetic pathways.

Example 6

Amino Acid Sequence of 100 kDa Material

The 100 kDa (168B0 material was isolated and analyzed for amino acid sequence.

Amino Acid Sequence Analysis

One sample (in solution) was received. The proteins were reduced, alkylated, and digested with trypsin using the FASP protocol. The sample was resuspended in 2% acetonitrile/ 0.1% formic acid and analysis by LC-ESI-MS/MS. A 120 min. gradient was used and MS analysis was performed with an LTQ Orbitrap Velos mass spectrometer. MS spectra were searched using the MASCOT algorithm and the results generated an Excel spreadsheet. Searches using the tryptic peptides were conducted against a Human uniprot database. The protein was identified as having a sequence of CEACAM5 isofrom 2 (SEQ ID NO:1).

Peptide Mass Fingerprint of Antigen 168B

In order to characterize the antigen 168B, we submitted the sample to trypsin, chymotrypsin and ASP-N proteolysis followed by LC-LTQ Orbitrap MS/MS analysis. For the characterization of the antigen, a nano-LC chromatography was processed using a Ultimate 3000 (Dionex) system in line with a LTQ Orbitrap XL mass spectrometer (Thermo).

Sample Preparation:

5 µl of the antigen (2.5 µM) was mixed with 20 µl of ammonium bicarbonate (25 mM, pH 8.3). After mixing 2.5 µl of DTT (500 mM) is added to the solution. The mixture was then incubated 1 hour at 55° C. After incubation, 2.5 µl of iodioacetamide (1M) is added before 1 hour of incubation at room temperature in a dark room. After incubation, the solution is diluted 1/5 by adding 120 µl of the buffer used for the proteolysis.

145 µl of the reduced/alkyled antigen was mixed with 2 µl of trypsin (Roche Diagnostic) at ratio 1/20. The proteolytic mixture was incubated overnight at 37° C.

145 µl of the reduced/alkyled antigen was mixed with 2 µl of chymotrypsin (Roche Diagnostic) at ratio 1/20. The proteolytic mixture was incubated overnight at 30° C.

145 µl of the reduced/alkyled antigen was mixed with 2 µl of ASP-N(Roche Diagnostic) at ratio 1/20. The proteolytic mixture was incubated overnight at 30° C.

After proteolysis, 10 µl of the peptide generated by proteolysis was loaded onto a nano-liquid chromatography system (Ultimate 3000, Dionex).

A 95/05/0.1 H2O/ACN/HCOOH v/v/v
B 20/80/0.1 H2O/ACN/HCOOH v/v/v
gradient 5-40% B in 35 minutes
injected volume 10 µl
precolumn 300-µm ID×5-mm C4 PepMapTM
precolumn flow rate 30 µl/min
column 75-µm ID×5-cm C4 PepMapTM
column flow rate 200 nl/min The LTQ orbitrap MS analysis has been performed with the following parameters:

| | |
|---|---|
| needle voltage | 1.8 V |
| capillary voltage | 5 V |
| µscan MS | 1 |
| µscan MS2 | 1 |
| MS range m/z | 300-1700 |
| MS/MS strategy | MS + 6CID MS/MS |
| Min. signal required | 500 |
| Ion isolation window | 3 m/z units |
| Normalized collision energy | 35% |
| Default charge state | 2 |
| Activation Q | 0.25 |
| Activation time | 30 |
| Dynamic exclusion | ON |
| Dynamic exclusion params | RC 1, RD 30s, ED 30s |
| Charge state screening | ON |
| Charge state rejection | ON |
| Charge state reject. Params | +1 and unassigned rejected |

Validation Filters
Peptide Delta CN≥0.1
Peptide Xcorrvs Charge state≥1.5 (+1), 2.00(+2), 2.50(+3), 3.00(≥+4)
Peptide Probability≤0.001

Peptide Matches=1
Protein Number of Different Peptides≥2
Protein Exclude this reference: Keratin
Results The sequence of CEACAM5 isoform 2 was used to analyze the mass spec data of the tryptic peptides. 18 tryptic peptides were identified in the sequence of 168B, covering 29.8%:

Identified Tryptic peptides of 168B

| Peptide | MH+ | Position | Significance | SEQ ID NO |
|---|---|---|---|---|
| MESPSAPPHR | 1108.52 | 1-10 | 94.9 | 40 |
| WCIPWQR | 988.48 | 11-18 | 95.7 | 41 |
| LLLTASLLTFWNPPTTAK | 1987.12 | 18-35 | 96.8 | 42 |
| VDGNR | 560.27 | 73-77 | 95.9 | 43 |
| QIIGYVIGTQQATPGPAYSGR | 2177.13 | 78-98 | 92.4 | 44 |
| SDLVNEEATGQFR | 1465.69 | 127-139 | 95.8 | 45 |
| VYPELPKPSISSNNSKPVEDK | 2328.2 | 140-160 | 94.6 | 46 |
| LQLSNGNR | 901.48 | 191-198 | 99.2 | 47 |
| TLTLFNVTR | 1064.6 | 199-207 | 97.1 | 48 |
| NDTASYK | 798.36 | 208-214 | 98.9 | 49 |
| CETQNPVSAR | 1104.51 | 215-224 | 93.6 | 50 |
| LQLSNDNR | 959.49 | 368-375 | 98.5 | 51 |
| TLTLLSVTR | 1003.61 | 376-384 | 92.2 | 52 |
| NSGLYTCQANNSASGHSR | 1866.81 | 470-487 | 97.2 | 53 |
| AYVCGIQNSVSANR | 1481.71 | 567-580 | 92.5 | 54 |
| INGIPQQHTQVLFIAK | 1807.02 | 628-643 | 95.3 | 55 |
| ITPNNNGTYACFVSNLATGR | 2113.01 | 644-663 | 95.1 | 56 |
| NNSIVK | 674.38 | 664-669 | 96.5 | 57 |

The sequence of CEACAM5 isoform 2 was used to analyze the mass spec data of the chymotryptic peptides. 35 chymotryptic peptides were identified in the sequence of B168, covering 65.3%:

Identified Chymotrypsin peptides of 168B

| Peptide | MH+ | Position | Significance | SEQ ID NO |
|---|---|---|---|---|
| ESPSAPPHRW | 1163.55 | 2-11 | 92.5 | 58 |
| ESTPFNVAEGKEVLLLVHNL | 2209.5 | 39-58 | 94.4 | 59 |
| HLFGYSWYK | 1199.56 | 61-69 | 96.5 | 60 |
| KGERVDGNRQIIGY | 1604.85 | 69-82 | 90.3 | 61 |
| VIGTQQATPGPAY | 1302.66 | 83-95 | 94.5 | 62 |
| SGREIIYPNASL | 1319.69 | 96-107 | 96.6 | 63 |
| IQNIIQNDTGF | 1262.63 | 109-119 | 97 | 64 |
| VNEEATGQF | 994.44 | 130-138 | 92.3 | 65 |
| TCEPETQDATY | 1257.49 | 166-176 | 93.5 | 66 |
| VNNQSLPVSPRL | 1323.73 | 180-191 | 94 | 67 |
| NVTRNDTASY | 1140.52 | 204-213 | 96.1 | 68 |
| TISPLNTSYRSGENLNL | 1877.93 | 241-257 | 98.1 | 69 |
| SCHAASNPPAQY | 1245.53 | 258-269 | 94.3 | 70 |
| IPNITVNNSGSY | 1278.63 | 286-297 | 93.6 | 71 |
| TCQAHNSDTGL | 1146.48 | 298-308 | 90.5 | 72 |
| NRTTVTTITVY | 1268.68 | 309-319 | 92.8 | 73 |
| ITSNNSNPVEDEDAVAL | 1787.82 | 326-342 | 96.5 | 74 |
| TCEPEIQNTTY | 1298.55 | 343-353 | 97.6 | 75 |
| SVTRNDVGPYECGIQNEL | 1993.92 | 381-398 | 92.6 | 76 |
| SVDHSDPVIL | 1081.55 | 399-408 | 93.3 | 77 |
| GPDDPTISPSY | 1148.51 | 413-423 | 94.5 | 78 |
| YRPGVNLSLSCHAASNPPAQYS | 2331.09 | 426-447 | 96.3 | 79 |
| IDENIQQHTQEL | 1467.7 | 450-461 | 91.5 | 80 |
| ISNITEKNSGL | 1175.62 | 463-473 | 92.5 | 81 |
| VKTITVSAELPKPSISSNNSKP | 2296.25 | 490-511 | 93.8 | 82 |
| TCEPEAQNTTY | 1256.5 | 521-531 | 94.5 | 83 |
| VNGQSLPVSPRL | 1266.71 | 535-546 | 96.2 | 84 |
| NVTRNDARAY | 1179.58 | 559-568 | 98.1 | 85 |
| VCGIQNSVSANRSDPVTL | 1859.92 | 569-586 | 95.6 | 86 |
| GPDTPIISPPDSSY | 1445.67 | 591-604 | 95.6 | 87 |
| SCHSASNPSPQY | 1277.52 | 613-624 | 90.5 | 88 |
| RINGIPQQHTQVL | 1503.83 | 627-639 | 90.6 | 89 |
| IAKITPNNNGTY | 1305.67 | 641-652 | 92.2 | 90 |
| SGTSPGLSAGAT | 1004.46 | 676-687 | 94.8 | 91 |
| ATVGIMIGVLVGVA | 1298.75 | 686-699 | 96.2 | 92 |

9 peptides were identified by Asp N proteolysis in the sequence of B168, covering 16.8%:

Identified ASP-N peptides of 168B

| Peptide | MH+ | Position | Significance | SEQ ID NO |
|---|---|---|---|---|
| DTGFYTLHVIKS | 1380.7158 | 116-127 | 94.5 | 93 |
| DAVAFTCEPETQ | 1310.5569 | 161-172 | 96.2 | 94 |
| DTASYKCETQNPVSARRS | 2012.9454 | 209-226 | 92.5 | 95 |
| DSVILNVLYGP | 1189.6463 | 227-237 | 94.7 | 96 |
| DNRTLTLLSVTRN | 1502.8285 | 373-385 | 92 | 97 |
| DVGPYECGIQNELSV | 1622.7366 | 386-400 | 98.6 | 98 |
| DPVILNVLYGP | 1199.667 | 404-414 | 93.3 | 99 |
| DARAYVCGIQNSVSANRS | 1910.9137 | 564-581 | 95.7 | 100 |
| DTPIISPP | 839.4509 | 593-600 | 96.1 | 101 |

Based on the results obtained, we designed overlap mapping of the trypsin, chymotrypsin and ASP-N peptides (FIG. 14). Combining the peptides of Trypsin, Chymotrypsin and ASP-N proteolysis, 85.6% of the sequence is covered. The polypeptide is identified as CEACAM5 isoform 2 as shown in FIG. 14 (SEQ ID NO:1)

Example 7

Antibody Characterization: Mass Spectroscopy of Antibodies Cross-Linked with Antigen Sample Preparation Samples provided included Antibody 1 5E5-1: 0.2 mg/ml; 2 ml; glycine buffer; Antibody 2 5A1-1: 1.2 mg/ml; 2 ml; glycine buffer; and Antigen 168B: 0.8 mg/ml; 100 µl; PBS pH 7.4. Antibody 5E5 and Antibody 5A1-1 have been shown to identify a biomarker for colorectal cancer in serum from patients. The antigen is identified as 168B and is a partially glycosylated form of CEACAM5 as described herein.

Three mAb/Ag interactions samples were prepared with the following concentrations:

A Antigen: 168B Antibody: 5E5-1 Mix 168B/5E5-1

5 microliters of the antigen (4 micromolar) were mixed with 5 microliters of antibody (2 micromolar) to form a mixture of 10 microliter (2 micromolar antigen and 1 micromolar antibody)

B Antigen: 168B Antibody: 5A1-1 Mix 168B/5A1-1

5 microliters of the antigen (4 micromolar) were mixed with 5 microliters of antibody (2 micromolar) to form a mixture of 10 microliter (2 micromolar antigen and 1 micromolar antibody)

C Antigen: 168B Antibody: 5A1-1/5E5-1 Mix 168B/5A1-1/5E5-1

5 microliters of the antigen (4 micromolar) were mixed with 2 microliters of each antibody (2 micromolar) to form a mixture of 10 microliter (2 micromolar antigen/1 micromolar antibody5A1-1/1 micromolar antibody 5E5-1)

1 µl of the mixture obtained was mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample was spotted on the MALDI plate (SCOUT 384). After crystallization at room temperature, the plate was introduced in the MALDI mass spectrometer and analyzed immediately. The analysis has been repeated in triplicate.

Cross-Link Experiments

The mixtures prepared above (9 µl left for each mixture) was submitted to cross-linking using CovalX's K200 MALDI MS analysis kit. 9 µl of the mixture was mixed with 1 µl of K200 Stabilizer reagent (2 mg/ml) and incubated at room temperature. CovalX uses a mixture of amine based crosslinking agents to stabilize the interactions between the antibody and the antigen. After the incubation time (180 minutes), the samples were prepared for MALDI analysis. The samples were analyzed by High-Mass MALDI analysis immediately after crystallization.

High-Mass MALDI MS Analysis

The MALDI ToF MS analysis has been performed using CovalX's HM3 interaction module with a standard nitrogen laser and focusing on different mass ranges from 0 to 2000 kDa. For the analysis, the following parameters have been applied:

Mass Spectrometer:
Linear and Positive mode
Ion Source 1: 20 kV
Ion Source 2: 17 kV
Lens: 12 kV
Pulse Ion Extraction: 400 ns
HM3:
Gain Voltage: 3.14 kV
Acceleration Voltage: 20 kV To calibrate the instrument, an external calibration with clusters of Insulin, BSA and IgG has been applied. For each sample, 3 spots were analyzed (300 laser shots per spots). The presented spectrum corresponds to the sum of 300 laser shots. The MS data were analyzed using CovalX's Complex Tracker analysis software version 2.0.

Results

Figure 11A:
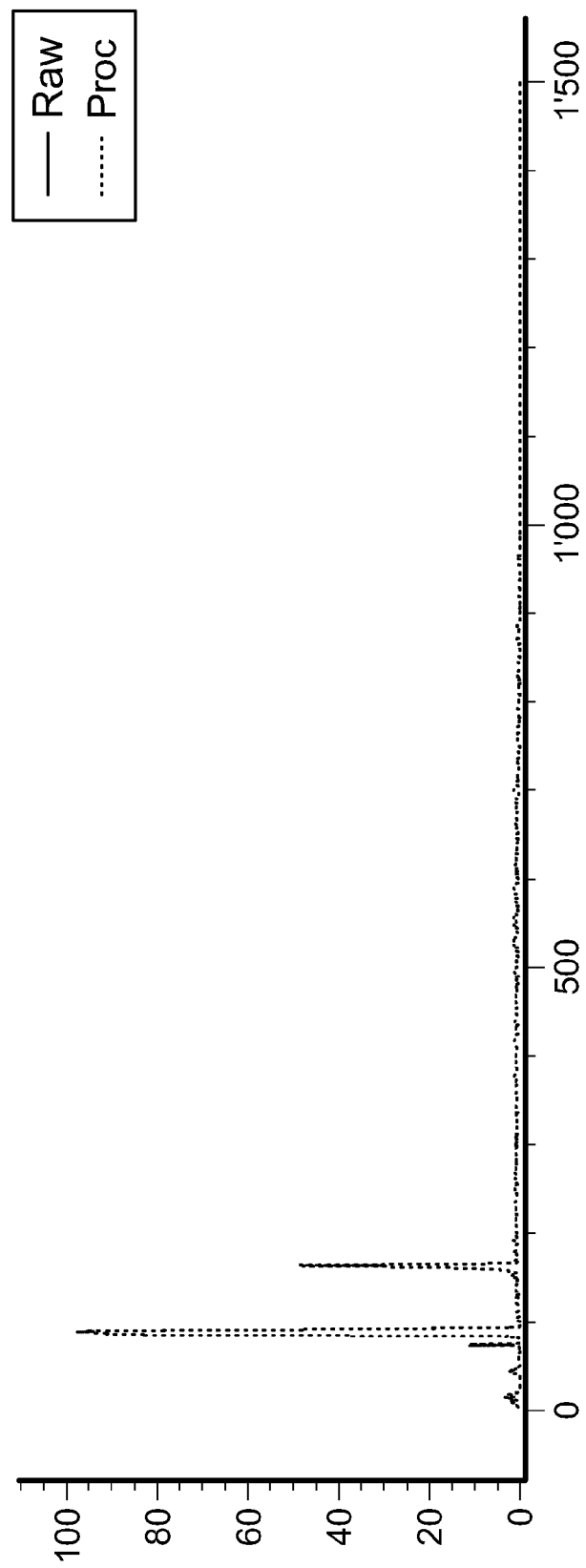
FIG. 11A) Analysis of the mix A: 5E5-1/168B, showed that the antigen and the antibody were detected with observed MH+=92.879 kDa (168B-antigen) and MH+=158.498 kDa. (5E5-1 antibody)
Figure 11B:
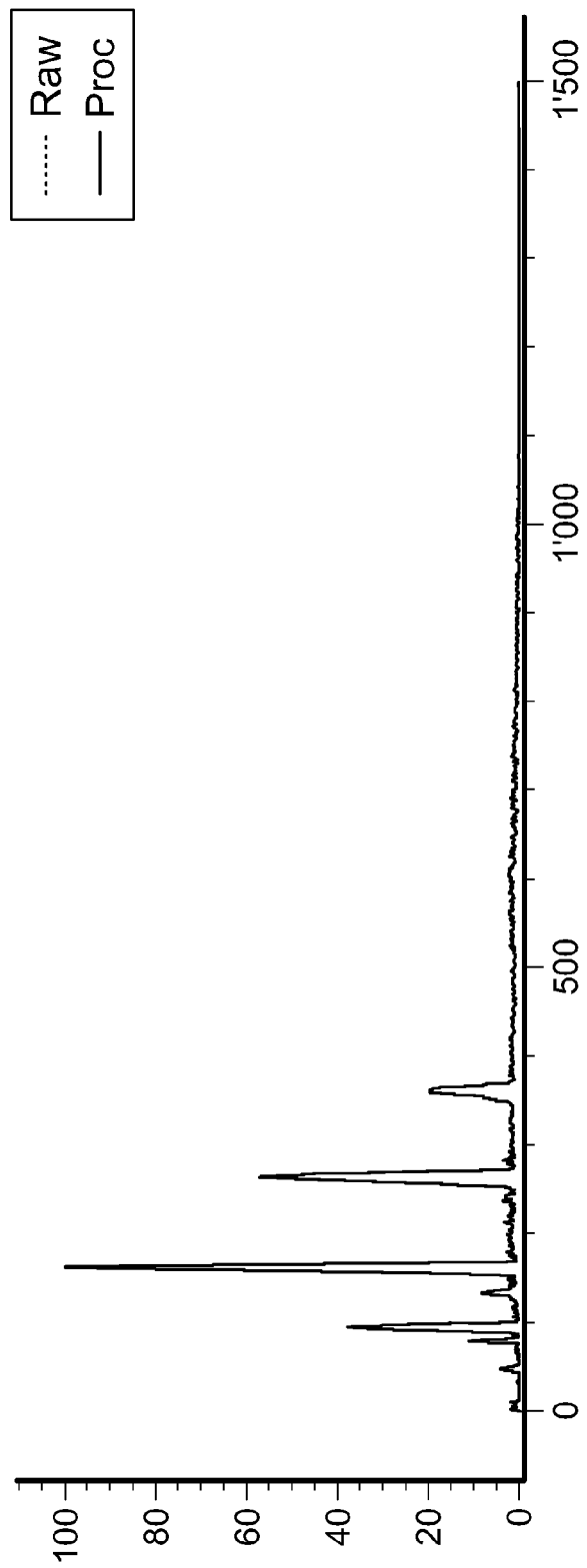
FIG. 11B) The cross-linking experiment was completed after 180 minutes incubation time with the crosslinking reagent K200. After cross-linking, we detected two additional peaks with MH+=258.945 kDa [5E5-1•B168] and MH+=354.164 kDa [5E5-1•2B168].
Figure 11C:
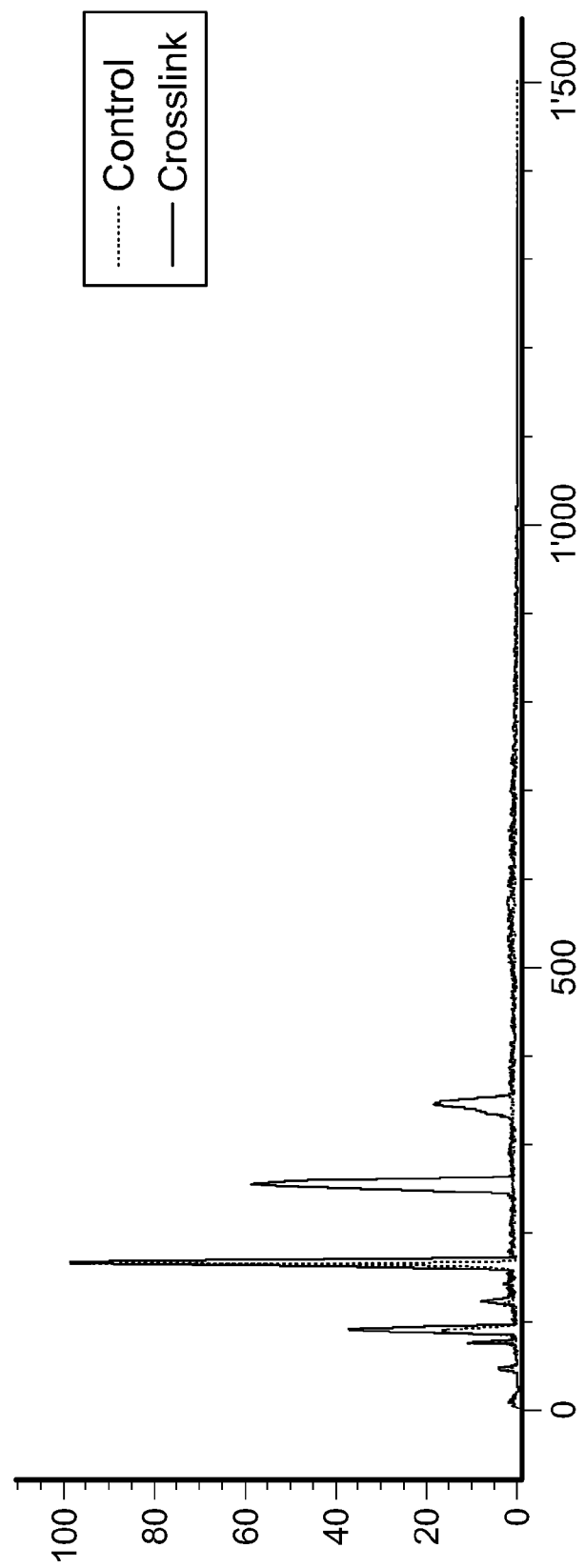
FIG. 11C) Using Complex Tracker software, we overlaid the control and cross-link spectra. The overlay confirmed the detection of two non covalent complexes [5E5-1•B168] and [5E5-1•2B168].

Analysis of the mix A: 5E5-1/168B, showed that the antigen and the antibody were detected with observed MH+=92.879 kDa (168B-antigen) and MH+=158.498 kDa. (5E5-1 antibody)(FIG. 11A). The cross-linking experiment was completed after 180 minutes incubation time with the crosslinking reagent K200. After cross-linking, we detected two additional peaks with MH+=258.945 kDa [5E5-1•B168] and MH+=354.164 kDa [5E5-1•2B168] (FIG. 11B). Using Complex Tracker software, we overlaid the control and cross-link spectra. The overlay confirmed the detection of two non covalent complexes [5E5-1•B168] and [5E5-1•2B168] (FIG. 11C).

Analysis of the Mix B: 5A1-1/168B, showed that the antigen and the antibody were detected with MH+=92.743 kDa (168B) and MH+=159.125 kDa. (5A1-1) (data not shown). The cross-linking experiment was completed after 180 minutes incubation time with the crosslinking reagent K200. After cross-linking, we detected two additional peaks with MH+=259.155 kDa [5A1-1•B168] and MH+=355.025 kDa [5A1-1•2B168] (data not shown). Using Complex Tracker software, we overlaid the control and cross-link spectra. The overlay confirmed the detection of two non covalent complexes [5A1-1•B168] (antibody binding with a single antigen) and [5A1-1•2B168] (antibody binding to two antigens)(data not shown).

Figure 12A:
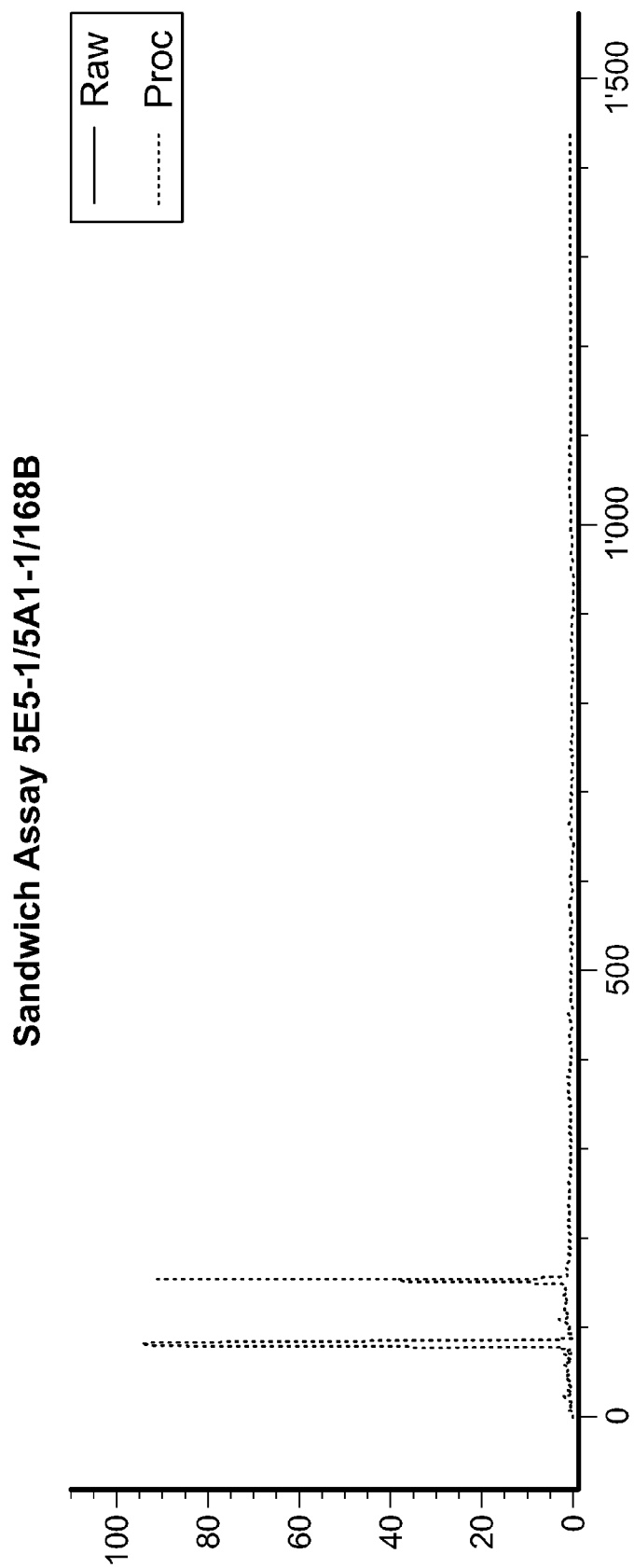
FIG. 12 A) Analysis of the Mix C (both monoclonal antibodies plus antigen): 5E5-1/5A1-1/168B showed that the antigen and the antibody were detected with MH+=92.910 kDa (168B) and MH+=158.988 kDa (5E5, 5A1-1).
FIG. 12B) The cross-linking experiment was completed after 180 minutes incubation time with the crosslinking reagent K200. After cross-linking, we detected two additional peaks with MH+=260.155 kDa and MH+=356.012 kDa.
FIG. 12C) Using Complex Tracker software, we overlaid the control and cross-link spectra. The overlay confirmed the detection of two non covalent complexes [5E5-1•B168] and [5E5-1•2B168].
Figure 12B:
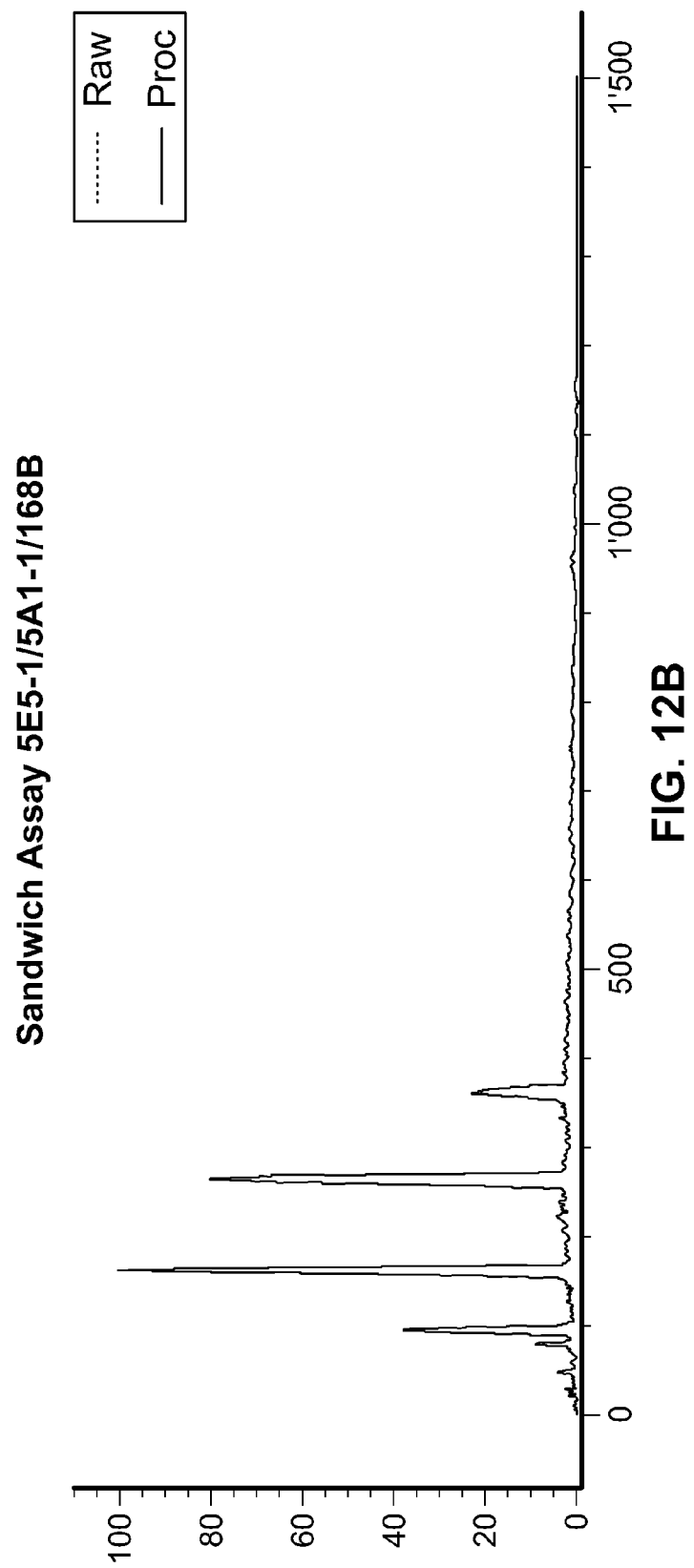

Analysis of the Mix C: 5E5-1/5A1-1/168B showed that the antigen and the antibody were detected with MH+=92.910 kDa (168B) and MH+=158.988 kDa (5E5, 5A1-1). (FIG. 12A). The cross-linking experiment was completed after 180 minutes incubation time with the cross-linking reagent K200. After cross-linking, we detected two additional peaks with MH+=260.155 kDa and MH+=356.012 kDa (FIG. 12B). Using Complex Tracker software, we overlaid the control and cross-link spectra. The overlay confirmed the detection of two non covalent complexes [5E5-1•B168] and [5E5-1•2B168]. (FIG. 12C).

Discussion

The sandwich assay indicated that the simultaneous binding of the monoclonal antibodies 5E5-1 and 5A1-1 on the antigen 168 B was not observed. The analysis indicated that the epitope of these two monoclonal antibodies on the antigen 168B are located in the same close region of the protein.

Example 8

Epitope Mapping of Antibody 5E5-1

A competition assay with peptides derived from the antigen was conducted to determine if the epitope was linear.

Pepsin Proteolysis

In order to determine the nature of the epitope, we performed a proteolysis of 168B antigen with immobilized pepsin. 10 µl of the antigen with a concentration of 2.5 µM were mixed with immobilized pepsin 2.5 µM and incubated at room temperature for 30 minutes. After the incubation time the sample was centrifuged and the supernatant was pipetted. The completion of the proteolysis was controlled by High-Mass MALDI mass spectrometry in linear mode and reflectron mode. The pepsin proteolysis was optimized in order to obtain large amounts of peptides in the 1000-3500 Da range.

Pepsin Peptides/Antibody/Antigen Mixing and Incubation

5 µl of the antigen peptides generated by proteolysis was concentrated 10× using speed vac and mixed with 5 µl of 5E5-1 antibody (4 µM) and incubated at 37° for 2 hours.

Antigen Peptides/Antigen/Antibody Mixing

After incubation of the antibodies with the antigen peptides, 5 µl of the mixture is mixed with 5 µl of the intact antigen (4 µM). After mixing, the mixture contains the following proteins: 168B peptides 5E5-1 Antibody/168B antigen peptides Mix 5E5-1 antibody/168B peptides/168B antigen.

Interaction Analysis

For the competition assay, the antibody/antigen interaction analysis was performed with the same protocol as described in Example 6.

Results

Figure 13A:
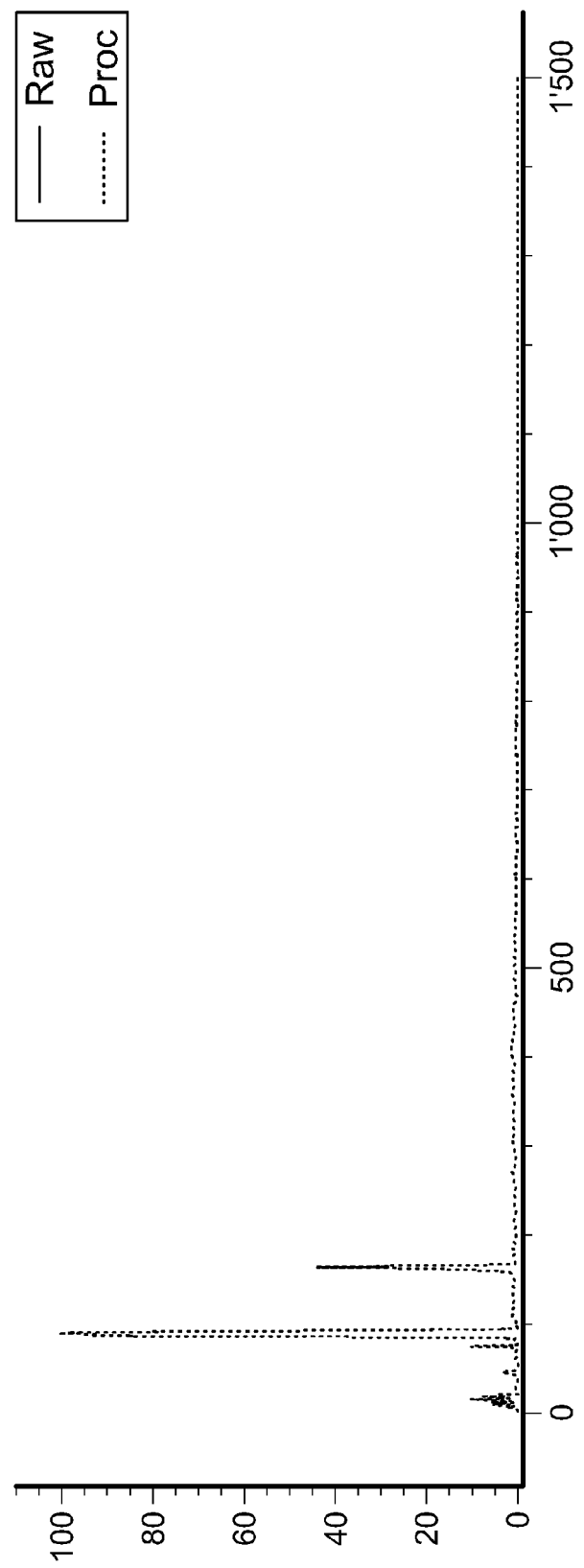
FIG. 13 A) After competition with tryptic peptides, we did not detect inhibition of the binding of the antibody 5E5-1 on the antigen 168B.
FIG. 13B) After competition, we observed two non covalent complexes: [5E5-1•B168] and [5E5-1•2B168] FIG. 13C) Using Complex Tracker software, we overlaid the control and cross-link spectra. The overlay confirmed the detection of two non covalent complexes [5E5-1•B168] and [5E5-1•2B168].
Figure 13B:
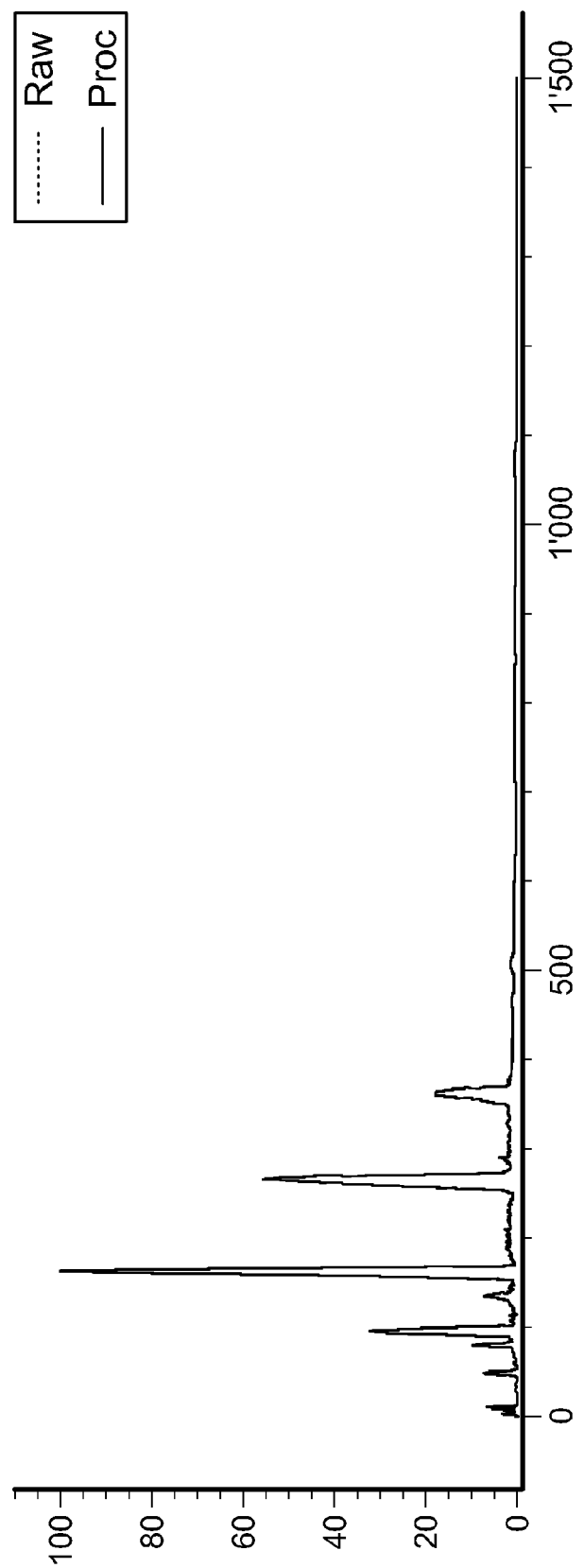
Figure 13C:
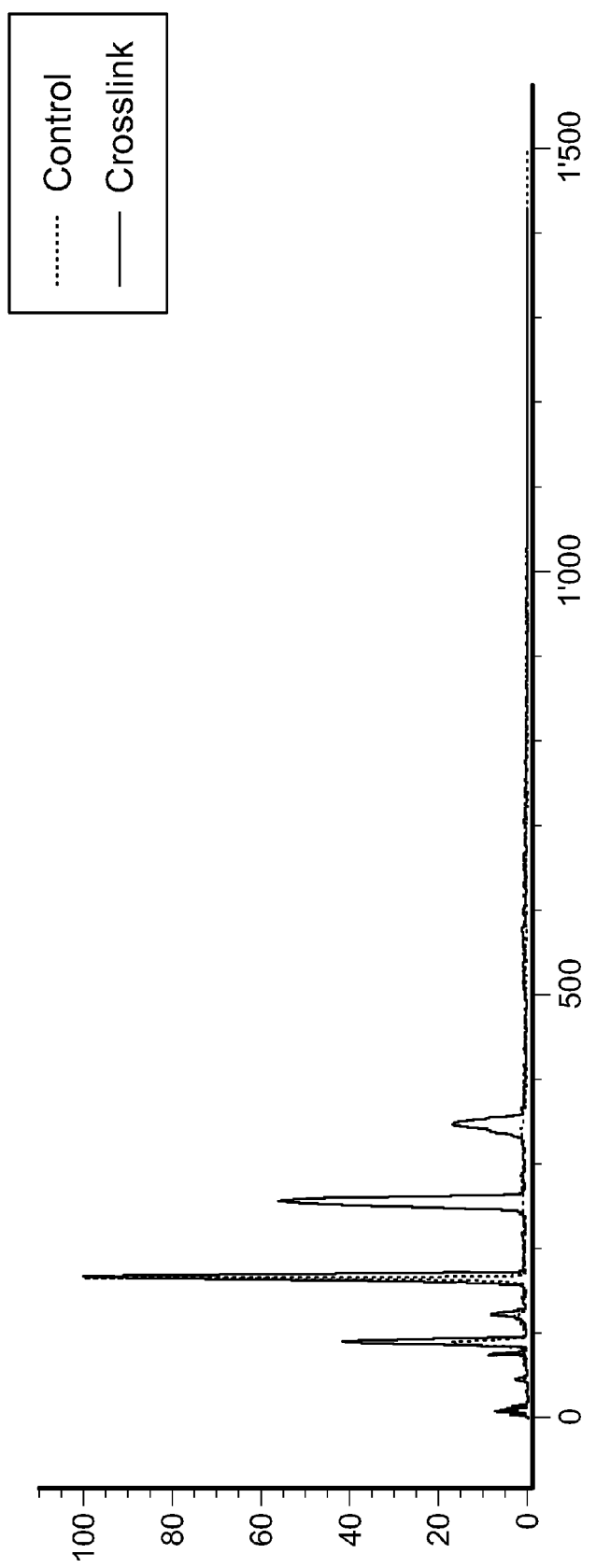

For this experiment, the antigen and the antibody were detected with MH+=92.879 kDa and MH+=158.498 kDa. (FIG. 13A). The cross-linking experiment was completed after 180 minutes incubation time with the crosslinking reagent K200. After cross-linking, we detected two additional peaks with MH+=258.945 kDa and MH+=354.164 kDa. Using Complex Tracker software, we overlaid the control and cross-link spectra. (FIG. 13B) The overlay confirmed the detection of two non covalent complexes [5E5-1•B168] and [5E5-1•2B168] (FIG. 13C).

After competition, we did not detect inhibition of the binding of the antibody 5E5-1 on the antigen 168B. After competition, we observed two non covalent complexes: [5E5-1•B168] and [5E5-1•2B168] (FIG. 13).

Discussion

The competition assay indicated that peptides of the antigen are not inhibiting the binding Antibody/Antigen. The epitope 5E5-1 on 168B is not linear. The epitope is based on the conformation of the antigen.

Characterization of the Molecular Interfaces B168/5E5-1

In order to determine the epitope of 5E5-1 antibody on 168B antigen with high resolution the antibody/antigen complexes are incubated with deuterated cross-linkers and subjected to multienzymatic cleavage. After enrichment of the cross-linked peptides, the samples are analyzed by high resolution mass spectrometry (nLC-Orbitrap MS) and the data generated are analyzed using XQuest and Stavrox software.

For this analysis, a nLC in combination with Orbitrap mass spectrometry have been used as described above. 5 µl of the antigen sample (concentration 4 µM) was mixed with 5 µl of the antibody sample (Concentration 2 µM) in order to obtain an antibody/antigen mix with final concentration 1 µM/2 µM. The mixture was incubated at 37° C. for 180 minutes. In a first step, 1 mg of d0 cross-linker was mixed with 1 mg of d1 2 cross-linker. The 2 mg prepared were mixed with 1 ml of DMF in order to obtain a 2 mg/ml solution of DSS d0/d12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

In order to facilitate the proteolysis, it is necessary to reduce the disulfide bond present in this protein. The cross-linked sample was mixed with 20 µl of ammonium bicarbonate (25 mM, pH 8.3). After mixing 2.5 µl of DTT (500 mM) is added to the solution. The mixture is then incubated 1 hour at 55° C. After incubation, 2.5 µl of iodioacetamide (1M) is added before 1 hour of incubation at room temperature in a dark room. After incubation, the solution is diluted 1/5 by adding 120 µl of the buffer used for the proteolysis.

145 µl of the reduced/alkyled cross-linked sample was mixed with 2 µl of trypsin (Roche). The proteolytic mixture was incubated overnight at 37° C.

For this proteolysis, the buffer is Tris-HCL 100 mM, CaCl2 10 mM, pH7.8. 145 µl of the reduced/alkyled cross-linked complex were mixed with 2 µl of α-chymotrypsin 200 µM and incubated overnight at 30° C.

145 µl of the reduced/alkyled cross-linked sample was mixed with 2 µl of ASP-N (Roche). The proteolytic mixture was incubated overnight at 37° C.

Results

After cross-linking, the peptides generated by multienzymatic proteolysis are covering 81% of the total antigen sequence. After trypsin digestion of the antibody/antigen cross-linked complex with deuterated d0 d12, the nLC-orbitrap MS/MS analysis allowed to detect 32 peptides having monolinks. These monolinked peptides have been detected with both Xquest and Stavrox software.

After trypsin digestion of the antibody/antigen cross-linked complex with deuterated d0 d12, the nLC-orbitrap MS/MS analysis allowed to detect 4 cross-linked peptides between the antigen 168B and the antibody 5E5-1 heavy chain. These cross-linked peptides have been detected with both Xquest and Stavrox software.

```
Trypsin Cross-link Identified: 168B/5E5-1
Protein 1/Protein 2
QIIGYVIGTQQATPGPAYSGR-LSGTAGVHSQVQL-a19-b2

Position Protein 1/Protein2
168B 78-98  5E5-1 HC 11-24
(1-4 of heavy chain variable domain)

Protein 1/Protein 2
QIIGYVIGTQQATPGPAYSGR-LSGTAGVHSQVQL-a21-b2

Position Protein 1/Protein2
168B 78-98  5E5-1 HC 11-24
(1-4 of heavy chain variable domain)
```

-continued

```
Protein 1/Protein 2
SDLVNEEATGQFR-VQLQQSGAD-a1-b6

Position Protein 1/Protein2
168B 127-139 5E5-1 HC 21-29
(1-9 of heavy chain variable domain)

Protein 1/Protein 2
SDLVNEEATGQFR-VQLQQSGAD-a13-b6

Position Protein 1/Protein2
168B 127-139 5E5-1 HC 21-29
(1-9 of heavy chain variable domain)
```

After chymotrypsin digestion of the antibody/antigen cross-linked complex with deuterated d0 d12, the nLC-orbitrap MS/MS analysis allowed to detect 4 cross-linked peptides between 168 B antigen and 5E5-1 antibody Heavy Chain and light chain. These cross-linked peptides have been detected with both Xquest and Stavrox software.

```
Chymotrypsin Cross-link Identified: 168B/5E5-1
Protein 1/Protein 2
HLFGYSWYK-QLLGLLLLCFQGTRC-a6-b14

Position Protein 1/Protein2
168B 61-69 5E5-1 LC 6-20

Protein 1/Protein 2
HLFGYSWYK-IQMTQITSS-a9-b8

Position Protein 1/Protein2
168B 61-69 5E5-1 LC 22-30
(2-9 of light chain variable domain)

Protein 1/Protein 2
SGREIIYPNASL-GVHSQVQLQQS-a1-b4

Position Protein 1/Protein2
168B 96-107 5E5-1 HC 16-26
(1-7 of heavy chain variable domain)

Protein 1/Protein 2
SGREIIYPNASL-GVHSQVQLQQS-a3-b11

Position Protein 1/Protein2
168B 96-107 5E5-1 HC 16-26
(1-7 of heavy chain variable domain)
```

After ASP-N digestion of the antibody/antigen cross-linked complex we did not detect any crosslinked peptides between 168B and 5E5-1.

Discussion

Using chemical cross-linking, High-Mass MALDI mass spectrometry and nLC-Orbitrap mass spectrometry we were able to characterize the interaction interface between the antigen 168B and the monoclonal antibody 5E5-1. Our analysis indicates that the epitope of this monoclonal antibody includes the following amino acids on 168B: 66; 69; 96; 98; 127; 139. On the antibody the paratope includes the following amino acids: Heavy chain: 6 Light Chain: 9. These results are illustrated in FIG. 15.

Example 9

A competition assay with peptides derived from the antigen was conducted to determine if the epitope was linear for antibody 5A1-1.

Pepsin Proteolysis

In order to determine the nature of the epitope, we performed a proteolysis of 168B antigen with immobilized pepsin. 10 µl of the antigen with a concentration of 2.5 µM were mixed with immobilized pepsin 2.5 µM and incubated at room temperature for 30 minutes. After the incubation time the sample was centrifuged and the supernatant was pipetted. The completion of the proteolysis was controlled by High-Mass MALDI mass spectrometry in linear mode and reflectron mode. The pepsin proteolysis was optimized in order to obtain large amounts of peptides in the 1000-3500 Da range.

Pepsin Peptides/Antibody/Antigen Mixing and Incubation

5 µl of the antigen peptides generated by proteolysis was concentrated 10× using speed vac and mixed with 5 µl of 5A1-1 antibody (4 µM) and incubated at 37° for 2 hours.

Antigen Peptides/Antigen/Antibody Mixing

After incubation of the antibodies with the antigen peptides, 5 µl of the mixture is mixed with 5 µl of the intact antigen (4 µM). After mixing, the mixture contains the following proteins: 168B peptides 5A1-1 Antibody/168B antigen peptides Mix 5A1-1 antibody/168B peptides/168B antigen.

Interaction Analysis

For the competition assay, the antibody/antigen interaction analysis was performed with the same protocol as described in Example 6.

Results

For this experiment, the antigen and the antibody were detected with MH+=92.879 kDa and MH+=158.498 kDa. (data not shown). The cross-linking experiment was completed after 180 minutes incubation time with the crosslinking reagent K200. After cross-linking, we detected two additional peaks with MH+=258.945 kDa and MH+=354.164 kDa. Using Complex Tracker software, we overlaid the control and cross-link spectra. (data not shown) The overlay confirmed the detection of two non covalent complexes [5A1-1•B168] and [5A1-1•2B168] (data not shown).

After competition, we did not detect inhibition of the binding of the antibody 5A1-1 on the antigen 168B. After competition, we observed two non covalent complexes: [5A1-1•B168] and [5A1-1•2B168] (data not shown). This indicates the epitope is not linear.

Characterization of the Molecular Interfaces B168/5A1-1

In order to determine the epitope of 5A1-1 antibody on 168B antigen with high resolution the antibody/antigen complexes are incubated with deuterated cross-linkers and subjected to multienzymatic cleavage. After enrichment of the cross-linked peptides, the samples are analyzed by high resolution mass spectrometry (nLC-Orbitrap MS) and the data generated are analyzed using XQuest and Stavrox software.

For this analysis, a nLC in combination with Orbitrap mass spectrometry have been used as described above. 5 µl of the antigen sample (concentration 4 µM) was mixed with 5 µl of the antibody sample (Concentration 2 µM) in order to obtain an antibody/antigen mix with final concentration 1 µM/2 µM. The mixture was incubated at 37° C. for 180 minutes. In a first step, 1 mg of d0 cross-linker was mixed with 1 mg of d12 cross-linker. The 2 mg prepared were mixed with 1 ml of DMF in order to obtain a 2 mg/ml solution of DSS d0/d12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

In order to facilitate the proteolysis, it is necessary to reduce the disulfide bond present in this protein. The cross-linked sample was mixed with 20 µl of ammonium bicarbonate (25 mM, pH 8.3). After mixing 2.5 µl of DTT (500 mM) is added to the solution. The mixture is then incubated 1 hour at 55° C. After incubation, 2.5 µl of iodoacetamide (1M) is added before 1 hour of incubation at room temperature in a dark room. After incubation, the solution is diluted 1/5 by adding 120 µl of the buffer used for the proteolysis.

145 µl of the reduced/alkyled cross-linked sample was mixed with 2 µl of trypsin (Roche). The proteolytic mixture was incubated overnight at 37° C.

For this proteolysis, the buffer is Tris-HCL 100 mM, CaCl2 10 mM, pH7.8. 145 µl of the reduced/alkyled cross-linked complex were mixed with 2 µl of α-chymotrypsin 200 µM and incubated overnight at 30° C.

145 µl of the reduced/alkyled cross-linked sample was mixed with 2 µl of ASP-N (Roche). The proteolytic mixture was incubated overnight at 37° C.

Results

After cross-linking, the peptides generated by multi-enzymatic proteolysis are covering 81% of the total antigen sequence. After trypsin digestion of the antibody/antigen cross-linked complex with deuterated d0 d12, the nLC-orbitrap MS/MS analysis allowed to detect 35 peptides having monolinks. These monolinked peptides have been detected with both Xquest and Stavrox software.

After trypsin digestion of the antibody/antigen cross-linked complex with deuterated d0 d12, the nLC-orbitrap MS/MS analysis allowed to detect 4 cross-linked peptides between the antigen 168B and the antibody 5A1-1 heavy chain. These cross-linked peptides have been detected with both Xquest and Stavrox software.

```
Trypsin Cross-link Identified: 168B/5A1-1
Protein 1/Protein 2
VDGNR-VKPGASVKL-a5-b2

Position Protein 1/Protein2
168B 73-77 5A1-1 HC 11-19

Protein 1/Protein 2
VDGNR-VKPGASVKL-a5-b2

Position Protein 1/Protein2
168B 73-77 5A1-1 HC 11-19
```

After chymotrypsin digestion of the antibody/antigen cross-linked complex with deuterated d0 d12, the nLC-orbitrap MS/MS analysis allowed to detect 10 cross-linked peptides between 168 B antigen and 5A1-1 antibody Heavy Chain and light chain. These cross-linked peptides have been detected with both Xquest and Stavrox software.

```
Chymotrypsin Cross-link Identified: 168B/5A1-1
Protein 1/Protein 2
HLFGYSWYK-VGDRVTITCRA-a6-b4

Position Protein 1/Protein2
168B 61-69 5A1-1 LC 15-25

Protein 1/Protein 2
HLFGYSWYK-VGDRVTITCRA-a9-b10

Position Protein 1/Protein2
168B 61-69 5A1-1 LC 15-25

Protein 1/Protein 2
KGERVDGNRQIIGY-TCRASQSISSYLN-a1-b2

Position Protein 1/Protein2
168B 69-82 5A1-1 LC 22-34

Protein 1/Protein 2
KGERVDGNRQIIGY-TCRASQSISSYLN-a4-b10

Position Protein 1/Protein2
168B 69-82 5A1-1 LC 22-34

Protein 1/Protein 2
KGERVDGNRQIIGY-VKPGASVKLS-a9-b2

Position Protein 1/Protein2
168B 69-82 5A1-1 HC 11-19

Protein 1/Protein 2
KGERVDGNRQIIGY-VKPGASVKLS-a9-b6

Position Protein 1/Protein2
168B 69-82 5A1-1 HC 11-19

Protein 1/Protein 2
SGREIIYPNASL-ASVKLSC-a1-b2

Position Protein 1/Protein2
168B 96-107 5A1-1 HC 16-22

Protein 1/Protein 2
SGREIIYPNASL-ASVKLSC-a3-b4

Position Protein 1/Protein2
168B 96-107 5A1-1 HC 16-22

Protein 1/Protein 2
SGREIIYPNASL-CKASGYTFTNYWINWVKP-a11-b2

Position Protein 1/Protein2
168B 96-107 5A1-1 HC 21-39

Protein 1/Protein 2
SGREIIYPNASL-CKASGYTFTNYWINWVKP-a11-b17

Position Protein 1/Protein2
168B 96-107 5A1-1 HC 21-39
```

After ASP-N digestion of the antibody/antigen cross-linked complex we did not detect any crosslinked peptides between 168B and 5A1-1.

Discussion

Using chemical cross-linking, High-Mass MALDI mass spectrometry and nLC-Orbitrap mass spectrometry we were able to characterize the interaction interface between the antigen 168B and the monoclonal antibody 5A1-1. Our analysis indicates that the epitope of this monoclonal antibody includes the following amino acids on 168B: 66; 69; 72; 77; 96; 98; 106. On the antibody the paratope includes the following amino acids: Heavy chain: 15; 19; 21; 23; 25; 40 and CDRH1. Light Chain: 18; 24; 31 and CDRL1. These results are illustrated in FIG. 16.

It is apparent that many modifications and variations of this invention as set forth above may be made without departing from the spirit and scope. The specific embodiments described are given by way of example only, and the invention is limited only by the terms of the appended claims.

What is claimed:

1. An immunoassay for determining whether a subject is at risk of cancer, the immunoassay comprising:
   a) combining an antibody or antigen binding fragment thereof with a sample from the subject; wherein the antibody or antigen binding fragment thereof specifically binds to a 100 kDa glycoprotein comprising SEQ ID NO:1, but does not substantially bind to glycosylated 180 kDa CEA and to one or more linear peptides selected from the group consisting of 15 amino acids from amino acids of SEQ ID NO:2, amino acids of SEQ ID NO:3, and 15 amino acids from amino acids of SEQ ID NO:4, and wherein said antibody or antigen binding fragment binds to an epitope comprised within amino acids of SEQ ID NO:6, 7, 8, 9, 10 or 11; and
   b) determining the amount of the antigen in the sample by determining the amount of the antibody antigen complex.

2. The immunoassay of claim 1, wherein the antibody or antigen binding fragment thereof is a monoclonal antibody or antigen binding fragment thereof.

3. The immunoassay of claim 2, wherein the antibody or antigen binding fragment is a capture antibody or antigen binding fragment thereof.

4. The immunoassay of claim 1, further comprising a second antibody or antigen binding fragment thereof, wherein the second antibody or antigen binding fragment thereof specifically binds to a 100 kDa glycoprotein comprising SEQ ID NO:1, but does not substantially bind to glycosylated 180 kDa CEA and to one or more linear peptides selected from the group consisting of 15 amino acids from amino acids of SEQ ID NO:2, amino acids of SEQ ID NO:3, and 15 amino acids from amino acids of SEQ ID NO:4, and wherein said antibody or antigen binding fragment binds to an epitope comprised within amino acids of SEQ ID NO:6, 7, 8, 9, 10 or 11.

5. The immunoassay of claim 4, wherein the second antibody or antigen binding fragment thereof is a monoclonal antibody or antigen binding fragment thereof.

6. The immunoassay of claim 5, wherein the second antibody or antigen binding fragment thereof is a capture antibody or antigen binding fragment thereof.

7. The immunoassay of claim 1, further comprising an additional antibody or antigen binding fragment thereof that specifically binds to the 100 kDa glycoprotein comprising SEQ ID NO:1.

8. The immunoassay of claim 7, wherein said additional antibody or antigen binding fragment thereof is labeled with a label selected from the group consisting of a radionuclide, an enzyme, a fluorescent agent and a chromophore.

9. The immunoassay of claim 8, wherein the additional antibody or antigen binding fragment thereof is a polyclonal antibody or antigen binding fragment thereof.

10. The immunoassay of claim 1, further comprising identifying the subject as at risk for cancer if the amount of the antigen in the sample is about 6.5 units/ml or greater.

11. The immunoassay of claim 1, wherein the sample is a human tissue or fluid.

12. An immunoassay for determining whether a subject is at risk of cancer, the immunoassay comprising:
   a) combining an antibody or antigen binding fragment thereof with a sample from the subject wherein the antibody or antigen binding fragment thereof specifically binds to a 100 kDa glycoprotein comprising SEQ ID NO:1, but does not substantially bind to glycosylated 180 kDa CEA and to one or more linear peptides selected from the group consisting of 15 amino acids from amino acids of SEQ ID NO:2, amino acids of SEQ ID NO:3, and 15 amino acids from amino acids of SEQ ID NO:4, wherein the antibody or antigen binding fragment thereof comprises:
      heavy chain CDRs (HCDR1, HCDR2 and HCDR3) from a heavy chain variable region having the sequence of SEQ ID NO:119; and
      light chain CDRs (LCDR1, LCDR2 and LCDR3) from a light chain variable region having the sequence of SEQ ID NO:120; and
   b) determining the amount of the antigen in the sample by determining the amount of the antibody antigen complex.

13. The immunoassay of claim 12, wherein the antibody or antigen binding fragment thereof comprises the heavy and light chain variable regions.

* * * * *

SEQUENCE LISTING

<160> NUMBER OF SEQ ID NOS: 122

<210> SEQ ID NO 1
<211> LENGTH: 701
<212> TYPE: PRT
<213> ORGANISM: Homo sapiens

<400> SEQUENCE: 1

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Val Thr Thr Ile Thr Val Tyr Glu
305                 310                 315                 320

Pro Pro Lys Pro Phe Ile Thr Ser Asn Asn Ser Asn Pro Val Glu Asp
                325                 330                 335

Glu Asp Ala Val Ala Leu Thr Cys Glu Pro Glu Ile Gln Asn Thr Thr
            340                 345                 350

Tyr Leu Trp Trp Val Asn Asn Gln Ser Leu Pro Val Ser Pro Arg Leu
        355                 360                 365
```

```
Gln Leu Ser Asn Asp Asn Arg Thr Leu Thr Leu Leu Ser Val Thr Arg
    370                 375                 380

Asn Asp Val Gly Pro Tyr Glu Cys Gly Ile Gln Asn Glu Leu Ser Val
385                 390                 395                 400

Asp His Ser Asp Pro Val Ile Leu Asn Val Leu Tyr Gly Pro Asp Asp
                405                 410                 415

Pro Thr Ile Ser Pro Ser Tyr Thr Tyr Tyr Arg Pro Gly Val Asn Leu
            420                 425                 430

Ser Leu Ser Cys His Ala Ala Ser Asn Pro Ala Gln Tyr Ser Trp
        435                 440                 445

Leu Ile Asp Glu Asn Ile Gln Gln His Thr Gln Glu Leu Phe Ile Ser
450                 455                 460

Asn Ile Thr Glu Lys Asn Ser Gly Leu Tyr Thr Cys Gln Ala Asn Asn
465                 470                 475                 480

Ser Ala Ser Gly His Ser Arg Thr Thr Val Lys Thr Ile Thr Val Ser
                485                 490                 495

Ala Glu Leu Pro Lys Pro Ser Ile Ser Ser Asn Asn Ser Lys Pro Val
            500                 505                 510

Glu Asp Lys Asp Ala Val Ala Phe Thr Cys Glu Pro Glu Ala Gln Asn
        515                 520                 525

Thr Thr Tyr Leu Trp Trp Val Asn Gly Gln Ser Leu Pro Val Ser Pro
    530                 535                 540

Arg Leu Gln Leu Ser Asn Gly Asn Arg Thr Leu Thr Leu Phe Asn Val
545                 550                 555                 560

Thr Arg Asn Asp Ala Arg Ala Tyr Val Cys Gly Ile Gln Asn Ser Val
                565                 570                 575

Ser Ala Asn Arg Ser Asp Pro Val Thr Leu Asp Val Leu Tyr Gly Pro
            580                 585                 590

Asp Thr Pro Ile Ile Ser Pro Pro Asp Ser Ser Tyr Leu Ser Gly Ala
        595                 600                 605

Asn Leu Asn Leu Ser Cys His Ser Ala Ser Asn Pro Ser Pro Gln Tyr
    610                 615                 620

Ser Trp Arg Ile Asn Gly Ile Pro Gln Gln His Thr Gln Val Leu Phe
625                 630                 635                 640

Ile Ala Lys Ile Thr Pro Asn Asn Asn Gly Thr Tyr Ala Cys Phe Val
                645                 650                 655

Ser Asn Leu Ala Thr Gly Arg Asn Asn Ser Ile Val Lys Ser Ile Thr
            660                 665                 670

Val Ser Ala Ser Gly Thr Ser Pro Gly Leu Ser Ala Gly Ala Thr Val
        675                 680                 685

Gly Ile Met Ile Gly Val Leu Val Gly Val Ala Leu Ile
    690                 695                 700

<210> SEQ ID NO 2
<211> LENGTH: 60
<212> TYPE: PRT
<213> ORGANISM: Homo sapiens

<400> SEQUENCE: 2

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45
```

```
Lys Glu Val Leu Leu Val His Asn Leu Pro Gln
 50                  55                  60

<210> SEQ ID NO 3
<211> LENGTH: 16
<212> TYPE: PRT
<213> ORGANISM: Homo sapiens

<400> SEQUENCE: 3

Asn Ile Ile Gln Asn Asp Thr Gly Phe Tyr Thr Leu His Val Ile Lys
 1               5                  10                  15

<210> SEQ ID NO 4
<211> LENGTH: 551
<212> TYPE: PRT
<213> ORGANISM: Homo sapiens

<400> SEQUENCE: 4

Ser Asn Asn Ser Lys Pro Val Glu Asp Lys Asp Ala Val Ala Phe Thr
 1               5                  10                  15

Cys Glu Pro Glu Thr Gln Asp Ala Thr Tyr Leu Trp Trp Val Asn Asn
             20                  25                  30

Gln Ser Leu Pro Val Ser Pro Arg Leu Gln Leu Ser Asn Gly Asn Arg
         35                  40                  45

Thr Leu Thr Leu Phe Asn Val Thr Arg Asn Asp Thr Ala Ser Tyr Lys
 50                  55                  60

Cys Glu Thr Gln Asn Pro Val Ser Ala Arg Arg Ser Asp Ser Val Ile
 65                  70                  75                  80

Leu Asn Val Leu Tyr Gly Pro Asp Ala Pro Thr Ile Ser Pro Leu Asn
                 85                  90                  95

Thr Ser Tyr Arg Ser Gly Glu Asn Leu Asn Leu Ser Cys His Ala Ala
            100                 105                 110

Ser Asn Pro Pro Ala Gln Tyr Ser Trp Phe Val Asn Gly Thr Phe Gln
        115                 120                 125

Gln Ser Thr Gln Glu Leu Phe Ile Pro Asn Ile Thr Val Asn Asn Ser
130                 135                 140

Gly Ser Tyr Thr Cys Gln Ala His Asn Ser Asp Thr Gly Leu Asn Arg
145                 150                 155                 160

Thr Thr Val Thr Thr Ile Thr Val Tyr Glu Pro Pro Lys Pro Phe Ile
                165                 170                 175

Thr Ser Asn Asn Ser Asn Pro Val Glu Asp Glu Asp Ala Val Ala Leu
            180                 185                 190

Thr Cys Glu Pro Glu Ile Gln Asn Thr Thr Tyr Leu Trp Trp Val Asn
        195                 200                 205

Asn Gln Ser Leu Pro Val Ser Pro Arg Leu Gln Leu Ser Asn Asp Asn
    210                 215                 220

Arg Thr Leu Thr Leu Leu Ser Val Thr Arg Asn Asp Val Gly Pro Tyr
225                 230                 235                 240

Glu Cys Gly Ile Gln Asn Glu Leu Ser Val Asp His Ser Asp Pro Val
                245                 250                 255

Ile Leu Asn Val Leu Tyr Gly Pro Asp Asp Pro Thr Ile Ser Pro Ser
            260                 265                 270

Tyr Thr Tyr Tyr Arg Pro Gly Val Asn Leu Ser Leu Ser Cys His Ala
        275                 280                 285

Ala Ser Asn Pro Pro Ala Gln Tyr Ser Trp Leu Ile Asp Glu Asn Ile
    290                 295                 300
```

Gln Gln His Thr Gln Glu Leu Phe Ile Ser Asn Ile Thr Glu Lys Asn
305                 310                 315                 320

Ser Gly Leu Tyr Thr Cys Gln Ala Asn Asn Ser Ala Ser Gly His Ser
            325                 330                 335

Arg Thr Thr Val Lys Thr Ile Thr Val Ser Ala Glu Leu Pro Lys Pro
            340                 345                 350

Ser Ile Ser Ser Asn Asn Ser Lys Pro Val Glu Asp Lys Asp Ala Val
            355                 360                 365

Ala Phe Thr Cys Glu Pro Glu Ala Gln Asn Thr Thr Tyr Leu Trp Trp
370                 375                 380

Val Asn Gly Gln Ser Leu Pro Val Ser Pro Arg Leu Gln Leu Ser Asn
385                 390                 395                 400

Gly Asn Arg Thr Leu Thr Leu Phe Asn Val Thr Arg Asn Asp Ala Arg
            405                 410                 415

Ala Tyr Val Cys Gly Ile Gln Asn Ser Val Ser Ala Asn Arg Ser Asp
            420                 425                 430

Pro Val Thr Leu Asp Val Leu Tyr Gly Pro Asp Thr Pro Ile Ile Ser
            435                 440                 445

Pro Pro Asp Ser Ser Tyr Leu Ser Gly Ala Asn Leu Asn Leu Ser Cys
450                 455                 460

His Ser Ala Ser Asn Pro Ser Pro Gln Tyr Ser Trp Arg Ile Asn Gly
465                 470                 475                 480

Ile Pro Gln Gln His Thr Gln Val Leu Phe Ile Ala Lys Ile Thr Pro
            485                 490                 495

Asn Asn Asn Gly Thr Tyr Ala Cys Phe Val Ser Asn Leu Ala Thr Gly
            500                 505                 510

Arg Asn Asn Ser Ile Val Lys Ser Ile Thr Val Ser Ala Ser Gly Thr
            515                 520                 525

Ser Pro Gly Leu Ser Ala Gly Ala Thr Val Gly Ile Met Ile Gly Val
530                 535                 540

Leu Val Gly Val Ala Leu Ile
545                 550

<210> SEQ ID NO 5
<211> LENGTH: 150
<212> TYPE: PRT
<213> ORGANISM: Homo sapiens

<400> SEQUENCE: 5

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
            85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp

```
            115                 120                 125
Leu Val Asn Glu Glu Ala Thr Gly Gln Phe Arg Val Tyr Pro Glu Leu
    130                 135                 140

Pro Lys Pro Ser Ile Ser
145                 150
```

<210> SEQ ID NO 6
<211> LENGTH: 9
<212> TYPE: PRT
<213> ORGANISM: Homo sapiens

<400> SEQUENCE: 6

```
His Leu Phe Gly Tyr Ser Trp Tyr Lys
1               5
```

<210> SEQ ID NO 7
<211> LENGTH: 5
<212> TYPE: PRT
<213> ORGANISM: Homo sapiens

<400> SEQUENCE: 7

```
Val Asp Gly Asn Arg
1               5
```

<210> SEQ ID NO 8
<211> LENGTH: 14
<212> TYPE: PRT
<213> ORGANISM: Homo sapiens

<400> SEQUENCE: 8

```
Lys Gly Glu Arg Val Asp Gly Asn Arg Gln Ile Ile Gly Tyr
1               5                   10
```

<210> SEQ ID NO 9
<211> LENGTH: 12
<212> TYPE: PRT
<213> ORGANISM: Homo sapiens

<400> SEQUENCE: 9

```
Ser Gly Arg Glu Ile Ile Tyr Pro Asn Ala Ser Leu
1               5                   10
```

<210> SEQ ID NO 10
<211> LENGTH: 21
<212> TYPE: PRT
<213> ORGANISM: Homo sapiens

<400> SEQUENCE: 10

```
Gln Ile Ile Gly Tyr Val Ile Gly Thr Gln Gln Ala Thr Pro Gly Pro
1               5                   10                  15

Ala Tyr Ser Gly Arg
            20
```

<210> SEQ ID NO 11
<211> LENGTH: 13
<212> TYPE: PRT
<213> ORGANISM: Homo sapiens

<400> SEQUENCE: 11

```
Ser Asp Leu Val Asn Glu Glu Ala Thr Gly Gln Phe Arg
1               5                   10
```

<210> SEQ ID NO 12

<211> LENGTH: 1389
<212> TYPE: DNA
<213> ORGANISM: Mus musculus

<400> SEQUENCE: 12

| | |
|---|---:|
| atggaatgca gctgggtaat gctcttcatc ctctcaggaa ctgcaggtgt ccactcccag | 60 |
| gttcagctgc agcagtctgg agctgatctg gcgaggcccg ggcttcagt gatgctgtcc | 120 |
| tgcagggctt ctggcaacac cttcactgac tcctatataa actgggtgaa gcagaggcct | 180 |
| ggacagggcc ttgagtggat tggagagatt tatcctggaa atggtgacgt ttactacaat | 240 |
| gaaaacttta aggacaaggc cacactgact gcagacaaat cctccaacac agcctacatg | 300 |
| aagctcagca gcctgacatc tggggactct gcagtctatc tctgtgcagg atctaatatg | 360 |
| attacgacgg tctttgcgta ctggggccaa gggactctgg tcactgtctc tgcagctaaa | 420 |
| acgacacccc catctgtcta ccactggcc cctggatctg ctgcccaaac taactccatg | 480 |
| gtgaccctgg gatgcctggt caagggctat ttccctgagc cagtgacagt gacctggaac | 540 |
| tctggatccc tgtccagcgg tgtgcacacc ttccagctg cctgcagtc tgacctctac | 600 |
| actctgagca gctcagtgac tgtcccctcc agcacctggc ccagcgagac cgtcacctgc | 660 |
| aacgttgccc accggccag cagcaccaag gtggacaaga aaattgtgcc cagggattgt | 720 |
| ggttgtaagc cttgcatatg tacagtccca gaagtatcat ctgtcttcat cttcccccca | 780 |
| aagcccaagg atgtgctcac cattactctg actcctaagg tcacgtgtgt tgtggtagac | 840 |
| atcagcaagg atgatcccga ggtccagttc agctggtttg tagatgatgt ggaggtgcac | 900 |
| acagctcaga cgcaaccccg ggaggagcag ttcaacagca ctttccgctc agtcagtgaa | 960 |
| cttcccatca tgcaccagga ctggctcaat ggcaaggagt tcaaatgcag ggtcaacagt | 1020 |
| gcagctttcc ctgcccccat cgagaaaacc atctccaaaa ccaaaggcag accgaaggct | 1080 |
| ccacaggtgt acaccattcc acctcccaag gagcagatgg ccaaggataa agtcagtctg | 1140 |
| acctgcatga taacagactt cttccctgaa gacattactg tggagtggca gtggaatggg | 1200 |
| cagccagcgg agaactacaa gaacactcag cccatcatgg acacagatgg ctcttacttc | 1260 |
| gtctacagca agctcaatgt gcagaagagc aactgggagg caggaaatac tttcacctgc | 1320 |
| tctgtgttac atgagggcct gcacaaccac catactgaga agagcctctc ccactctcct | 1380 |
| ggtaaatag | 1389 |

<210> SEQ ID NO 13
<211> LENGTH: 462
<212> TYPE: PRT
<213> ORGANISM: Mus musculus

<400> SEQUENCE: 13

Met Glu Cys Ser Trp Val Met Leu Phe Ile Leu Ser Gly Thr Ala Gly
1               5                   10                  15

Val His Ser Gln Val Gln Leu Gln Gln Ser Gly Ala Asp Leu Ala Arg
            20                  25                  30

Pro Gly Ala Ser Val Met Leu Ser Cys Arg Ala Ser Gly Asn Thr Phe
        35                  40                  45

Thr Asp Ser Tyr Ile Asn Trp Val Lys Gln Arg Pro Gly Gln Gly Leu
    50                  55                  60

Glu Trp Ile Gly Glu Ile Tyr Pro Gly Asn Gly Asp Val Tyr Tyr Asn
65                  70                  75                  80

Glu Asn Phe Lys Asp Lys Ala Thr Leu Thr Ala Asp Lys Ser Ser Asn
                85                  90                  95

```
Thr Ala Tyr Met Lys Leu Ser Ser Leu Thr Ser Gly Asp Ser Ala Val
                100                 105                 110

Tyr Leu Cys Ala Gly Ser Asn Met Ile Thr Thr Val Phe Ala Tyr Trp
            115                 120                 125

Gly Gln Gly Thr Leu Val Thr Val Ser Ala Ala Lys Thr Thr Pro Pro
        130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
450                 455                 460

<210> SEQ ID NO 14
<211> LENGTH: 6
<212> TYPE: PRT
<213> ORGANISM: Mus musculus

<400> SEQUENCE: 14

Thr Asp Ser Tyr Ile Asn
```

<210> SEQ ID NO 15
<211> LENGTH: 10
<212> TYPE: PRT
<213> ORGANISM: Mus musculus

<400> SEQUENCE: 15

Gly Asn Thr Phe Thr Asp Ser Tyr Ile Asn
1               5                   10

<210> SEQ ID NO 16
<211> LENGTH: 16
<212> TYPE: PRT
<213> ORGANISM: Mus musculus

<400> SEQUENCE: 16

Glu Ile Tyr Pro Gly Asn Gly Asp Val Tyr Tyr Asn Glu Asn Phe Lys
1               5                   10                  15

<210> SEQ ID NO 17
<211> LENGTH: 6
<212> TYPE: PRT
<213> ORGANISM: Mus musculus

<400> SEQUENCE: 17

Thr Thr Val Phe Ala Tyr
1               5

<210> SEQ ID NO 18
<211> LENGTH: 14
<212> TYPE: PRT
<213> ORGANISM: Mus musculus

<400> SEQUENCE: 18

Leu Cys Ala Gly Ser Asn Met Ile Thr Thr Val Phe Ala Tyr
1               5                   10

<210> SEQ ID NO 19
<211> LENGTH: 10
<212> TYPE: PRT
<213> ORGANISM: Mus musculus

<400> SEQUENCE: 19

Gly Tyr Thr Phe Thr Asn Tyr Trp Ile Asn
1               5                   10

<210> SEQ ID NO 20
<211> LENGTH: 5
<212> TYPE: PRT
<213> ORGANISM: Mus musculus

<400> SEQUENCE: 20

Asn Tyr Trp Ile Asn
1               5

<210> SEQ ID NO 21
<211> LENGTH: 16
<212> TYPE: PRT
<213> ORGANISM: Mus musculus

<400> SEQUENCE: 21

Asn Ile Tyr Pro Gly Ser Thr Arg Ala Asn Tyr Asn Glu Lys Phe Lys
1               5                   10                  15

<210> SEQ ID NO 22
<211> LENGTH: 8
<212> TYPE: PRT
<213> ORGANISM: Mus musculus

<400> SEQUENCE: 22

Tyr Cys Thr Arg Thr His Ser Ile
1               5

<210> SEQ ID NO 23
<211> LENGTH: 123
<212> TYPE: PRT
<213> ORGANISM: Mus musculus

<400> SEQUENCE: 23

Gln Val Gln Leu Glu Glu Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Thr Arg Ala Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Val Ser Ser Leu Thr Ser Asp Asp Ser Ala Val Tyr Tyr Cys
                85                  90                  95

Thr Arg Thr His Ser Ile Trp Gly Gln Gly Thr Gln Val Thr Val Ser
            100                 105                 110

Ala Ala Lys Thr Thr Pro Pro Ser Val Tyr Ser
        115                 120

<210> SEQ ID NO 24
<211> LENGTH: 375
<212> TYPE: DNA
<213> ORGANISM: Mus musculus

<400> SEQUENCE: 24
cttccgcaag tgcagctgga ggagtctggt gctgagcttg tgaagcctgg ggcctcagtg      60
aagctgtcct gcaaggcttc tggctacact ttcaccaact actggataaa ctgggtgaag     120
cagaggcctg gacaaggcct tgagtggatt ggaaatattt atcctggtag tactagggct     180
aattataatg agaaattcaa gagcaaggcc acactgactg tagacacatc ctccagcaca     240
gcctacatgc aggtcagcag cctgacatct gacgactctg cggtctatta ttgtacaaga     300
acccacagta tctggggcca agggactcag gtcactgtct ctgcagccaa aacgacaccc     360
ccatctgtct attcc                                                      375

<210> SEQ ID NO 25
<211> LENGTH: 705
<212> TYPE: DNA
<213> ORGANISM: Mus musculus

<400> SEQUENCE: 25
atgatgagtc ctgcccagtt ccttggtctc ctgttgctct gttttcaagg taccagatgt      60
gatatccaga tgacacagat tacttcttcc ctgtctgcct ctctgggaga cagagtcacc     120
atcagttgta gggcaagtca ggacattagg aattatttaa actggtatca gcagaaacca     180

-continued

```
gatggaactg ttaaactcct gatctcctac acatcaagat tacattcagg agtcccatca      240
aggttcagtg gcagtgggtc tggaacagat tattctctca ttattagtaa cctggagcaa      300
gaagatattg ccacttactt ttgccaacag gtaatacgc ttccgtggac gttcggtgga      360
ggcaccaaac tggaaatcaa acgggctgat gctgcaccaa ctgtatccat cttcccacca      420
tccagtgagc agttaacatc tggaggtgcc tcagtcgtgt gcttcttgaa caacttctac      480
cccaaagaca tcaatgtcaa gtggaagatt gatggcagtg aacgacaaaa tggcgtcctg      540
aacagttgga ctgatcagga cagcaaagac agcacctaca gcatgagcag caccctcacg      600
ttgaccaagg acgagtatga acgacataac agctatacct gtgaggccac tcacaagaca      660
tcaacttcac ccattgtcaa gagcttcaac aggaatgagt gttag                      705
```

<210> SEQ ID NO 26
<211> LENGTH: 11
<212> TYPE: PRT
<213> ORGANISM: Mus musculus

<400> SEQUENCE: 26

Arg Ala Ser Gln Asp Ile Arg Asn Tyr Leu Asn
1               5                   10

<210> SEQ ID NO 27
<211> LENGTH: 7
<212> TYPE: PRT
<213> ORGANISM: Mus musculus

<400> SEQUENCE: 27

Tyr Thr Ser Arg Leu His Ser
1               5

<210> SEQ ID NO 28
<211> LENGTH: 8
<212> TYPE: PRT
<213> ORGANISM: Mus musculus

<400> SEQUENCE: 28

Gln Gln Gly Asn Thr Leu Pro Trp
1               5

<210> SEQ ID NO 29
<211> LENGTH: 234
<212> TYPE: PRT
<213> ORGANISM: Mus musculus

<400> SEQUENCE: 29

Met Arg Ala Pro Ala Gln Leu Leu Gly Leu Leu Leu Leu Cys Phe Gln
1               5                   10                  15

Gly Thr Arg Cys Asp Ile Gln Met Thr Gln Ile Thr Ser Ser Leu Ser
                20                  25                  30

Ala Ser Leu Gly Asp Arg Val Thr Ile Ser Cys Arg Ala Ser Gln Asp
            35                  40                  45

Ile Arg Asn Tyr Leu Asn Trp Tyr Gln Gln Lys Pro Asp Gly Thr Val
        50                  55                  60

Lys Leu Leu Ile Ser Tyr Thr Ser Arg Leu His Ser Gly Val Pro Ser
65                  70                  75                  80

Arg Phe Ser Gly Ser Gly Ser Gly Thr Asp Tyr Ser Leu Ile Ile Ser
                85                  90                  95

Asn Leu Glu Gln Glu Asp Ile Ala Thr Tyr Phe Cys Gln Gln Gly Asn
            100                 105                 110

```
Thr Leu Pro Trp Thr Phe Gly Gly Gly Thr Lys Leu Glu Ile Lys Arg
        115                 120                 125

Ala Asp Ala Ala Pro Thr Val Ser Ile Phe Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Gly Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 30
<211> LENGTH: 353
<212> TYPE: DNA
<213> ORGANISM: Mus musculus

<400> SEQUENCE: 30

```
gggacattgt gctcacacag actccatcct ccctgtctgc atctgtagga gacagagtca     60
ccatcacttg ccgggcaagt cagagcatta gcagctattt aaattggtat cagcagaaac    120
cagggaaagc ccctaagctc ctgatctatg cggcatccag tttgcaaagt ggggtcccat    180
caaggttcag tggcagtgga tctgggacag atttcactct caccatcagc agtctgcaac    240
ctgaagattt tgcaacttac tactgtcaac agacggttgt ggcgcctccg ttattcggcc    300
aagggaccaa ggtggaaatc aaacgtgcag atgctgcacc aactgtatcc acc           353
```

<210> SEQ ID NO 31
<211> LENGTH: 11
<212> TYPE: PRT
<213> ORGANISM: Mus musculus

<400> SEQUENCE: 31

```
Arg Ala Ser Gln Ser Ile Ser Ser Tyr Leu Asn
1               5                   10
```

<210> SEQ ID NO 32
<211> LENGTH: 7
<212> TYPE: PRT
<213> ORGANISM: Mus musculus

<400> SEQUENCE: 32

```
Ala Ala Ser Ser Leu Gln Ser
1               5
```

<210> SEQ ID NO 33
<211> LENGTH: 8
<212> TYPE: PRT
<213> ORGANISM: Mus musculus

<400> SEQUENCE: 33

```
Gln Gln Thr Val Val Ala Pro Pro
1               5
```

<210> SEQ ID NO 34
<211> LENGTH: 117
<212> TYPE: PRT
<213> ORGANISM: Mus musculus

<400> SEQUENCE: 34

Asp Ile Val Leu Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Ala Asp Ala Ala
            100                 105                 110

Pro Thr Val Ser Thr
        115

<210> SEQ ID NO 35
<211> LENGTH: 32
<212> TYPE: PRT
<213> ORGANISM: Homo sapiens

<400> SEQUENCE: 35

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

<210> SEQ ID NO 36
<211> LENGTH: 32
<212> TYPE: PRT
<213> ORGANISM: Homo sapiens

<400> SEQUENCE: 36

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

<210> SEQ ID NO 37
<211> LENGTH: 19
<212> TYPE: PRT
<213> ORGANISM: Homo sapiens

<400> SEQUENCE: 37

Pro Phe Asn Val Ala Glu Gly Lys Glu Val Leu Leu Leu Val His Asn
1               5                   10                  15

Leu Pro Gln

<210> SEQ ID NO 38
<211> LENGTH: 11
<212> TYPE: PRT
<213> ORGANISM: Homo sapiens

<400> SEQUENCE: 38

Thr Gly Phe Tyr Thr Leu His Val Ile Lys Ser
1               5                   10

<210> SEQ ID NO 39
<211> LENGTH: 12
<212> TYPE: PRT
<213> ORGANISM: Homo sapiens

<400> SEQUENCE: 39

Ser Ser Asn Asn Ser Lys Pro Val Glu Asp Lys Asp
1               5                   10

<210> SEQ ID NO 40
<211> LENGTH: 10
<212> TYPE: PRT
<213> ORGANISM: Homo sapiens

<400> SEQUENCE: 40

Met Glu Ser Pro Ser Ala Pro Pro His Arg
1               5                   10

<210> SEQ ID NO 41
<211> LENGTH: 7
<212> TYPE: PRT
<213> ORGANISM: Homo sapiens

<400> SEQUENCE: 41

Trp Cys Ile Pro Trp Gln Arg
1               5

<210> SEQ ID NO 42
<211> LENGTH: 18
<212> TYPE: PRT
<213> ORGANISM: Homo sapiens

<400> SEQUENCE: 42

Leu Leu Leu Thr Ala Ser Leu Leu Thr Phe Trp Asn Pro Pro Thr Thr
1               5                   10                  15

Ala Lys

<210> SEQ ID NO 43
<211> LENGTH: 5
<212> TYPE: PRT
<213> ORGANISM: Homo sapiens

<400> SEQUENCE: 43

Val Asp Gly Asn Arg
1               5

<210> SEQ ID NO 44
<211> LENGTH: 21
<212> TYPE: PRT
<213> ORGANISM: Homo sapiens

<400> SEQUENCE: 44

Gln Ile Ile Gly Tyr Val Ile Gly Thr Gln Gln Ala Thr Pro Gly Pro
1               5                   10                  15

Ala Tyr Ser Gly Arg
            20

<210> SEQ ID NO 45
<211> LENGTH: 13
<212> TYPE: PRT

```
<213> ORGANISM: Homo sapiens

<400> SEQUENCE: 45

Ser Asp Leu Val Asn Glu Glu Ala Thr Gly Gln Phe Arg
1               5                   10

<210> SEQ ID NO 46
<211> LENGTH: 21
<212> TYPE: PRT
<213> ORGANISM: Homo sapiens

<400> SEQUENCE: 46

Val Tyr Pro Glu Leu Pro Lys Pro Ser Ile Ser Ser Asn Asn Ser Lys
1               5                   10                  15

Pro Val Glu Asp Lys
            20

<210> SEQ ID NO 47
<211> LENGTH: 8
<212> TYPE: PRT
<213> ORGANISM: Homo sapiens

<400> SEQUENCE: 47

Leu Gln Leu Ser Asn Gly Asn Arg
1               5

<210> SEQ ID NO 48
<211> LENGTH: 9
<212> TYPE: PRT
<213> ORGANISM: Homo sapiens

<400> SEQUENCE: 48

Thr Leu Thr Leu Phe Asn Val Thr Arg
1               5

<210> SEQ ID NO 49
<211> LENGTH: 7
<212> TYPE: PRT
<213> ORGANISM: Homo sapiens

<400> SEQUENCE: 49

Asn Asp Thr Ala Ser Tyr Lys
1               5

<210> SEQ ID NO 50
<211> LENGTH: 10
<212> TYPE: PRT
<213> ORGANISM: Homo sapiens

<400> SEQUENCE: 50

Cys Glu Thr Gln Asn Pro Val Ser Ala Arg
1               5                   10

<210> SEQ ID NO 51
<211> LENGTH: 8
<212> TYPE: PRT
<213> ORGANISM: Homo sapiens

<400> SEQUENCE: 51

Leu Gln Leu Ser Asn Asp Asn Arg
1               5

<210> SEQ ID NO 52
<211> LENGTH: 9
```

```
<212> TYPE: PRT
<213> ORGANISM: Homo sapiens

<400> SEQUENCE: 52

Thr Leu Thr Leu Leu Ser Val Thr Arg
1               5

<210> SEQ ID NO 53
<211> LENGTH: 18
<212> TYPE: PRT
<213> ORGANISM: Homo sapiens

<400> SEQUENCE: 53

Asn Ser Gly Leu Tyr Thr Cys Gln Ala Asn Asn Ser Ala Ser Gly His
1               5                   10                  15

Ser Arg

<210> SEQ ID NO 54
<211> LENGTH: 14
<212> TYPE: PRT
<213> ORGANISM: Homo sapiens

<400> SEQUENCE: 54

Ala Tyr Val Cys Gly Ile Gln Asn Ser Val Ser Ala Asn Arg
1               5                   10

<210> SEQ ID NO 55
<211> LENGTH: 16
<212> TYPE: PRT
<213> ORGANISM: Homo sapiens

<400> SEQUENCE: 55

Ile Asn Gly Ile Pro Gln Gln His Thr Gln Val Leu Phe Ile Ala Lys
1               5                   10                  15

<210> SEQ ID NO 56
<211> LENGTH: 20
<212> TYPE: PRT
<213> ORGANISM: Homo sapiens

<400> SEQUENCE: 56

Ile Thr Pro Asn Asn Asn Gly Thr Tyr Ala Cys Phe Val Ser Asn Leu
1               5                   10                  15

Ala Thr Gly Arg
            20

<210> SEQ ID NO 57
<211> LENGTH: 6
<212> TYPE: PRT
<213> ORGANISM: Homo sapiens

<400> SEQUENCE: 57

Asn Asn Ser Ile Val Lys
1               5

<210> SEQ ID NO 58
<211> LENGTH: 10
<212> TYPE: PRT
<213> ORGANISM: Homo sapiens

<400> SEQUENCE: 58

Glu Ser Pro Ser Ala Pro Pro His Arg Trp
1               5                   10
```

<210> SEQ ID NO 59
<211> LENGTH: 20
<212> TYPE: PRT
<213> ORGANISM: Homo sapiens

<400> SEQUENCE: 59

Glu Ser Thr Pro Phe Asn Val Ala Glu Gly Lys Glu Val Leu Leu Leu
1               5                   10                  15

Val His Asn Leu
            20

<210> SEQ ID NO 60
<211> LENGTH: 9
<212> TYPE: PRT
<213> ORGANISM: Homo sapiens

<400> SEQUENCE: 60

His Leu Phe Gly Tyr Ser Trp Tyr Lys
1               5

<210> SEQ ID NO 61
<211> LENGTH: 14
<212> TYPE: PRT
<213> ORGANISM: Homo sapiens

<400> SEQUENCE: 61

Lys Gly Glu Arg Val Asp Gly Asn Arg Gln Ile Ile Gly Tyr
1               5                   10

<210> SEQ ID NO 62
<211> LENGTH: 13
<212> TYPE: PRT
<213> ORGANISM: Homo sapiens

<400> SEQUENCE: 62

Val Ile Gly Thr Gln Gln Ala Thr Pro Gly Pro Ala Tyr
1               5                   10

<210> SEQ ID NO 63
<211> LENGTH: 12
<212> TYPE: PRT
<213> ORGANISM: Homo sapiens

<400> SEQUENCE: 63

Ser Gly Arg Glu Ile Ile Tyr Pro Asn Ala Ser Leu
1               5                   10

<210> SEQ ID NO 64
<211> LENGTH: 11
<212> TYPE: PRT
<213> ORGANISM: Homo sapiens

<400> SEQUENCE: 64

Ile Gln Asn Ile Ile Gln Asn Asp Thr Gly Phe
1               5                   10

<210> SEQ ID NO 65
<211> LENGTH: 9
<212> TYPE: PRT
<213> ORGANISM: Homo sapiens

<400> SEQUENCE: 65

Val Asn Glu Glu Ala Thr Gly Gln Phe
1               5

<210> SEQ ID NO 66
<211> LENGTH: 11
<212> TYPE: PRT
<213> ORGANISM: Homo sapiens

<400> SEQUENCE: 66

Thr Cys Glu Pro Glu Thr Gln Asp Ala Thr Tyr
1               5                   10

<210> SEQ ID NO 67
<211> LENGTH: 12
<212> TYPE: PRT
<213> ORGANISM: Homo sapiens

<400> SEQUENCE: 67

Val Asn Asn Gln Ser Leu Pro Val Ser Pro Arg Leu
1               5                   10

<210> SEQ ID NO 68
<211> LENGTH: 10
<212> TYPE: PRT
<213> ORGANISM: Homo sapiens

<400> SEQUENCE: 68

Asn Val Thr Arg Asn Asp Thr Ala Ser Tyr
1               5                   10

<210> SEQ ID NO 69
<211> LENGTH: 17
<212> TYPE: PRT
<213> ORGANISM: Homo sapiens

<400> SEQUENCE: 69

Thr Ile Ser Pro Leu Asn Thr Ser Tyr Arg Ser Gly Glu Asn Leu Asn
1               5                   10                  15

Leu

<210> SEQ ID NO 70
<211> LENGTH: 12
<212> TYPE: PRT
<213> ORGANISM: Homo sapiens

<400> SEQUENCE: 70

Ser Cys His Ala Ala Ser Asn Pro Pro Ala Gln Tyr
1               5                   10

<210> SEQ ID NO 71
<211> LENGTH: 12
<212> TYPE: PRT
<213> ORGANISM: Homo sapiens

<400> SEQUENCE: 71

Ile Pro Asn Ile Thr Val Asn Asn Ser Gly Ser Tyr
1               5                   10

<210> SEQ ID NO 72
<211> LENGTH: 11
<212> TYPE: PRT
<213> ORGANISM: Homo sapiens

<400> SEQUENCE: 72

Thr Cys Gln Ala His Asn Ser Asp Thr Gly Leu
1               5                   10

<210> SEQ ID NO 73
<211> LENGTH: 11
<212> TYPE: PRT
<213> ORGANISM: Homo sapiens

<400> SEQUENCE: 73

Asn Arg Thr Thr Val Thr Thr Ile Thr Val Tyr
1               5                   10

<210> SEQ ID NO 74
<211> LENGTH: 17
<212> TYPE: PRT
<213> ORGANISM: Homo sapiens

<400> SEQUENCE: 74

Ile Thr Ser Asn Asn Ser Asn Pro Val Glu Asp Glu Asp Ala Val Ala
1               5                   10                  15
Leu

<210> SEQ ID NO 75
<211> LENGTH: 11
<212> TYPE: PRT
<213> ORGANISM: Homo sapiens

<400> SEQUENCE: 75

Thr Cys Glu Pro Glu Ile Gln Asn Thr Thr Tyr
1               5                   10

<210> SEQ ID NO 76
<211> LENGTH: 18
<212> TYPE: PRT
<213> ORGANISM: Homo sapiens

<400> SEQUENCE: 76

Ser Val Thr Arg Asn Asp Val Gly Pro Tyr Glu Cys Gly Ile Gln Asn
1               5                   10                  15
Glu Leu

<210> SEQ ID NO 77
<211> LENGTH: 10
<212> TYPE: PRT
<213> ORGANISM: Homo sapiens

<400> SEQUENCE: 77

Ser Val Asp His Ser Asp Pro Val Ile Leu
1               5                   10

<210> SEQ ID NO 78
<211> LENGTH: 11
<212> TYPE: PRT
<213> ORGANISM: Homo sapiens

<400> SEQUENCE: 78

Gly Pro Asp Asp Pro Thr Ile Ser Pro Ser Tyr
1               5                   10

<210> SEQ ID NO 79
<211> LENGTH: 22
<212> TYPE: PRT
<213> ORGANISM: Homo sapiens

<400> SEQUENCE: 79

Tyr Arg Pro Gly Val Asn Leu Ser Leu Ser Cys His Ala Ala Ser Asn
1               5                   10                  15

Pro Pro Ala Gln Tyr Ser
            20

<210> SEQ ID NO 80
<211> LENGTH: 12
<212> TYPE: PRT
<213> ORGANISM: Homo sapiens

<400> SEQUENCE: 80

Ile Asp Glu Asn Ile Gln Gln His Thr Gln Glu Leu
1               5                   10

<210> SEQ ID NO 81
<211> LENGTH: 11
<212> TYPE: PRT
<213> ORGANISM: Homo sapiens

<400> SEQUENCE: 81

Ile Ser Asn Ile Thr Glu Lys Asn Ser Gly Leu
1               5                   10

<210> SEQ ID NO 82
<211> LENGTH: 22
<212> TYPE: PRT
<213> ORGANISM: Homo sapiens

<400> SEQUENCE: 82

Val Lys Thr Ile Thr Val Ser Ala Glu Leu Pro Lys Pro Ser Ile Ser
1               5                   10                  15

Ser Asn Asn Ser Lys Pro
            20

<210> SEQ ID NO 83
<211> LENGTH: 11
<212> TYPE: PRT
<213> ORGANISM: Homo sapiens

<400> SEQUENCE: 83

Thr Cys Glu Pro Glu Ala Gln Asn Thr Thr Tyr
1               5                   10

<210> SEQ ID NO 84
<211> LENGTH: 12
<212> TYPE: PRT
<213> ORGANISM: Homo sapiens

<400> SEQUENCE: 84

Val Asn Gly Gln Ser Leu Pro Val Ser Pro Arg Leu
1               5                   10

<210> SEQ ID NO 85
<211> LENGTH: 10
<212> TYPE: PRT
<213> ORGANISM: Homo sapiens

<400> SEQUENCE: 85

Asn Val Thr Arg Asn Asp Ala Arg Ala Tyr
1               5                   10

<210> SEQ ID NO 86
<211> LENGTH: 18
<212> TYPE: PRT

<213> ORGANISM: Homo sapiens

<400> SEQUENCE: 86

Val Cys Gly Ile Gln Asn Ser Val Ser Ala Asn Arg Ser Asp Pro Val
1               5                   10                  15

Thr Leu

<210> SEQ ID NO 87
<211> LENGTH: 14
<212> TYPE: PRT
<213> ORGANISM: Homo sapiens

<400> SEQUENCE: 87

Gly Pro Asp Thr Pro Ile Ile Ser Pro Pro Asp Ser Ser Tyr
1               5                   10

<210> SEQ ID NO 88
<211> LENGTH: 12
<212> TYPE: PRT
<213> ORGANISM: Homo sapiens

<400> SEQUENCE: 88

Ser Cys His Ser Ala Ser Asn Pro Ser Pro Gln Tyr
1               5                   10

<210> SEQ ID NO 89
<211> LENGTH: 13
<212> TYPE: PRT
<213> ORGANISM: Homo sapiens

<400> SEQUENCE: 89

Arg Ile Asn Gly Ile Pro Gln Gln His Thr Gln Val Leu
1               5                   10

<210> SEQ ID NO 90
<211> LENGTH: 12
<212> TYPE: PRT
<213> ORGANISM: Homo sapiens

<400> SEQUENCE: 90

Ile Ala Lys Ile Thr Pro Asn Asn Asn Gly Thr Tyr
1               5                   10

<210> SEQ ID NO 91
<211> LENGTH: 12
<212> TYPE: PRT
<213> ORGANISM: Homo sapiens

<400> SEQUENCE: 91

Ser Gly Thr Ser Pro Gly Leu Ser Ala Gly Ala Thr
1               5                   10

<210> SEQ ID NO 92
<211> LENGTH: 14
<212> TYPE: PRT
<213> ORGANISM: Homo sapiens

<400> SEQUENCE: 92

Ala Thr Val Gly Ile Met Ile Gly Val Leu Val Gly Val Ala
1               5                   10

<210> SEQ ID NO 93
<211> LENGTH: 12
<212> TYPE: PRT

```
<213> ORGANISM: Homo sapiens

<400> SEQUENCE: 93

Asp Thr Gly Phe Tyr Thr Leu His Val Ile Lys Ser
1               5                   10

<210> SEQ ID NO 94
<211> LENGTH: 12
<212> TYPE: PRT
<213> ORGANISM: Homo sapiens

<400> SEQUENCE: 94

Asp Ala Val Ala Phe Thr Cys Glu Pro Glu Thr Gln
1               5                   10

<210> SEQ ID NO 95
<211> LENGTH: 18
<212> TYPE: PRT
<213> ORGANISM: Homo sapiens

<400> SEQUENCE: 95

Asp Thr Ala Ser Tyr Lys Cys Glu Thr Gln Asn Pro Val Ser Ala Arg
1               5                   10                  15

Arg Ser

<210> SEQ ID NO 96
<211> LENGTH: 11
<212> TYPE: PRT
<213> ORGANISM: Homo sapiens

<400> SEQUENCE: 96

Asp Ser Val Ile Leu Asn Val Leu Tyr Gly Pro
1               5                   10

<210> SEQ ID NO 97
<211> LENGTH: 13
<212> TYPE: PRT
<213> ORGANISM: Homo sapiens

<400> SEQUENCE: 97

Asp Asn Arg Thr Leu Thr Leu Leu Ser Val Thr Arg Asn
1               5                   10

<210> SEQ ID NO 98
<211> LENGTH: 15
<212> TYPE: PRT
<213> ORGANISM: Homo sapiens

<400> SEQUENCE: 98

Asp Val Gly Pro Tyr Glu Cys Gly Ile Gln Asn Glu Leu Ser Val
1               5                   10                  15

<210> SEQ ID NO 99
<211> LENGTH: 11
<212> TYPE: PRT
<213> ORGANISM: Homo sapiens

<400> SEQUENCE: 99

Asp Pro Val Ile Leu Asn Val Leu Tyr Gly Pro
1               5                   10

<210> SEQ ID NO 100
<211> LENGTH: 18
<212> TYPE: PRT
```

<213> ORGANISM: Homo sapiens

<400> SEQUENCE: 100

Asp Ala Arg Ala Tyr Val Cys Gly Ile Gln Asn Ser Val Ser Ala Asn
1               5                   10                  15

Arg Ser

<210> SEQ ID NO 101
<211> LENGTH: 8
<212> TYPE: PRT
<213> ORGANISM: Homo sapiens

<400> SEQUENCE: 101

Asp Thr Pro Ile Ile Ser Pro Pro
1               5

<210> SEQ ID NO 102
<211> LENGTH: 21
<212> TYPE: PRT
<213> ORGANISM: Homo sapiens

<400> SEQUENCE: 102

Gln Ile Ile Gly Tyr Val Ile Gly Thr Gln Ala Thr Pro Gly Pro
1               5                   10                  15

Ala Tyr Ser Gly Arg
            20

<210> SEQ ID NO 103
<211> LENGTH: 13
<212> TYPE: PRT
<213> ORGANISM: Homo sapiens

<400> SEQUENCE: 103

Leu Ser Gly Thr Ala Gly Val His Ser Gln Val Gln Leu
1               5                   10

<210> SEQ ID NO 104
<211> LENGTH: 13
<212> TYPE: PRT
<213> ORGANISM: Homo sapiens

<400> SEQUENCE: 104

Ser Asp Leu Val Asn Glu Glu Ala Thr Gly Gln Phe Arg
1               5                   10

<210> SEQ ID NO 105
<211> LENGTH: 9
<212> TYPE: PRT
<213> ORGANISM: Homo sapiens

<400> SEQUENCE: 105

Val Gln Leu Gln Gln Ser Gly Ala Asp
1               5

<210> SEQ ID NO 106
<211> LENGTH: 9
<212> TYPE: PRT
<213> ORGANISM: Homo sapiens

<400> SEQUENCE: 106

His Leu Phe Gly Tyr Ser Trp Tyr Lys
1               5

```
<210> SEQ ID NO 107
<211> LENGTH: 15
<212> TYPE: PRT
<213> ORGANISM: Homo sapiens

<400> SEQUENCE: 107

Gln Leu Leu Gly Leu Leu Leu Cys Phe Gln Gly Thr Arg Cys
1               5                   10                  15

<210> SEQ ID NO 108
<211> LENGTH: 9
<212> TYPE: PRT
<213> ORGANISM: Homo sapiens

<400> SEQUENCE: 108

Ile Gln Met Thr Gln Ile Thr Ser Ser
1               5

<210> SEQ ID NO 109
<211> LENGTH: 12
<212> TYPE: PRT
<213> ORGANISM: Homo sapiens

<400> SEQUENCE: 109

Ser Gly Arg Glu Ile Ile Tyr Pro Asn Ala Ser Leu
1               5                   10

<210> SEQ ID NO 110
<211> LENGTH: 11
<212> TYPE: PRT
<213> ORGANISM: Homo sapiens

<400> SEQUENCE: 110

Gly Val His Ser Gln Val Gln Leu Gln Gln Ser
1               5                   10

<210> SEQ ID NO 111
<211> LENGTH: 5
<212> TYPE: PRT
<213> ORGANISM: Homo sapiens

<400> SEQUENCE: 111

Val Asp Gly Asn Arg
1               5

<210> SEQ ID NO 112
<211> LENGTH: 9
<212> TYPE: PRT
<213> ORGANISM: Homo sapiens

<400> SEQUENCE: 112

Val Lys Pro Gly Ala Ser Val Lys Leu
1               5

<210> SEQ ID NO 113
<211> LENGTH: 11
<212> TYPE: PRT
<213> ORGANISM: Homo sapiens

<400> SEQUENCE: 113

Val Gly Asp Arg Val Thr Ile Thr Cys Arg Ala
1               5                   10

<210> SEQ ID NO 114
<211> LENGTH: 14
```

<212> TYPE: PRT
<213> ORGANISM: Homo sapiens

<400> SEQUENCE: 114

Lys Gly Glu Arg Val Asp Gly Asn Arg Gln Ile Ile Gly Tyr
1               5                   10

<210> SEQ ID NO 115
<211> LENGTH: 13
<212> TYPE: PRT
<213> ORGANISM: Homo sapiens

<400> SEQUENCE: 115

Thr Cys Arg Ala Ser Gln Ser Ile Ser Ser Tyr Leu Asn
1               5                   10

<210> SEQ ID NO 116
<211> LENGTH: 10
<212> TYPE: PRT
<213> ORGANISM: Homo sapiens

<400> SEQUENCE: 116

Val Lys Pro Gly Ala Ser Val Lys Leu Ser
1               5                   10

<210> SEQ ID NO 117
<211> LENGTH: 7
<212> TYPE: PRT
<213> ORGANISM: Homo sapiens

<400> SEQUENCE: 117

Ala Ser Val Lys Leu Ser Cys
1               5

<210> SEQ ID NO 118
<211> LENGTH: 18
<212> TYPE: PRT
<213> ORGANISM: Homo sapiens

<400> SEQUENCE: 118

Cys Lys Ala Ser Gly Tyr Thr Phe Thr Asn Tyr Trp Ile Asn Trp Val
1               5                   10                  15

Lys Pro

<210> SEQ ID NO 119
<211> LENGTH: 118
<212> TYPE: PRT
<213> ORGANISM: Homo sapiens

<400> SEQUENCE: 119

Gln Val Gln Leu Gln Gln Ser Gly Ala Asp Leu Ala Arg Pro Gly Ala
1               5                   10                  15

Ser Val Met Leu Ser Cys Arg Ala Ser Gly Asn Thr Phe Thr Asp Ser
            20                  25                  30

Tyr Ile Asn Trp Val Lys Gln Arg Pro Gly Gln Gly Leu Glu Trp Ile
        35                  40                  45

Gly Glu Ile Tyr Pro Gly Asn Gly Asp Val Tyr Tyr Asn Glu Asn Phe
    50                  55                  60

Lys Asp Lys Ala Thr Leu Thr Ala Asp Lys Ser Ser Asn Thr Ala Tyr
65                  70                  75                  80

Met Lys Leu Ser Ser Leu Thr Ser Gly Asp Ser Ala Val Tyr Leu Cys
                85                  90                  95

Ala Gly Ser Asn Met Ile Thr Thr Val Phe Ala Tyr Trp Gly Gln Gly
            100                 105                 110

Thr Leu Val Thr Val Ser
        115

<210> SEQ ID NO 120
<211> LENGTH: 108
<212> TYPE: PRT
<213> ORGANISM: Homo sapiens

<400> SEQUENCE: 120

Asp Ile Gln Met Thr Gln Ile Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Ser Tyr Thr Ser Arg Leu His Ser Gly Val Pro Ser Arg Phe Ser Gly
50                  55                  60

Ser Gly Ser Gly Thr Asp Tyr Ser Leu Ile Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 121
<211> LENGTH: 112
<212> TYPE: PRT
<213> ORGANISM: Homo sapiens

<400> SEQUENCE: 121

Gln Val Gln Leu Glu Glu Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Thr Arg Ala Asn Tyr Asn Glu Lys Phe
50                  55                  60

Lys Ser Lys Ala Thr Leu Thr Val Asp Thr Ser Ser Ser Thr Ala Tyr
65                  70                  75                  80

Met Gln Val Ser Ser Leu Thr Ser Asp Ser Ala Val Tyr Tyr Cys
                85                  90                  95

Thr Arg Thr His Ser Ile Trp Gly Gln Gly Thr Gln Val Thr Val Ser
            100                 105                 110

<210> SEQ ID NO 122
<211> LENGTH: 110
<212> TYPE: PRT
<213> ORGANISM: Homo sapiens

<400> SEQUENCE: 122

Asp Ile Val Leu Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

-continued

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                 85                  90                  95

Leu Phe Gly Gln Gly Thr Lys Val Glu Ile Lys Arg Ala Asp
             100                 105                 110
```